(12) United States Patent
Kriesel

(10) Patent No.: US 8,622,965 B2
(45) Date of Patent: *Jan. 7, 2014

(54) TWO PART FLUID DISPENSER

(75) Inventor: Marshall S. Kriesel, St. Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 12/455,645

(22) Filed: Jun. 3, 2009

(65) Prior Publication Data

US 2010/0056995 A1 Mar. 4, 2010

Related U.S. Application Data

(63) Continuation-in-part of application No. 12/231,556, filed on Sep. 3, 2008, now Pat. No. 8,480,656.

(51) Int. Cl.
*A61M 5/20* (2006.01)
*A61M 5/00* (2006.01)
*A61M 5/24* (2006.01)
*A61M 5/28* (2006.01)
*F04B 43/00* (2006.01)

(52) U.S. Cl.
USPC ............ 604/134; 604/207; 604/200; 417/472

(58) Field of Classification Search
USPC ............. 604/85, 86, 191, 156, 157, 134–139, 604/246, 207, 212, 216, 132, 133, 53; 417/472, 473
See application file for complete search history.

(56) References Cited

U.S. PATENT DOCUMENTS

| 2,236,084 | A |  | 3/1941 | Brown |  |
|---|---|---|---|---|---|
| 3,884,228 | A |  | 5/1975 | Hahn |  |
| 4,578,060 | A | * | 3/1986 | Huck et al. | 604/133 |
| 5,009,251 | A |  | 4/1991 | Pike et al. |  |
| 5,380,287 | A |  | 1/1995 | Kikuchi et al. |  |
| 5,632,315 | A |  | 5/1997 | Rose |  |
| 6,056,716 | A |  | 5/2000 | D'Antonio et al. |  |
| 6,236,624 | B1 |  | 5/2001 | Kriesel et al. |  |
| 6,332,876 | B1 | * | 12/2001 | Poynter et al. | 604/212 |
| 6,355,019 | B1 |  | 3/2002 | Kriesel et al. |  |
| 6,416,495 | B1 |  | 7/2002 | Kriesel et al. |  |
| 7,220,245 | B2 | * | 5/2007 | Kriesel | 604/134 |
| 2005/0033232 | A1 | * | 2/2005 | Kriesel | 604/131 |
| 2005/0038387 | A1 | * | 2/2005 | Kriesel et al. | 604/133 |
| 2006/0206052 | A1 | * | 9/2006 | Kriesel et al. | 604/82 |
| 2008/0027376 | A1 | * | 1/2008 | Kriesel et al. | 604/84 |
| 2008/0319385 | A1 | * | 12/2008 | Kriesel et al. | 604/88 |

* cited by examiner

*Primary Examiner* — Nicholas Lucchesi
*Assistant Examiner* — Jenna Zhang
(74) *Attorney, Agent, or Firm* — James E. Brunton

(57) ABSTRACT

A dispensing device for dispensing first and second medicaments to a patient that is made up of first and second stand-alone, interconnectable assemblies. The first of these assemblies comprises a fluid reservoir assembly that houses a fluid reservoir defining component while the second assembly comprises a fluid delivery and control assembly that includes an adding assembly for controllably dispensing the second medicament to the patient, a novel flow control means that functions to control the flow of medicinal fluid from the fluid reservoir of the first assembly toward the patient via a plurality of fluid flow control passageways. Because the stand-alone fluid delivery and control assembly is initially totally separate from the fluid reservoir assembly of the apparatus, the fluid flow passageways of the fluid delivery and control assembly can be effectively sterilized using conventional gamma ray sterilization techniques without adversely affecting the medicament contained within the fluid reservoir of the apparatus.

11 Claims, 47 Drawing Sheets

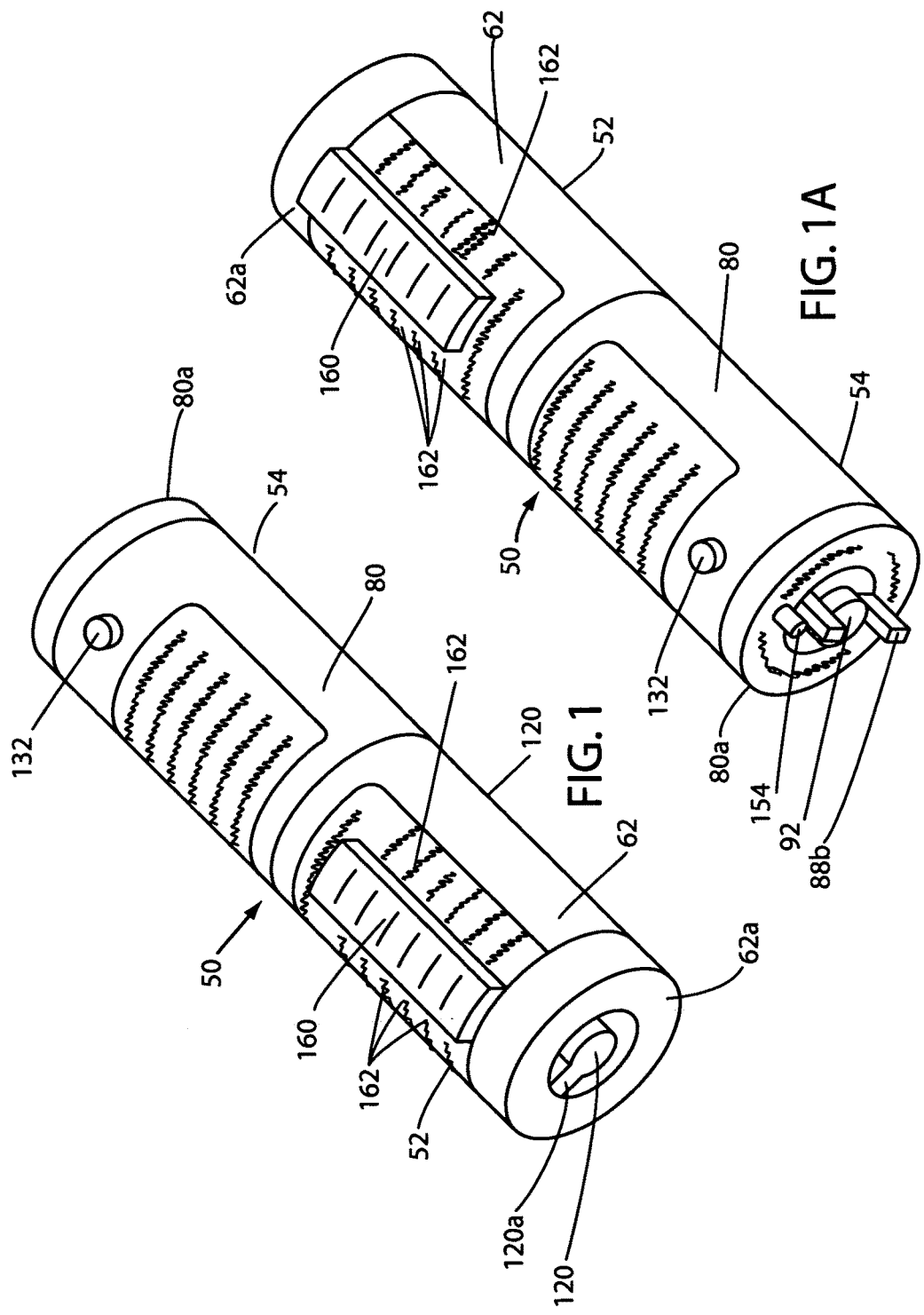

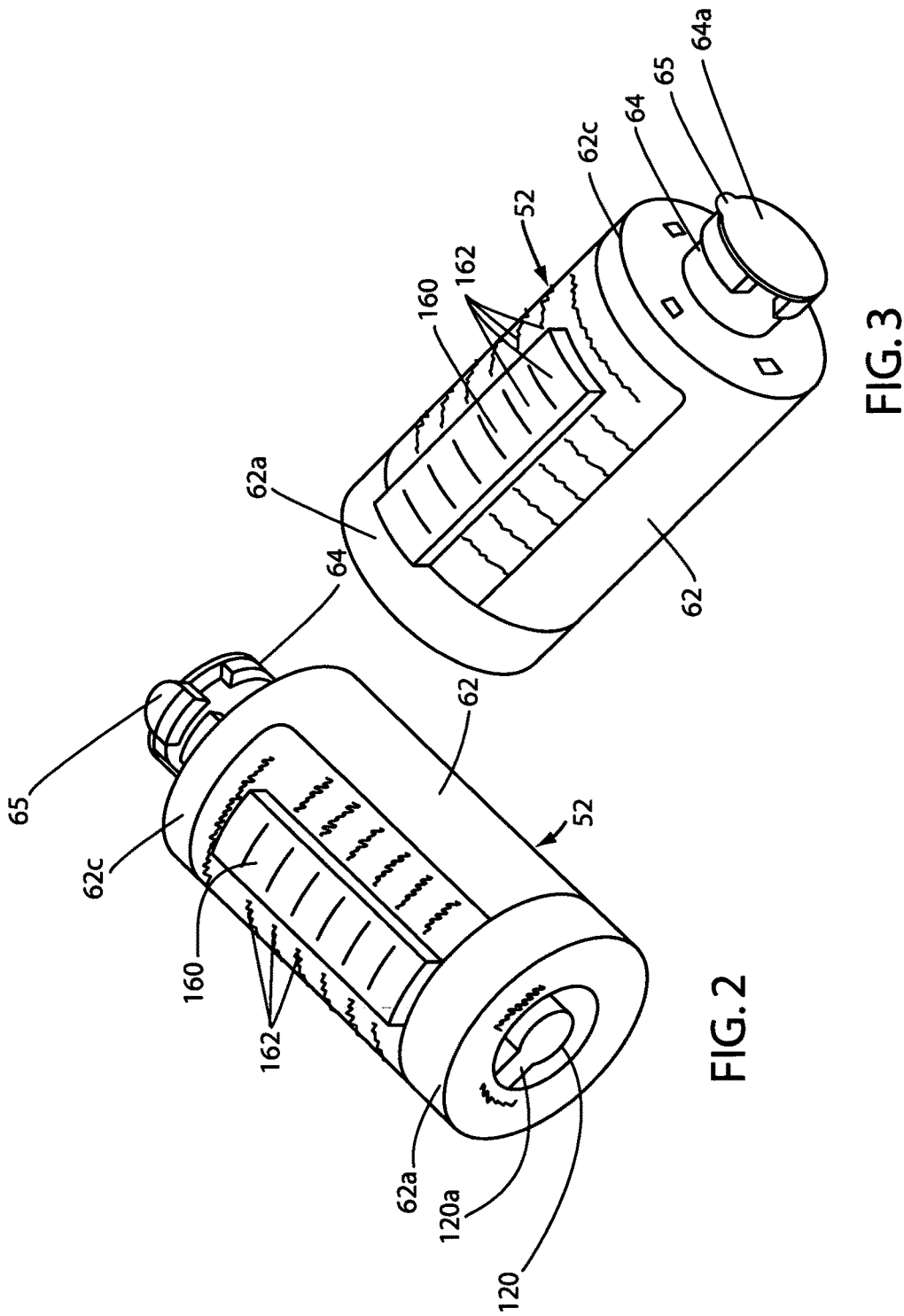

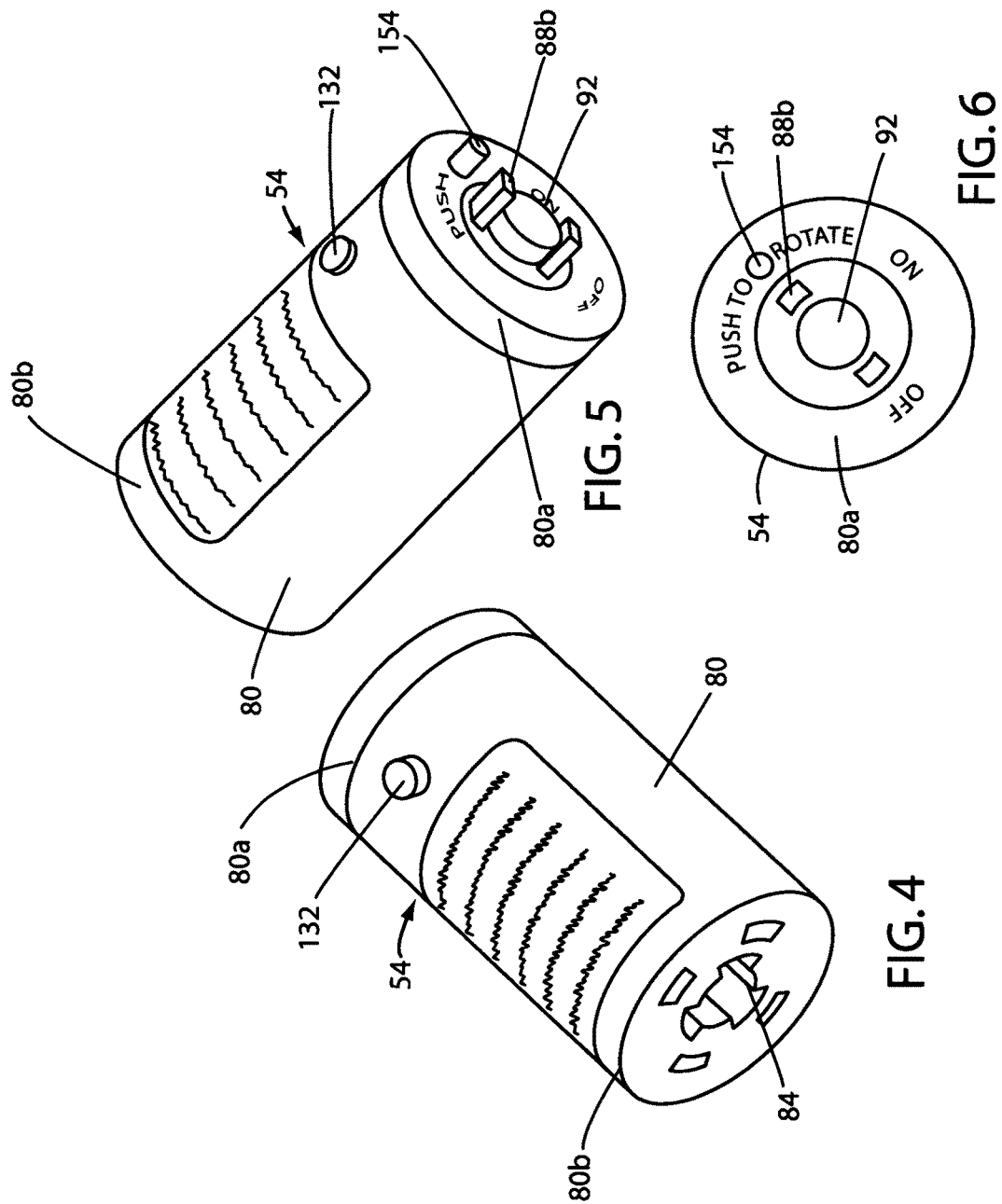

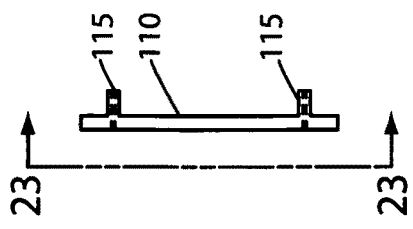
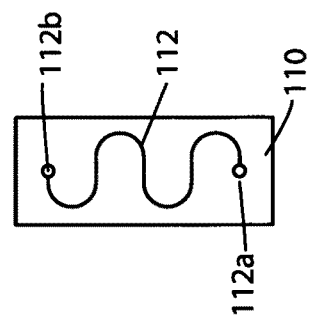
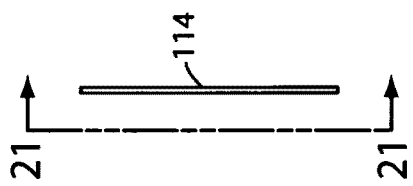
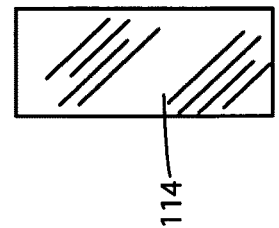
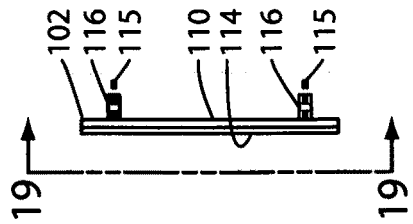
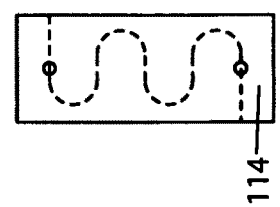

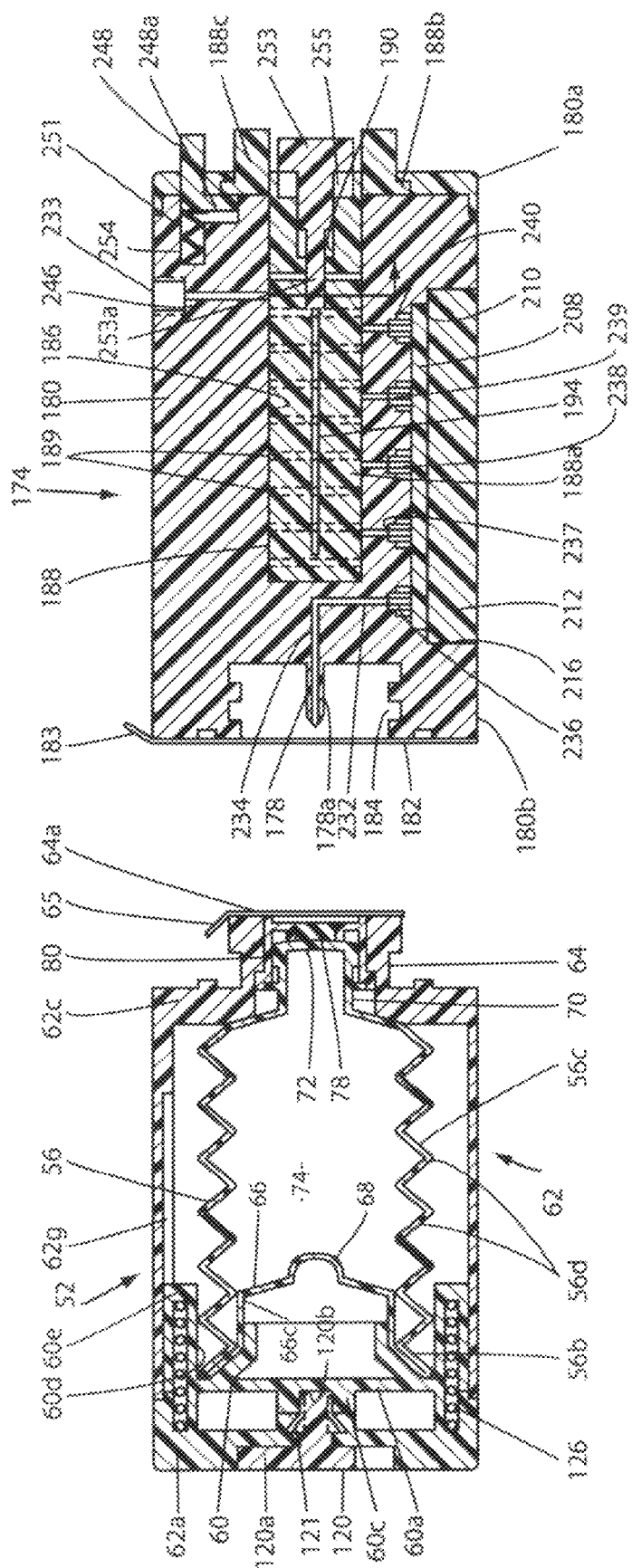

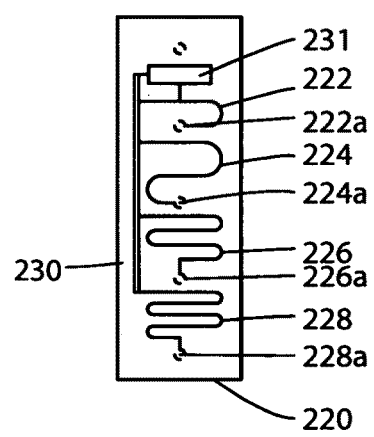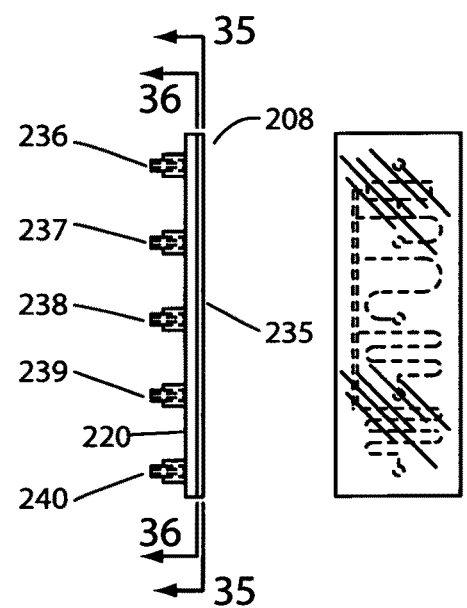
FIG. 36    FIG. 34    FIG. 35

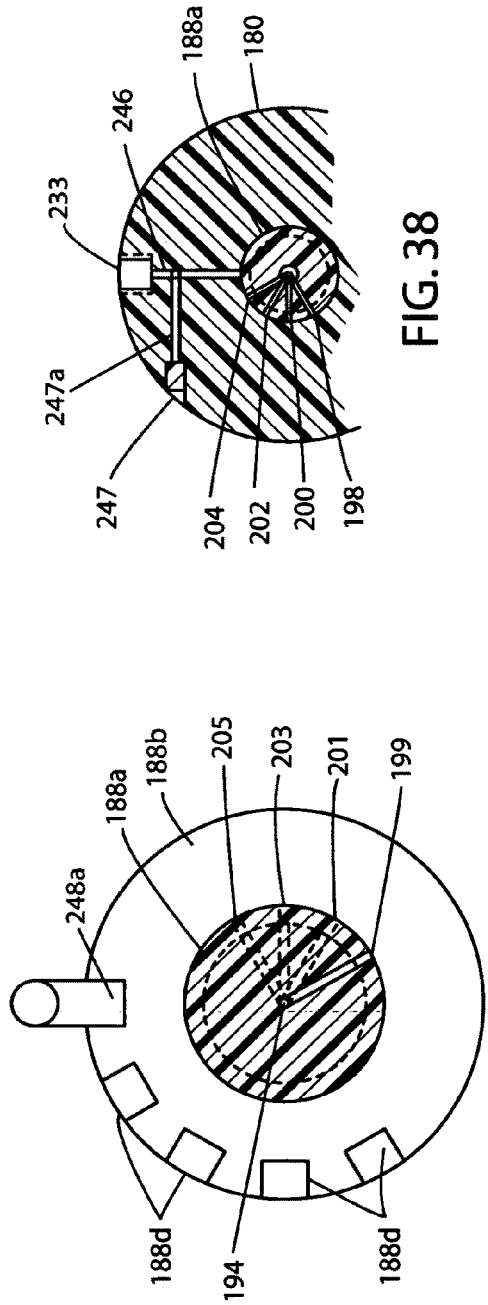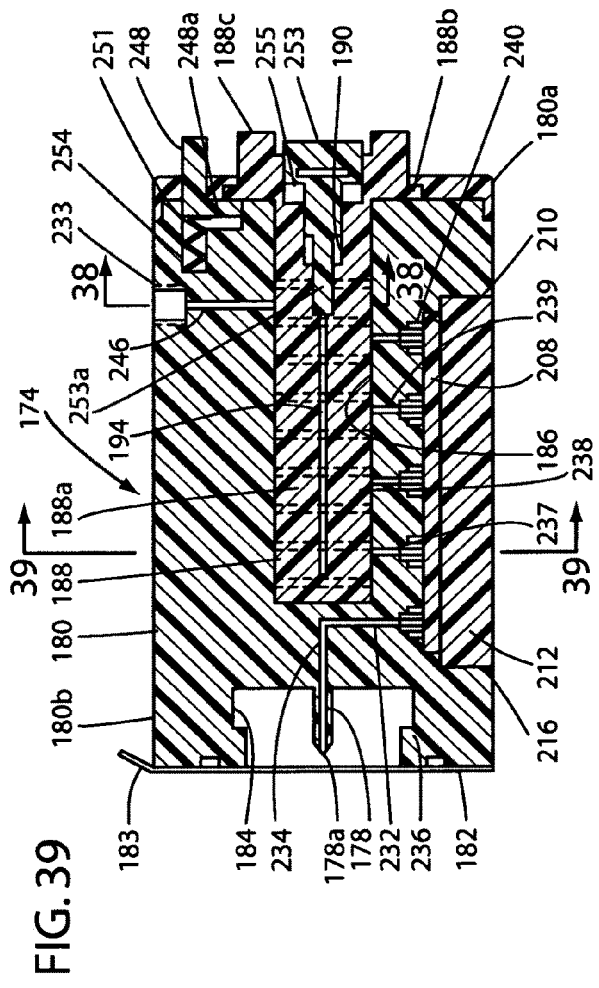

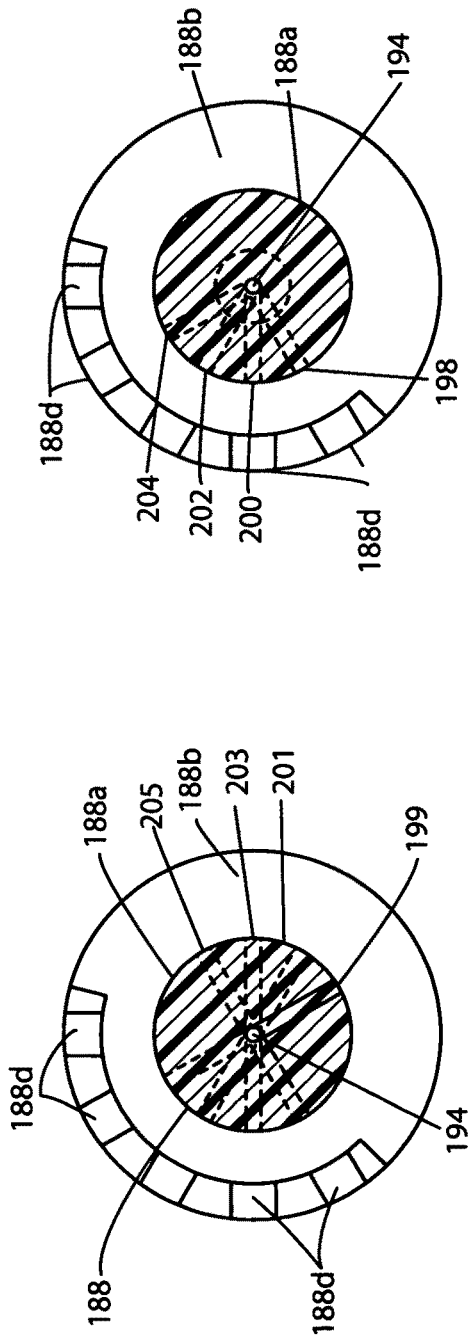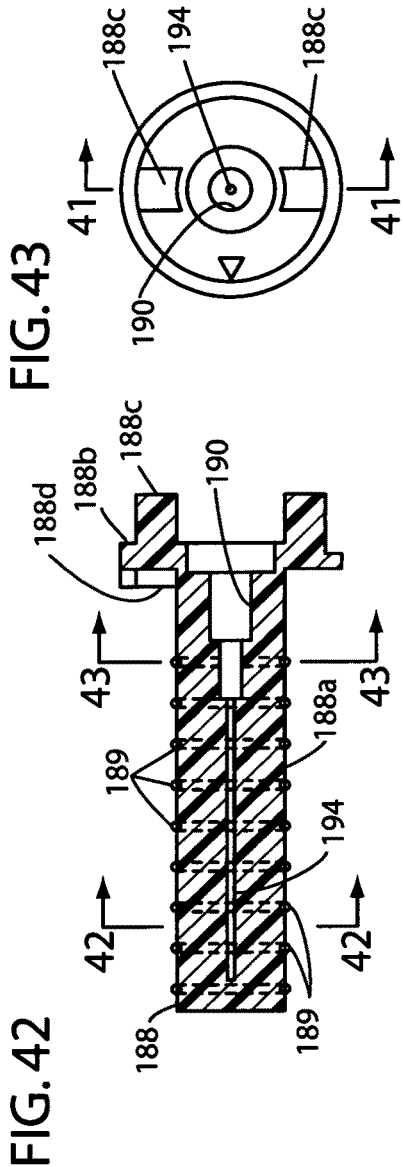

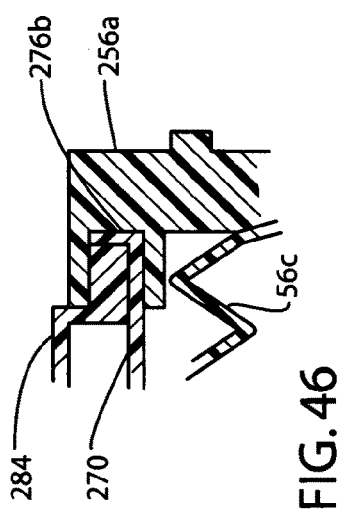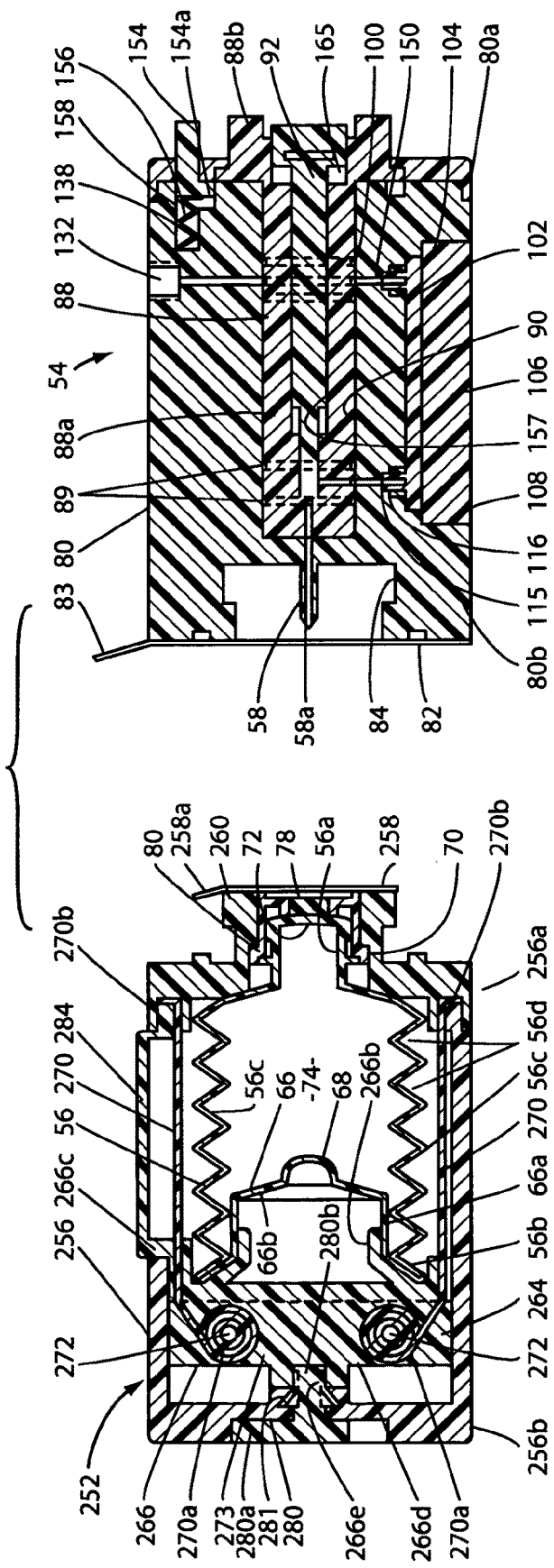

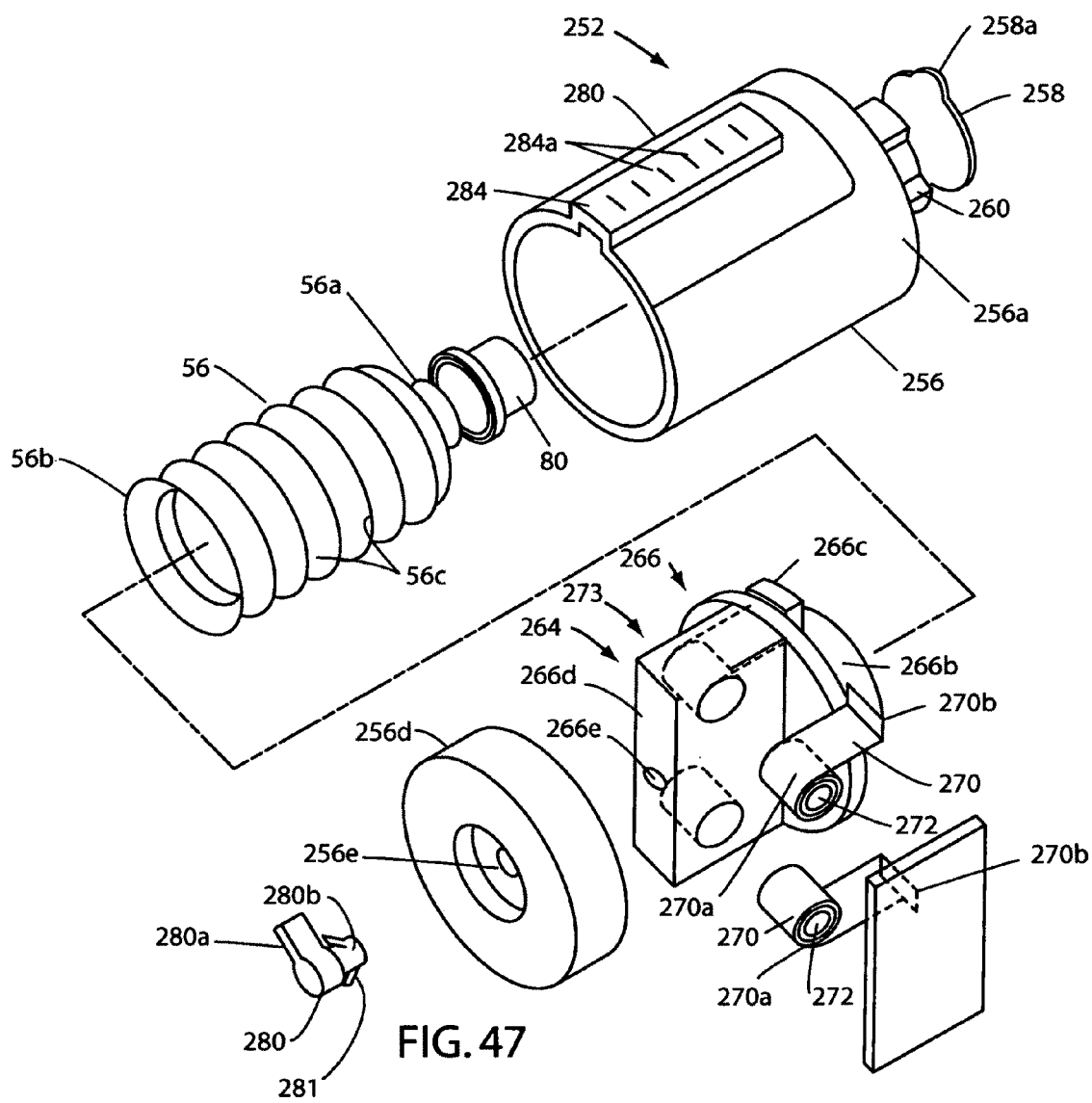

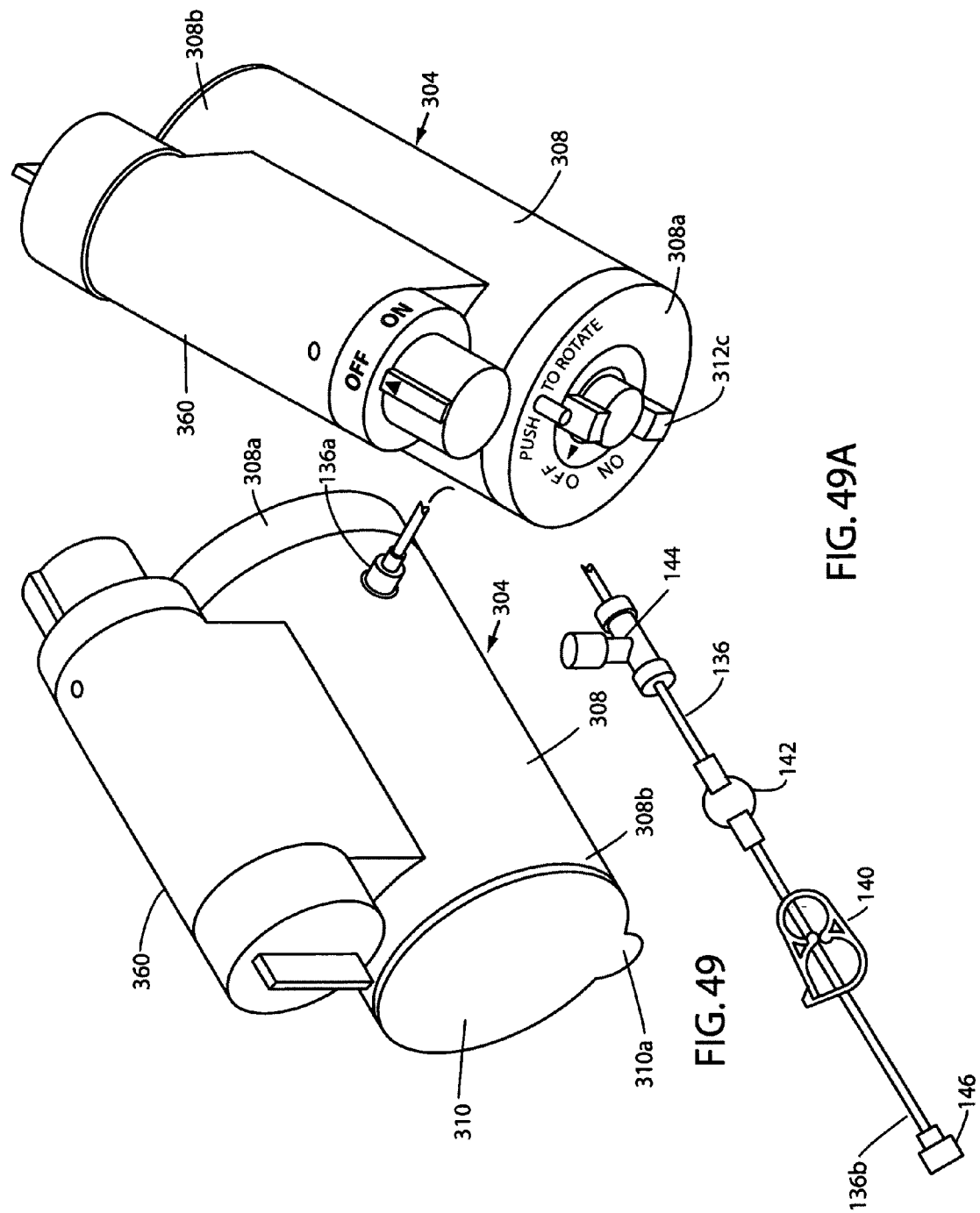

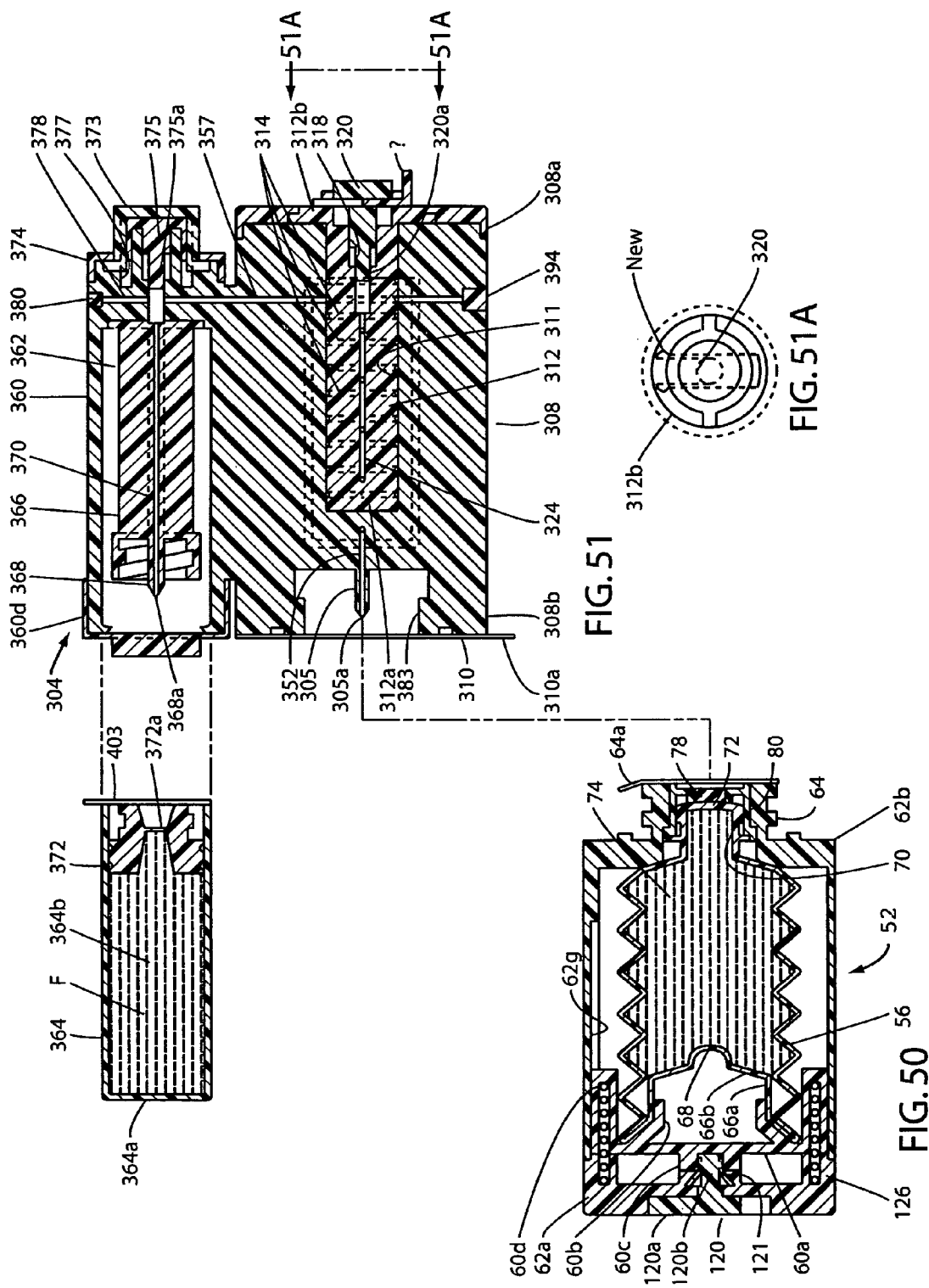

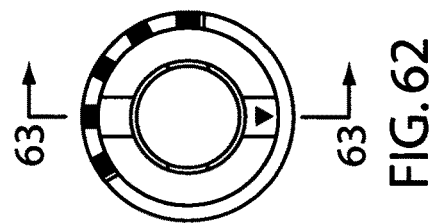
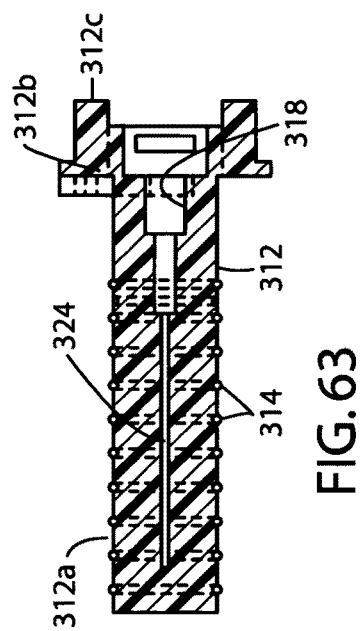
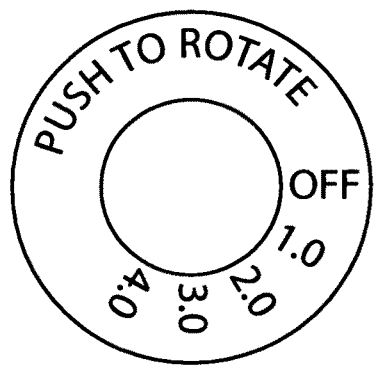
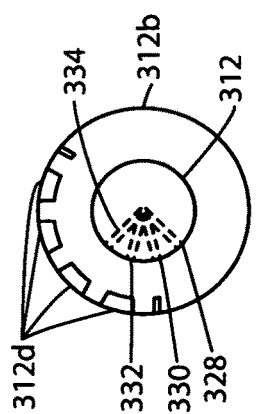

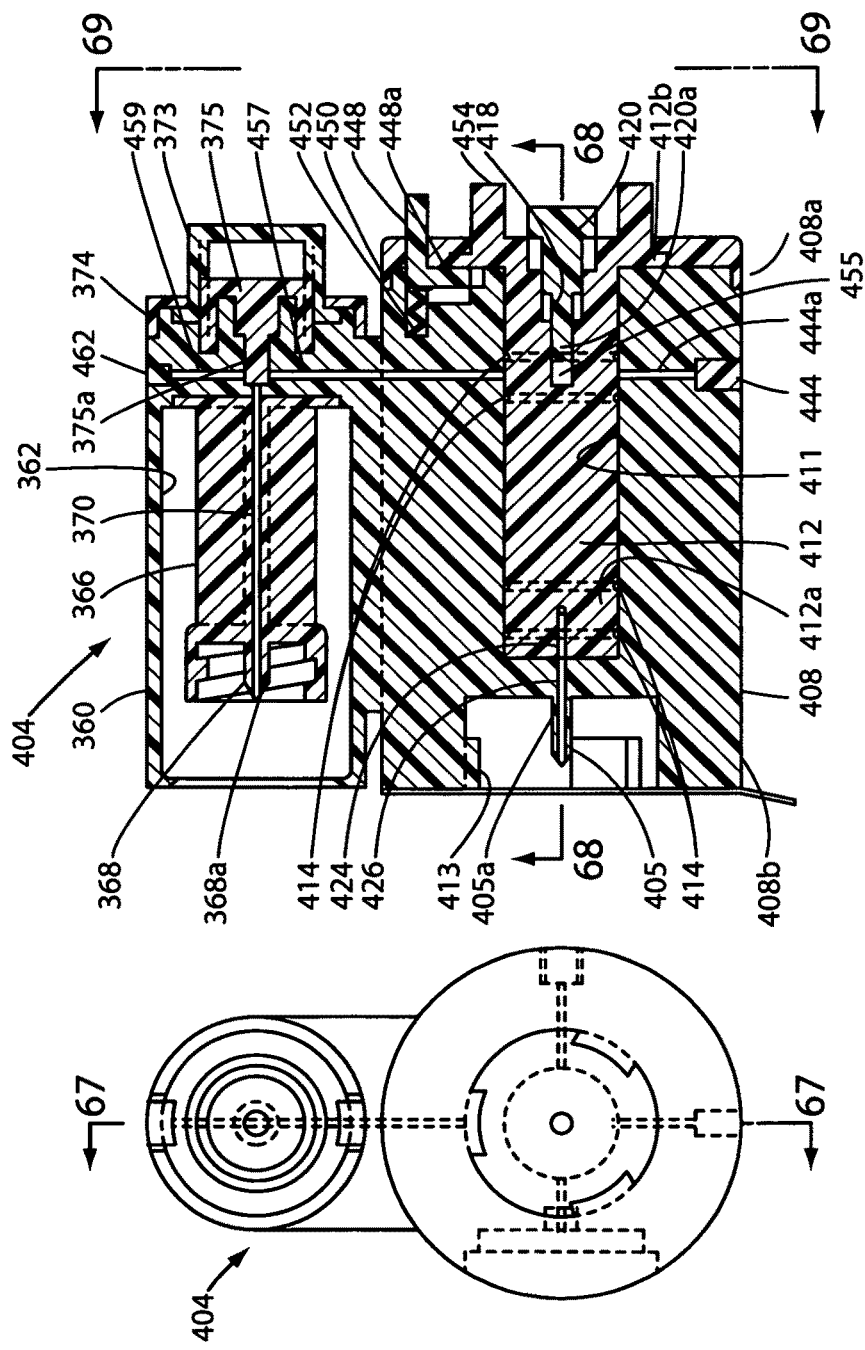

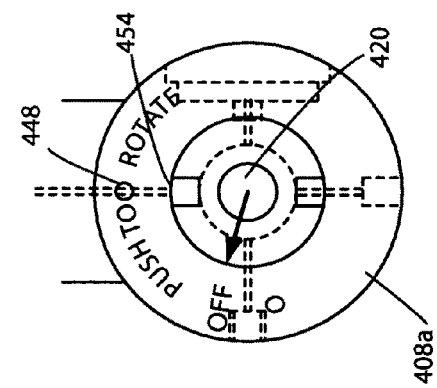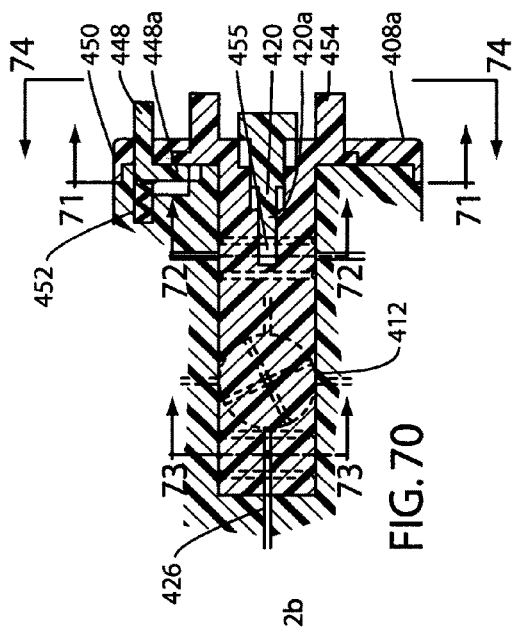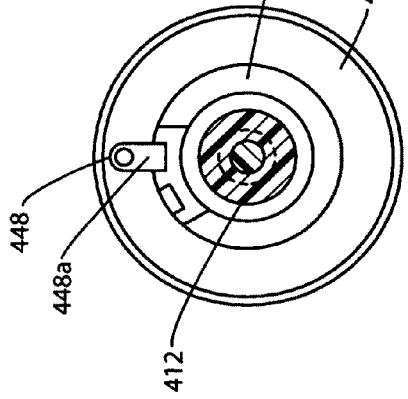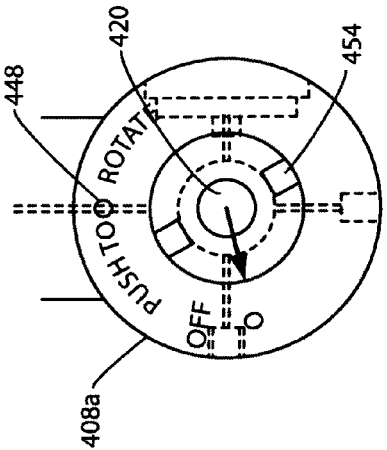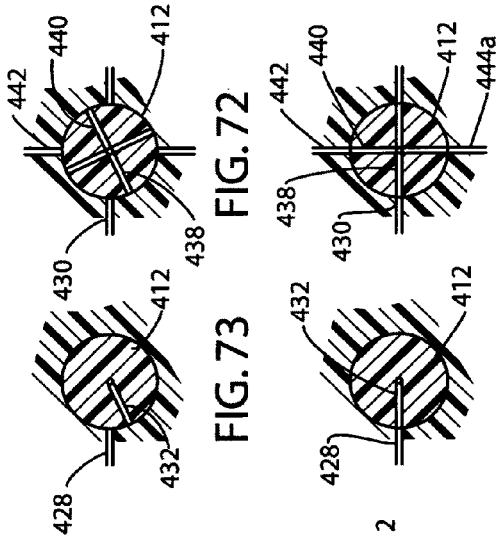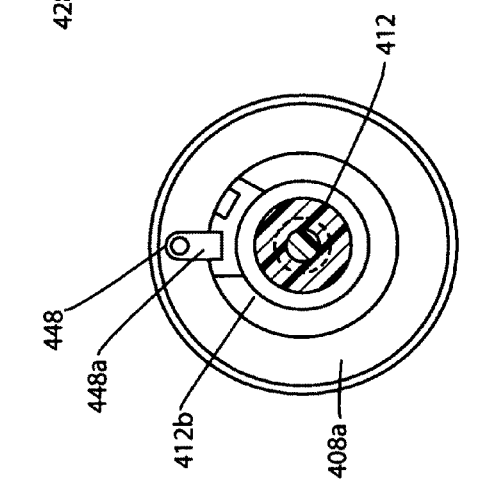

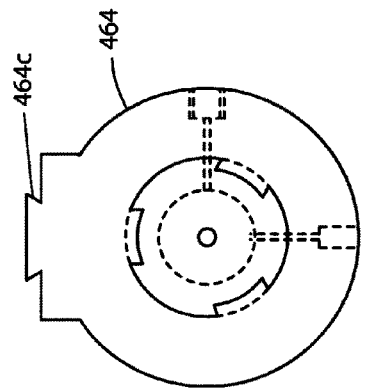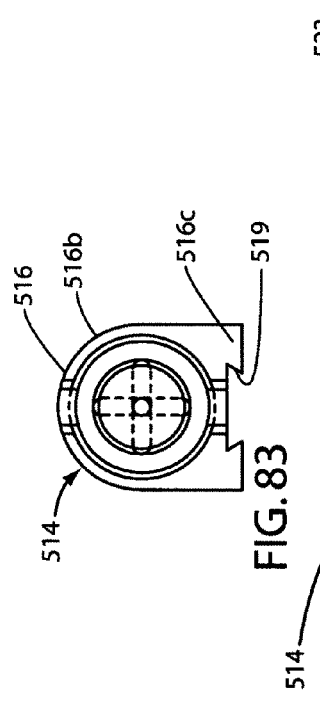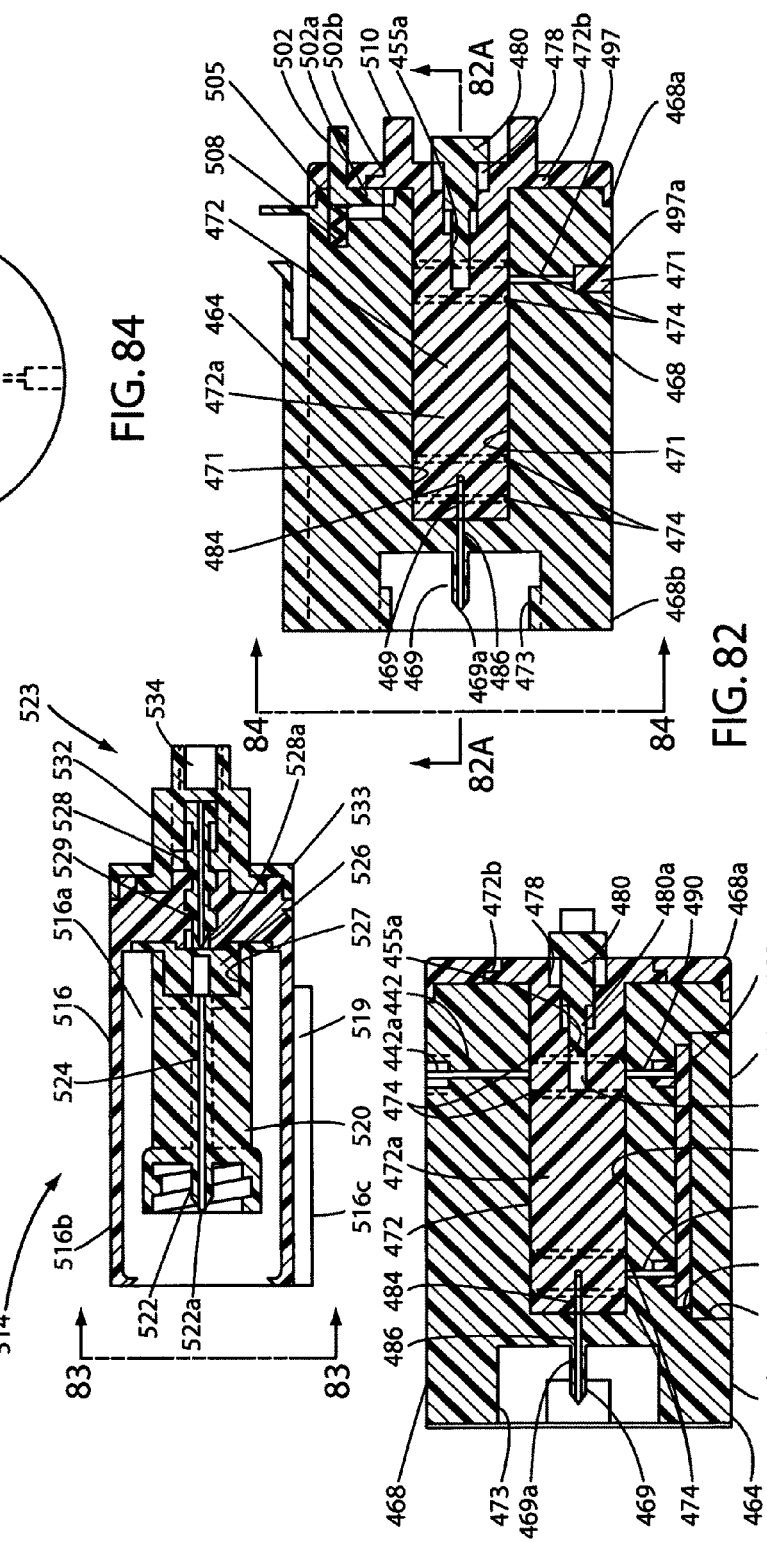

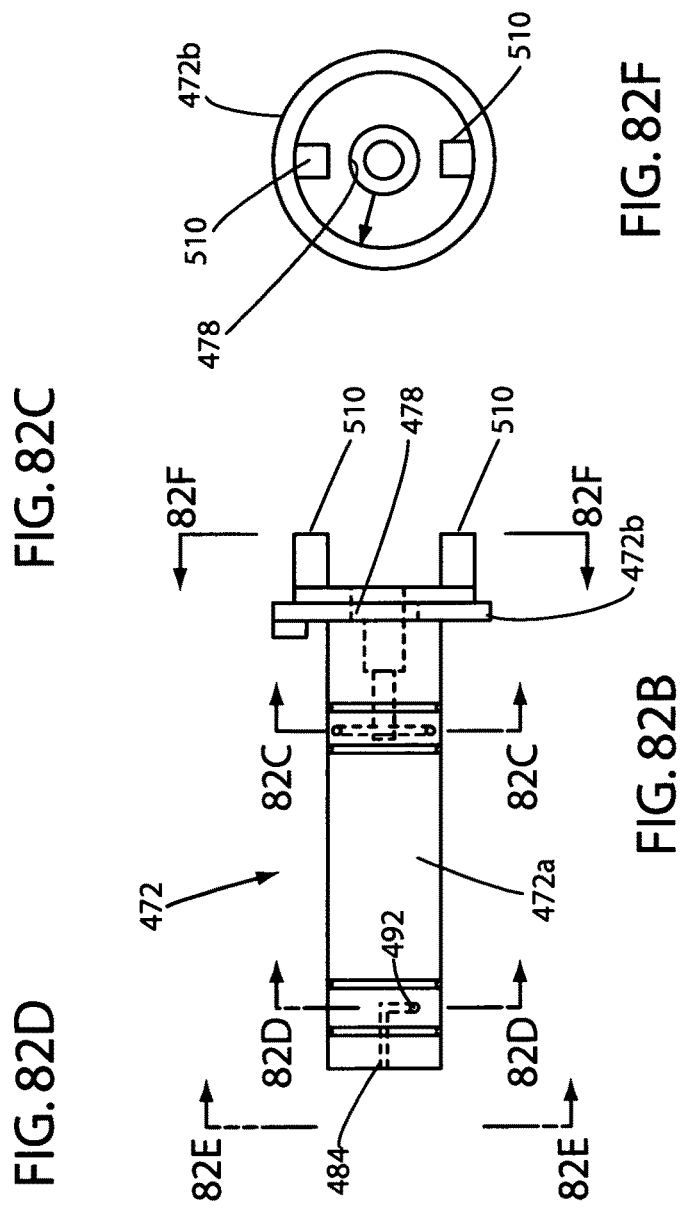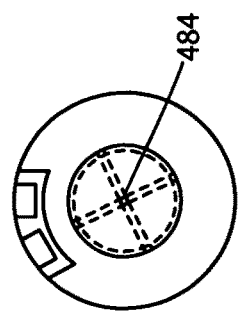
FIG. 82F
FIG. 82C
FIG. 82B
FIG. 82D
FIG. 82E

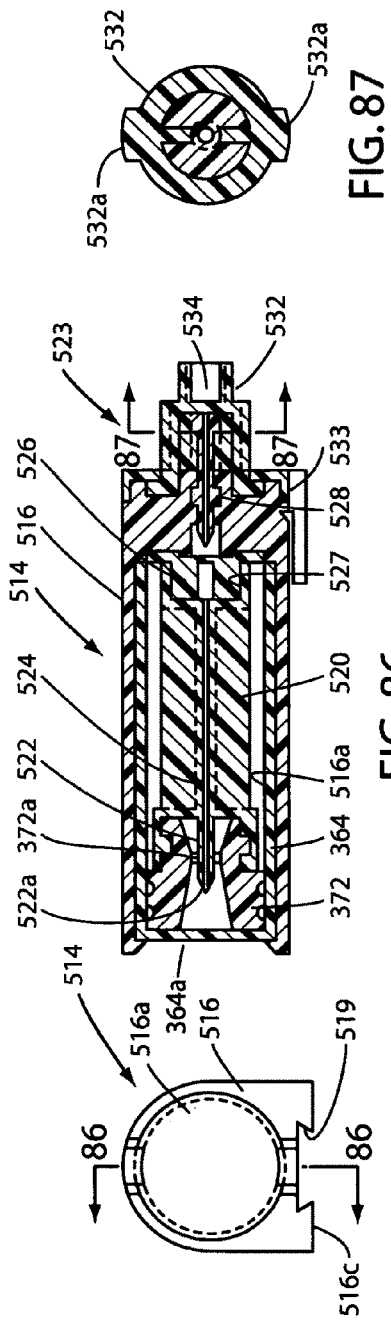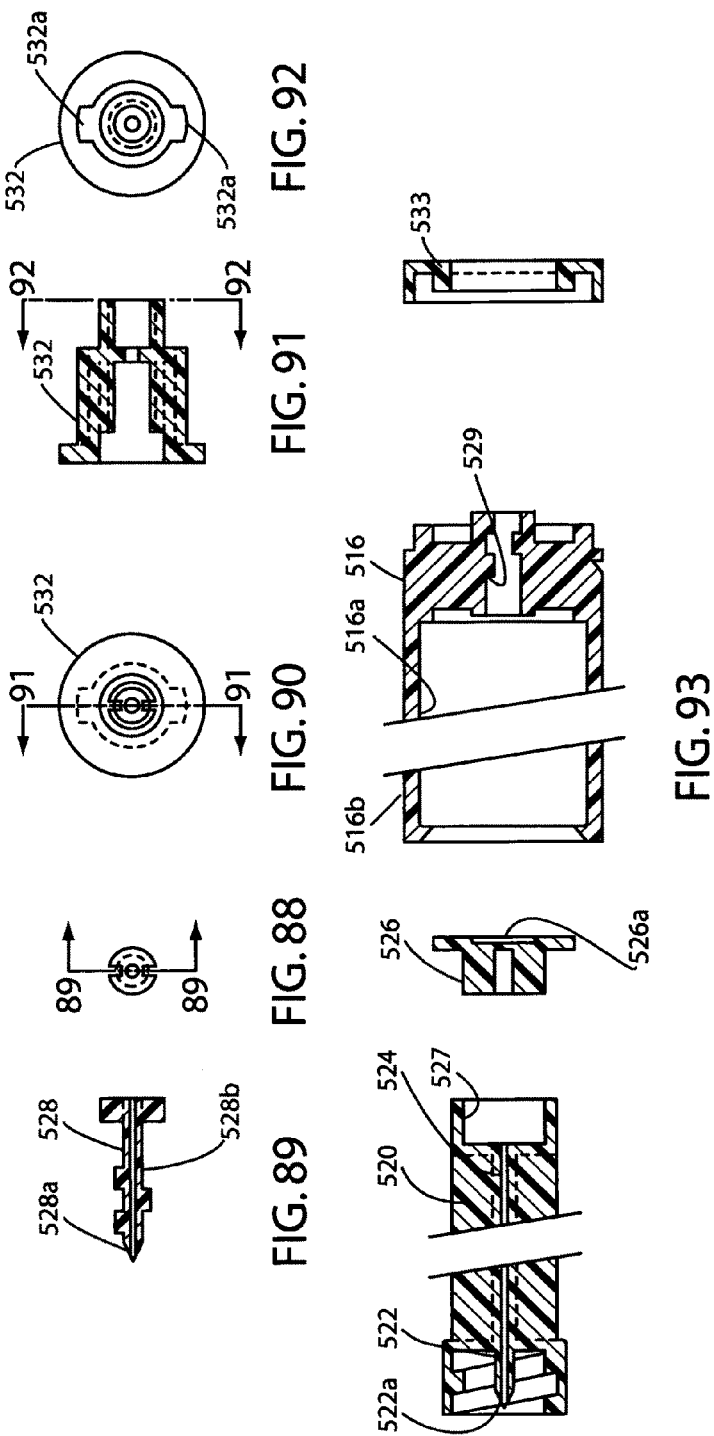

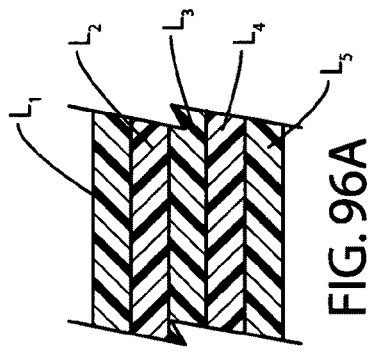
FIG.96A
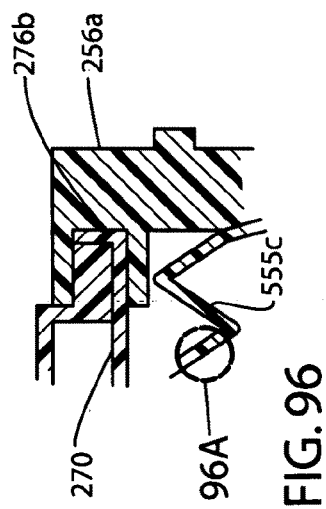
FIG.96
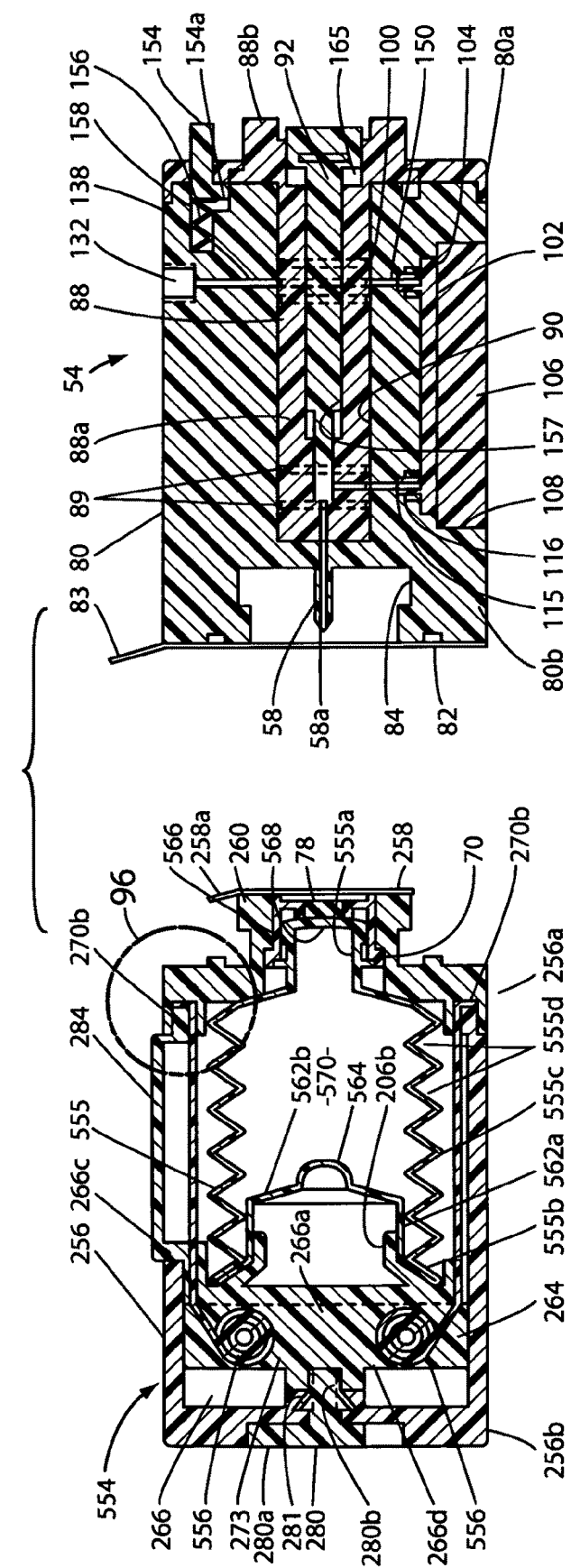
FIG.95
FIG.94

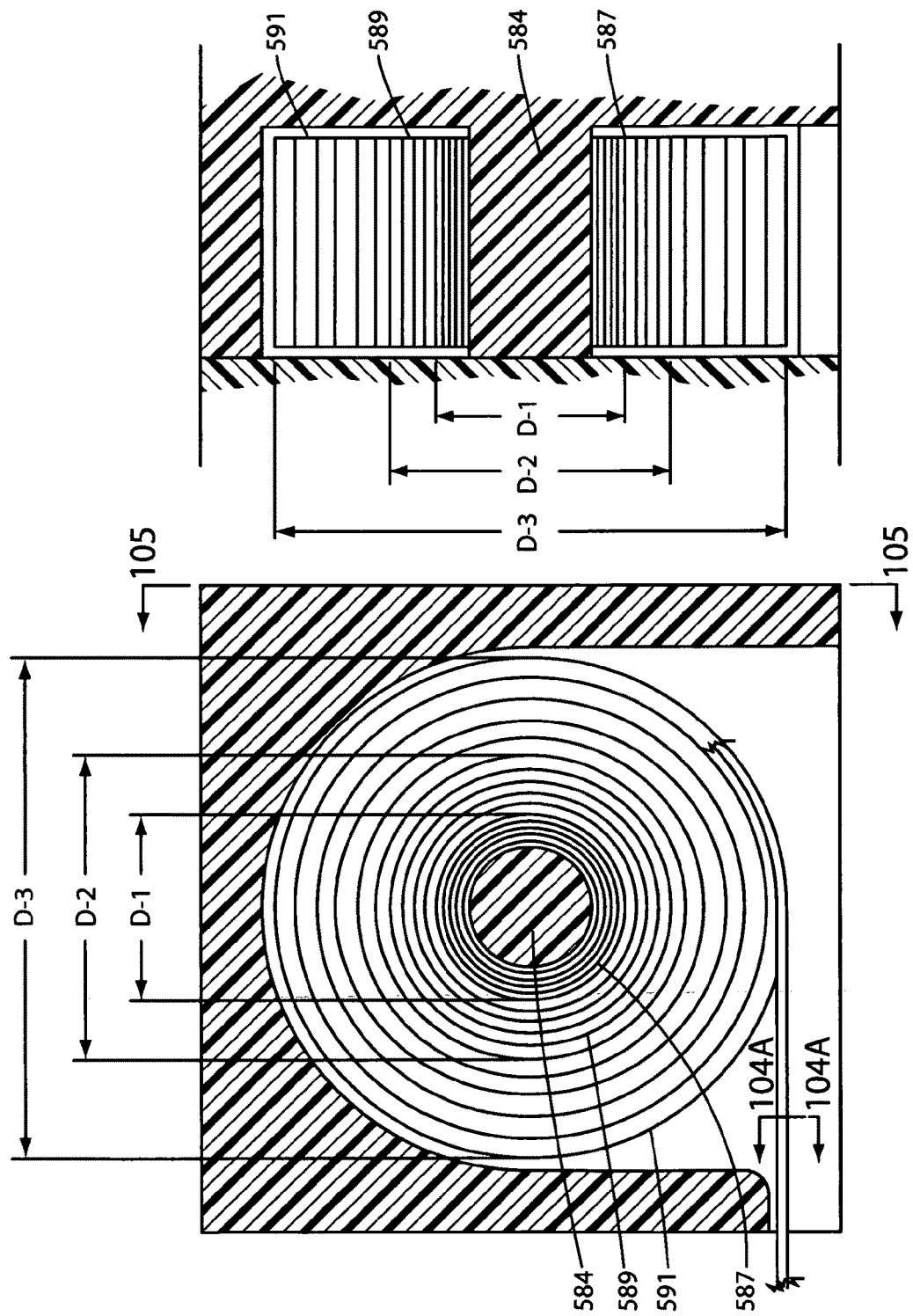

TWO PART FLUID DISPENSER

CROSS-REFERENCE TO RELATED APPLICATIONS

This is a Continuation-In Part of U.S. application Ser. No. 12/231,556 filed Sep. 3, 2008 now U.S. Pat. No. 8,480,656.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

The present invention relates generally to fluid dispensing devices. More particularly, the invention concerns a two part medicament dispenser for dispensing medicinal fluids to ambulatory patients that uniquely enables sterilization of the fluid flow channels without adversely affecting the medicament contained within the reservoir of the apparatus.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

A more recent fluid dispensing apparatus invented by one of the named inventors of the present application is disclosed in U.S. Pat. No. 7,220,245. This apparatus comprises a compact fluid dispenser for use in controllably dispensing fluid medicaments, such as, antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

BRIEF SUMMARY OF THE INVENTION

By way of brief summary, one form of the dispensing device of the present invention for dispensing medicaments to a patient comprises first and second stand-alone, interconnectable assemblies. The first of these assemblies comprises a fluid reservoir assembly that houses a fluid reservoir defining component while the second assembly comprises a fluid delivery and control assembly that includes a novel flow control means that functions to control the flow of medicinal fluid from the fluid reservoir of the first assembly toward the patient via a plurality of fluid flow control passageways. A novel and highly important feature of the apparatus of the present invention resides in the fact that, because the stand-alone fluid delivery and control assembly is initially totally separate from the fluid reservoir assembly of the apparatus, the fluid flow passageways of the fluid delivery and control assembly can be effectively sterilized using conventional gamma ray sterilization techniques without adversely affecting the medicament contained within the fluid reservoir of the apparatus.

With the forgoing in mind, it is an object of the present invention to provide a novel, two-part fluid dispensing apparatus for use in controllably dispensing fluid medicaments, such as antibiotics, anesthetics, analgesics, and like medicinal agents, at a uniform rate in which the fluid flow passageways of the apparatus can be effectively sterilized using conventional gamma ray sterilization techniques without adversely affecting the medicament contained within the fluid reservoir of the apparatus.

Another object of the invention is to provide a fluid dispensing apparatus of the aforementioned character dispenser of simple construction and one that can be used in the home care environment with a minimum amount of training.

Another object of the invention is to allow infusion therapy to be initiated quickly at the point of care without the assistance of a medical professional.

Another object of the invention is to provide a novel, two part dispensing apparatus in which a stored energy source is provided in the form of a compressible, expandable or retractable member of novel construction that provides the force necessary to continuously and uniformly expel fluid from the device reservoir.

Another object of the invention is to provide a dispenser of the character described in the preceding paragraphs in which the stored energy source is provided in the form of a constant force spring that comprises a tightly coiled wound band of pre-hardened spring steel or stainless steel strip with built-in curvature so that each turn of the strip wraps tightly on its inner neighbor. When the strip is extended (deflected), the inherent stress resists the loading force; the same as a common extension spring but at a nearly constant (zero) rate.

Another object of the invention is to provide a dispenser of the class described which includes a fluid flow control assembly that precisely controls the flow of the medicament solution to the patient.

Another object of the invention is to provide a dispenser of the type described which includes a fluid flow control assembly that, in turn, includes novel adding means for delivering selected additional medicaments to the patient.

Another object of the invention is to provide a fluid dispensing apparatus that enables precise variable flow rate selection.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described which is compact and lightweight, is easy for ambulatory patients to use and is extremely reliable in operation.

Another object of the invention is to provide a fluid dispensing apparatus that is easy and inexpensive to manufacture in large quantities.

BRIEF DESCRIPTION OF THE SEVERAL VIEWS OF THE DRAWINGS

FIG. 1 is a generally perspective rear view of one form of the two-part fluid delivery system of the present invention.

FIG. 1A is a generally perspective front view of the two-part fluid delivery system illustrated in FIG. 1.

FIG. 2 is a generally perspective rear view of one form of the first stand-alone component of the invention that comprises the fluid reservoir assembly that houses a fluid reservoir defining component.

FIG. 3 is a generally perspective front view of the first stand-alone component of the invention shown in FIG. 2.

FIG. 4 is a generally perspective rear view of one form of the second stand-alone component of the invention that comprises a fluid delivery and control assembly that includes a novel flow control means that functions to control the flow of medicinal fluid from the fluid reservoir of the first stand-alone component toward the patient.

FIG. 5 is a generally perspective front view of the second stand-alone component of the invention shown in FIG. 4.

FIG. 6 is a front view of the second stand-alone component of the invention shown in FIG. 5.

FIG. 18 is a side elevational view of one form of the rate control plate assembly of the second stand-alone component that includes a rate control plate and the rate control plate cover.

FIG. 19 is a view taken along lines 19-19 of FIG. 18.

FIG. 20 is a side elevational view of one form of the rate control plate cover of the second stand-alone component.

FIG. 21 is a view taken along lines 21-21 of FIG. 20.

FIG. 22 is a side elevational view of the rate control plate of the rate control plate assembly shown in FIG. 18.

FIG. 23 is a view taken along lines 23-23 of FIG. 22.

FIG. 30 is a longitudinal cross-sectional view of an alternate form of the first stand-alone component of the invention.

FIG. 31 is a longitudinal cross-sectional view of an alternate form of the second stand alone component.

FIG. 34 is a side elevational view of one form of the rate control plate assembly of the alternate second stand-alone component of the invention that includes a rate control plate and control plate cover.

FIG. 35 is a view taken along lines 35-35 of FIG. 34.

FIG. 36 is a view taken along lines 36-36 of FIG. 34.

FIG. 37 is a longitudinal cross-sectional view of the alternate form of the second stand-alone component shown in FIG. 31.

FIG. 38 is a cross-sectional view taken along lines 38-38 of FIG. 37.

FIG. 39 is a cross-sectional view taken along lines 39-39 of FIG. 37.

FIG. 40 is a front view of the rate control housing of the alternate second stand-alone component.

FIG. 41 is a cross-sectional view of the rate control housing taken along lines 41-41 of FIG. 40.

FIG. 42 is an enlarged cross-sectional view taken along lines 42-42 of FIG. 41.

FIG. 43 is an enlarged cross-sectional view taken along lines 43-43 of FIG. 41.

FIG. 44 is a longitudinal cross-sectional view of an alternate form of the first stand-alone component of the invention shown in FIGS. 1 and 2.

FIG. 45 is a longitudinal cross-sectional view similar to the second stand-alone component shown in FIGS. 4, 5 and 6.

FIG. 46 is an enlarged fragmentary cross-sectional view of the portion identified as 46 in FIG. 44.

FIG. 47 is a generally perspective exploded view of the second stand-alone component of the invention shown in FIG. 44.

FIG. 49 is a generally perspective rear view of an alternate form of the second stand-alone component of the invention that comprises a fluid delivery and control assembly that includes a novel flow control means that functions to control the flow of medicinal fluid from the fluid reservoir of the first stand-alone component toward the patient.

FIG. 49A is a generally perspective front view of the alternate form of the second stand-alone component of the invention shown in FIG. 49.

FIG. 50 is a longitudinal cross-sectional view of the first stand-alone component of this alternate form of the invention and a longitudinal cross-sectional view of one form of the vial fill assembly of this alternate form of the invention.

FIG. 51 is a longitudinal cross-sectional view of the alternate form of second stand-alone component shown in FIGS. 49 and 49A of the drawings.

FIG. 51A is a view taken along lines 51A-51A of FIG. 51.

FIG. 61 is a view taken along lines 61-61 of FIG. 60.

FIG. 62 is a front view of the rate control shaft of the second stand-alone component shown in FIGS. 49 and 49A of the drawings.

FIG. 63 is a cross-sectional view taken along lines 63-63 of FIG. 62.

FIG. 64 is a view taken along lines 64-64 of FIG. 63.

FIG. 66 is a rear view of the alternate form of second stand-alone component of the invention.

FIG. 67 is a cross-sectional view taken along lines 67-67 of FIG. 66.

FIG. 70 is a fragmentary cross-sectional view of the control shaft and control shaft operating mechanism of the second stand-alone component shown in FIG. 67.

FIG. 71 is a cross-sectional view taken along lines 71-71 of FIG. 70.

FIG. 72 is a cross-sectional view taken along lines 72-72 of FIG. 70.

FIG. 73 is a cross-sectional view taken along lines 73-73 of FIG. 70.

FIG. 74 is a view taken along lines 74-74 of FIG. 70.

FIG. 75 is a cross-sectional view similar to FIG. 71, but showing the indexing shaft of the device in a fluid delivery position.

FIG. 76 is a cross-sectional view similar to FIG. 73, but showing the inlet passageway of the control shaft of the device in a fluid delivery position.

FIG. 77 is a cross-sectional view similar to FIG. 72, but showing the outlet passageway of the control shaft of the device in a fluid delivery position.

FIG. 78 is a view similar to FIG. 74, but showing the operating mechanism of the second stand-alone component shown in FIG. 67 as it appears in a fluid delivery position.

FIG. 80A is a generally perspective front view of the alternate form of the apparatus shown in FIG. 80.

FIG. 82 is a longitudinal cross-sectional exploded view of the second stand-alone component of this latest form of the invention in which the vial receiving portion of the medicament vial assembly is removably connected to the control portion of the second stand-alone component.

FIG. 82A is a view taken along lines 82A-82A of FIG. 82.

FIG. 82B is a side elevational view of the rate control shaft of the alternate form of second stand-alone component of the invention shown in FIG. 82.

FIG. 82C is a cross-sectional view taken along lines 82C-82C of FIG. 82B.

FIG. 82D is a cross-sectional view taken along lines 82D-82D of FIG. 82B.

FIG. 82E is a view taken along lines 82E-82E of FIG. 82B.

FIG. 82F is a view taken along lines 82F-82F of FIG. 82B.

FIG. 83 is a view taken along lines 83-83 of FIG. 82.

FIG. 84 is a view taken along lines 84-84 of FIG. 82.

FIG. 85 is a rear view of the removable medicament vial assembly of the second stand-alone component shown in FIG. 82 as it appears with the medicament vial assembled with the vial receiving portion of the medicament vial assembly.

FIG. 86 is a cross-sectional view taken along lines 86-86 of FIG. 85.

FIG. 87 is a cross-sectional view taken along lines 87-87 of FIG. 86.

FIG. 88 is a front view of the piercing needle component of the medicament vial assembly of the second stand-alone component shown in FIG. 82.

FIG. 89 is a cross-sectional view taken along lines 89-89 of FIG. 88.

FIG. 90 is a rear view of the vial control knob of the medicament vial assembly of the second stand-alone component shown in FIG. 82.

FIG. 91 is a cross-sectional view taken along lines 91-91 of FIG. 90.

FIG. 92 is a view taken along lines 92-92 of FIG. 91.

FIG. 93 is an exploded cross-sectional view of the vial receiving portion of the medicament vial assembly of the second stand-alone component shown in FIG. 82.

FIG. 94 is a longitudinal cross-sectional view of still another form of the first stand-alone component of the invention.

FIG. 95 is a longitudinal cross-sectional view similar to FIG. 8 of the second stand-alone component.

FIG. 96 is an enlarged fragmentary cross-sectional view of the portion identified as 96 in FIG. 94.

FIG. 96A is an enlarged fragmentary cross-sectional view of the portion identified as 96A in FIG. 96.

FIG. 101 is a longitudinal cross-sectional view showing the configuration of the collapsible container portion of still another form of the dispensing device of the invention.

FIG. 102 is an enlarged fragmentary cross-sectional view of the area designated in FIG. 101 as "102".

FIG. 103 is a greatly enlarged cross-sectional view of the area designated in FIG. 102 as "103".

FIG. 104 is an enlarged cross-sectional view taken along lines 104-104 of FIG. 101.

FIG. 104A is an enlarged cross-sectional view taken along lines 104A-104A of FIG. 104.

FIG. 105 is a view taken along lines 105-105 of FIG. 104.

FIG. 106 is a generally perspective view of yet another form of variable force spring of the invention.

DETAILED DESCRIPTION OF THE INVENTION

Definitions

Figure 7:
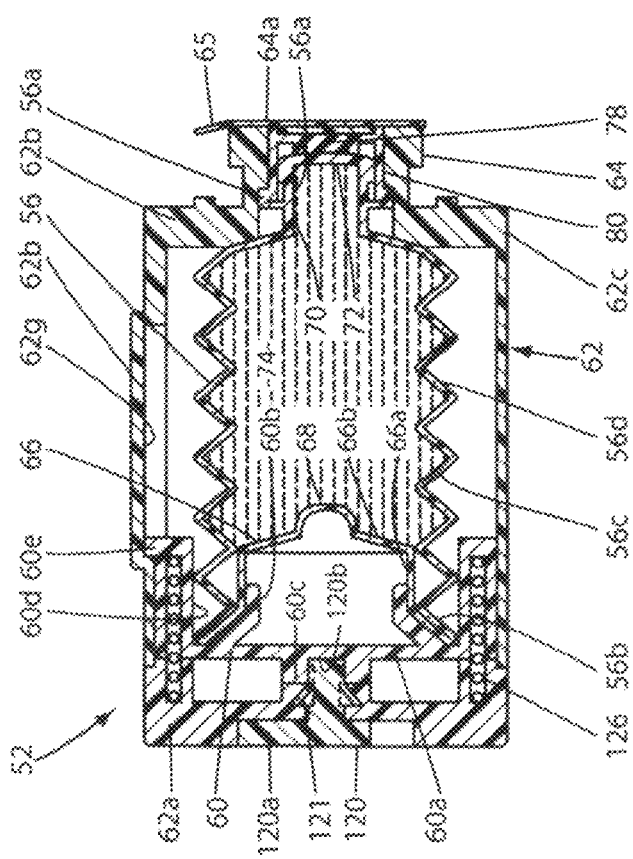
FIG. 7 is a longitudinal cross-sectional view of the first stand-alone component of the invention shown in FIGS. 2 and 3 of the drawings.

As used herein the following terms mean:
Unitary Container:
 A closed container formed from a single component.
Continuous/Uninterrupted Wall:
 A wall having no break in uniformity or continuity.
Hermetically Sealed Container:
 A container that is designed and intended to be secure against the entry of microorganisms and to maintain the safety and quality of its contents after pressurizing.
Aseptic Processing:
 The term 'aseptic processing' as it is applied in the pharmaceutical industry refers to the assembly of sterilized components and product in a specialized clean environment.
Sterile Product:
 A sterile product is one that is free from all living organisms, whether in a vegetative or spore state.
Blow-Fill-Seal Process:
 The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.
Integrally Formed:
 An article of one-piece construction, or several parts that are rigidly secured together, and smoothly continuous in form and that any such components making up the part have been then rendered inseparable.
Frangible:
 An article, item or object that is capable of being ruptured or broken, but does not necessarily imply any inherent materials weakness. A material object, under load that demonstrates a mechanical strain rate deformation behavior, leading to disintegration.
Spring:
 A mechanical element that can be deformed by a mechanical force such that the deformation is directly proportional to the force or torque applied to it. An elastic machine component able to deflect under load in a prescribed manner and able to recover its initial shape when unloaded. The combination of force and displacement in a deflected spring is energy which may be stored when moving loads are being arrested.
Collapsible:
 To cause to fold, break down, or fall down or inward or as in bent-over or doubled-up so that one part lies on another.
Collapsible Container:
 A dispensing apparatus in which one or more walls of the container are made of a material which will deform (collapse) when pressure is applied thereto; or a dispensing apparatus having a collapsible or telescoping wall structure.
Constant Force Spring:
 Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. In use, the spring is usually mounted with the Internal Diameter (ID) tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.

Figure 8:
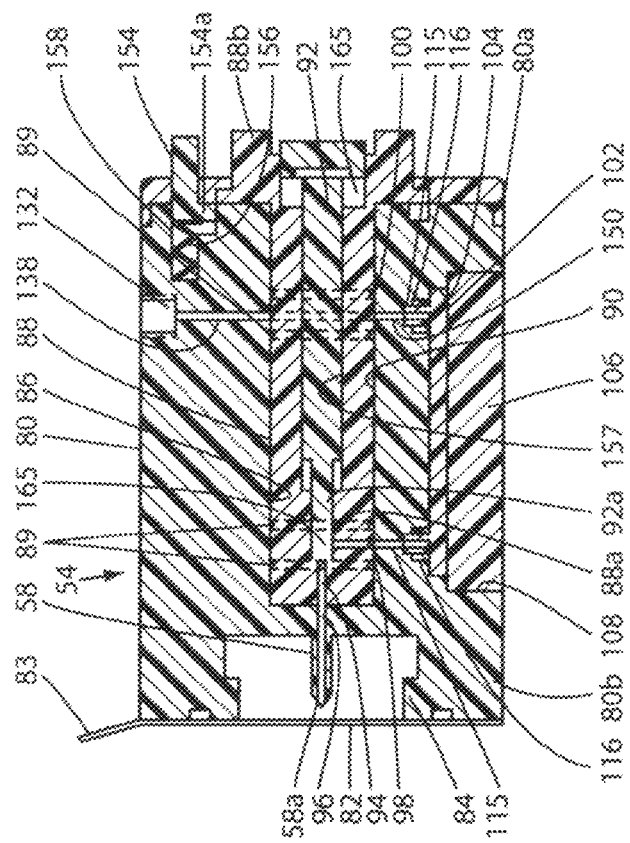
FIG. 8 is a longitudinal cross-sectional view of the second stand-alone component shown in FIGS. 4, 5 and 6 of the drawings.

Referring to the drawings and particularly to FIGS. 1 through 8, one form of the two part fluid dispensing apparatus of the present invention for dispensing medicaments is there shown. The dispensing apparatus, which is generally designated in FIGS. 1, 1A and 8A by the numeral 50, comprises two stand-alone, interconnectable assemblies 52 and 54. As best seen in FIG. 7 of the drawings, assembly 52 comprises a fluid reservoir assembly that houses a fluid reservoir defining component 56 having an outlet 56a. As illustrated in FIG. 8 of the drawings, assembly 54 comprises a fluid delivery and control assembly that includes a penetrating member 58 and a novel fluid flow control means that functions to control the flow of medicinal fluid toward the patient.

Figure 16:
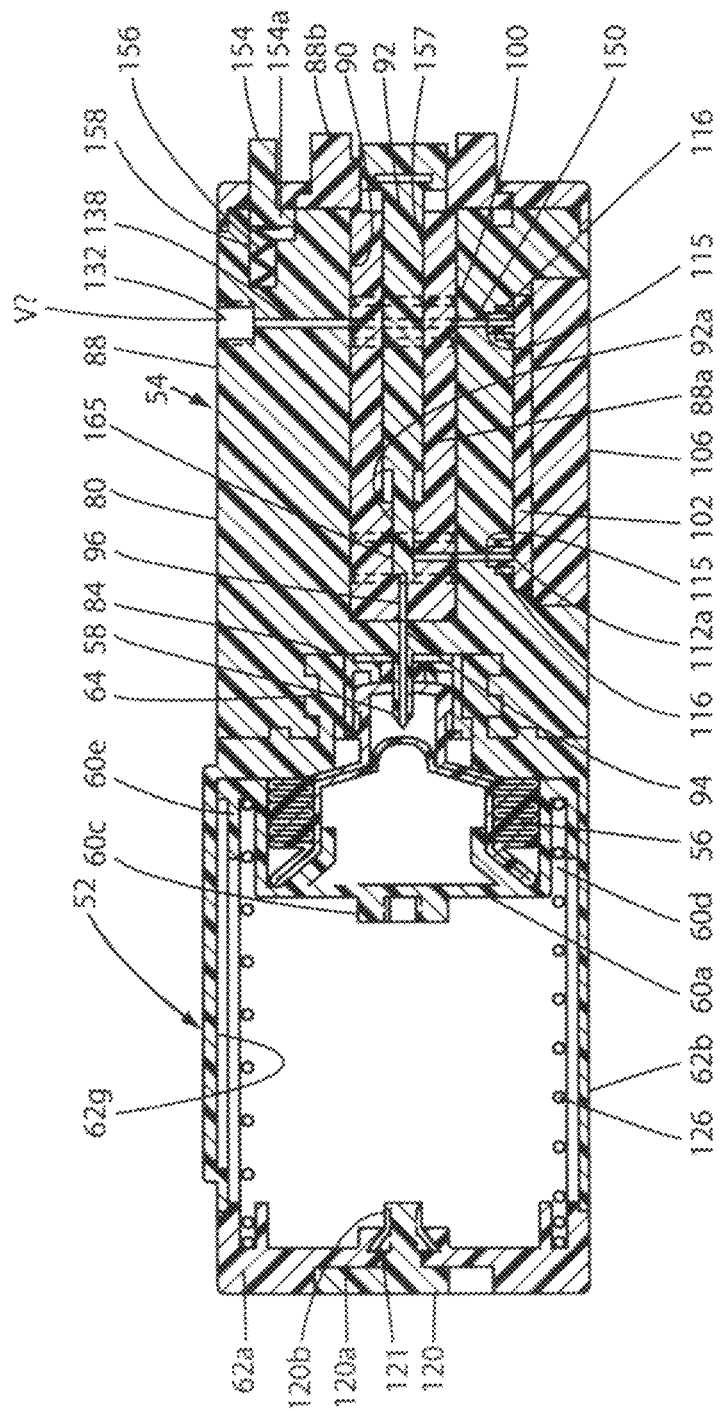
FIG. 16 is a longitudinal cross-sectional view of the fluid dispensing apparatus of the invention shown in FIG. 1, wherein the first and second stand-alone components of the invention have been operably interconnected.

Considering first the unitary fluid reservoir assembly 52, in addition to the reservoir defining component 56, this assembly includes a carriage 60 and a stored energy means that is operably associated with the carriage for moving the carriage between a first retracted position shown in FIG. 7 and a second advanced position shown in FIG. 16. As best seen by referring to FIG. 7, carriage 60 includes a base 60a, a reservoir receiving flange 60b, a carriage locking member receiving protuberance 60c and a stored energy means receiving skirt 60d which receives the novel stored energy means of the invention. Carriage 60 is releasably locked in its first position by a novel carriage locking means, the character of which will be described in the paragraphs which follow.

The reservoir defining component 56, the carriage 60 and a stored energy means are all housed within a generally cylindrically shaped housing 62 that includes a base 62a, an outer wall 62b and a front wall 62c. Connected to front wall 62c is an externally threaded connector neck 64. Connector neck 64 is closed by a first cover shown here as a first sterile barrier 64a that is removably connected to the connector neck in the manner shown in FIG. 7 of the drawings. Sterile barrier 64a, which includes a pull tab 65, here comprises a thin membrane constructed from any suitable polymer.

Figure 11:
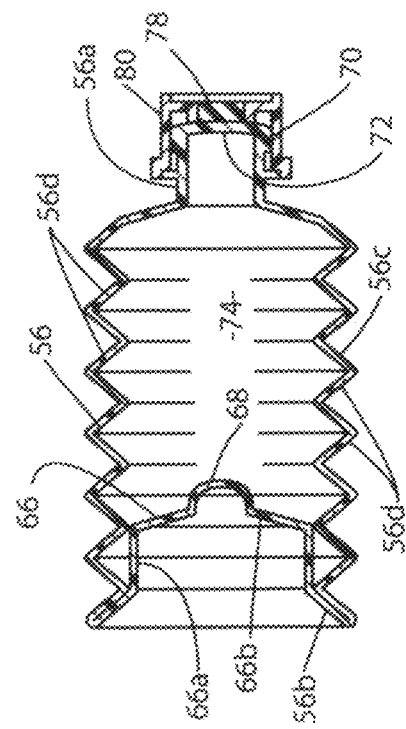
FIG. 11 is a cross-sectional view taken along lines 11-11 of FIG. 10.
Figure 13:
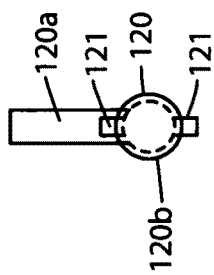
FIG. 13 is a front view of one form of the carriage locking member of the first stand-alone component of the invention.

As best seen in FIG. 11, reservoir defining component 56 here comprises an integrally formed, hermetically sealed container that includes a front portion 56a, a rear portion 56b and a collapsible accordion-like, continuous, uninterrupted side wall 56c that interconnects the front and rear portion of the container. As illustrated in the drawings, the accordion like side wall 56c comprises a multiplicity of adjacent generally "V" shaped interconnected folds, 56d. Rear portion 56b of the container includes an inwardly extending ullage segment 66 having a side wall 66a and an end wall 66b. As illustrated in FIGS. 7 and 11, end wall 66b includes a generally hemispherical shaped protuberance 68. Front portion 56a of the container includes an integrally formed neck 70 having a closure wall 72. Front portion 56a, rear portion 56b and side wall 56c cooperate to define the fluid reservoir 74 of the fluid reservoir assembly 52.

Reservoir defining component 56 is constructed in accordance with aseptic blow-fill seal manufacturing techniques the character of which is well understood by those skilled in the art. Basically, this technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding and then filling the molded container in a sterile fashion. Following the molding, filling and sealing of the container, it is sterilized at high temperature in a manner well understood by those skilled in the art. Unlike chemical or gamma ray sterilization, this temperature sterilization step has no adverse effect on the medicament contained within the container reservoir.

Containers for use in dispensing beneficial agents in specific dosages such as the unidose reservoir assembly of the present invention, present unique requirements. More particularly, it is important that as much of the beneficial agents contained within the reservoir assembly be dispensed from a container to avoid improper dosage, waste and undue expense. Accordingly the previously identified ullage segment functions to fill the interior space of the collapsible container when it is collapsed in the manner shown in FIG. 16 of the drawings.

Figure 12:
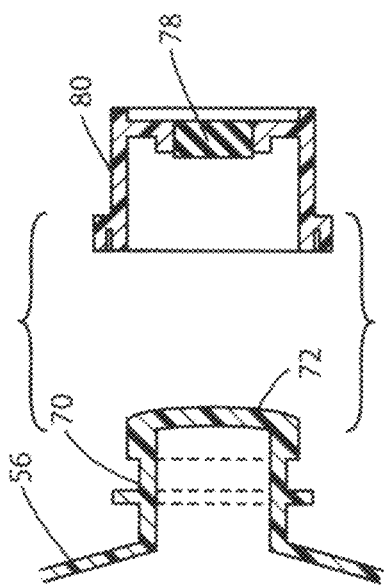
FIG. 12 is an enlarged, fragmentary cross-sectional view of the forward portion of the fluid reservoir shown in FIG. 11.

In a manner presently to be described, fluid medicament reservoir 74 of the fluid reservoir assembly 52 is accessible via a penetrating member 58 which forms the inlet to the fluid delivery and control assembly 54. More particularly, penetrating member 58 is adapted to pierce closure wall 72 as well as a pierceable membrane 78 (FIGS. 7, 11 and 12) which is secured in position over closure wall 72 by means of a closure cap 80 which is affixed to the neck portion 70 of reservoir defining assembly 56 (FIG. 11). As previously described, the reservoir defining assembly 56 is formed using the earlier described aseptic blow fill technique and the reservoir portion of the container is sealed by the thin closure wall 72. Prior to heat sterilization of the container, the piercable membrane 78 is positioned over the closure wall and the closure cap 80 is positioned over the piercable membrane and is secured to the neck portion 70 by any suitable means such as adhesive bonding, sonic welding or heat welding.

Considering now the second assembly 54 of the fluid dispensing apparatus, which is illustrated in FIGS. 4, 5, 6 and 8, this assembly comprises a generally cylindrically shaped housing 80 having a forward portion 80a and a rearward portion 80b. Rearward portion 80b which is covered by a cover, here shown as a second sterile barrier 82 having a pull tab 83, includes an internally threaded cavity 84. Second sterile barrier 82, which is removably connected as by bonding to rearward portion 80b in the manner shown in FIG. 8 of the drawings, here comprises a thin membrane constructed from any suitable polymer.

As illustrated in FIG. 8 of the drawings, housing 80 includes a longitudinally extending bore 86 that rotatably receives the rate control housing 88 of the second assembly 54. Rate control housing 88, which forms a part of the flow control means of the invention, includes an elongated body portion 88a and a forwardly extending finger engaging portion 88b. A plurality of longitudinally spaced apart O-rings 89, which circumscribe body portion 88a, function to prevent fluid leakage between housing 80 and the body portion 88a of the rate control housing. Elongated body portion 88a is also provided with a longitudinally extending bore 90 that slidably receives a disabling shaft 92, the construction and operation of which will presently be described.

As illustrated in FIG. 8, body portion 88a is also provided with a longitudinally extending fluid passageway 94 that communicates with the flow passageway 58a of the previously identified piercing member 58 via a passageway 96 provided in housing 80. For a purpose presently to be described, body portion 88a is also provided with a pair of longitudinally spaced fluid flow passageways 98 and 100.

Fluid flow passageway 98 comprises an inlet passageway that communicates with a rate control assembly 102 that is mounted within a cavity 104 provided in a housing 80. Rate control assembly 102, which also forms a part of the flow control means of the invention, is maintained within cavity 104 by a rate control cover 106, which also forms a part of the flow control means of the invention. As best seen in FIG. 8 of the drawings, rate control cover 106 is disposed within a cavity 108 formed in housing 80.

As previously mentioned, since assembly 54 comprises a stand alone, unitary assembly containing no medicinal fluids, it can be sterilized in the preferred manner by irradiating it with gamma-rays.

As best seen in FIGS. 18 through 22, rate control assembly 102 comprises a rate control plate 110, which as shown in FIG. 23 is provided with a serpentine micro-channel 112 having an inlet 112A and an outlet 112b which communicates with passageway 100 that comprises an outlet passageway. The length, width and depth of the micro-channel determine the rate at which the fluid will flow toward outlet 112b. A thin cover 114 covers the channel in the manner shown in FIG. 18. When assemblies 52 and 54 are interconnected in the manner shown in FIG. 16, inlet 112A is in communication with penetrating member 58 via an outlet tube 115 that is received within and positioned by an upstanding collar 116 provided on rate control plate 110, via passageway 98, via passageway 94 and via passageway 96 (FIG. 8). Because the second assembly has been sterilized in the manner previously described, these passageways are completely sterile at the time assembly 54 is connected to assembly 52.

In using the apparatus of the invention, the first step is to remove the sterile covers 64a and 82 from assemblies 52 and 54. This done, the assemblies can be irreversibly interconnected in the manner illustrated in FIG. 8A by inserting the externally threaded neck 64 of assembly 52 into internally threaded cavity 84 of assembly 54 and rotating assembly 52 relative to assembly 54. As the assemblies mate, penetrating member 58 will penetrate elastomeric member 78 and closure wall 72 of the container.

Figure 9:
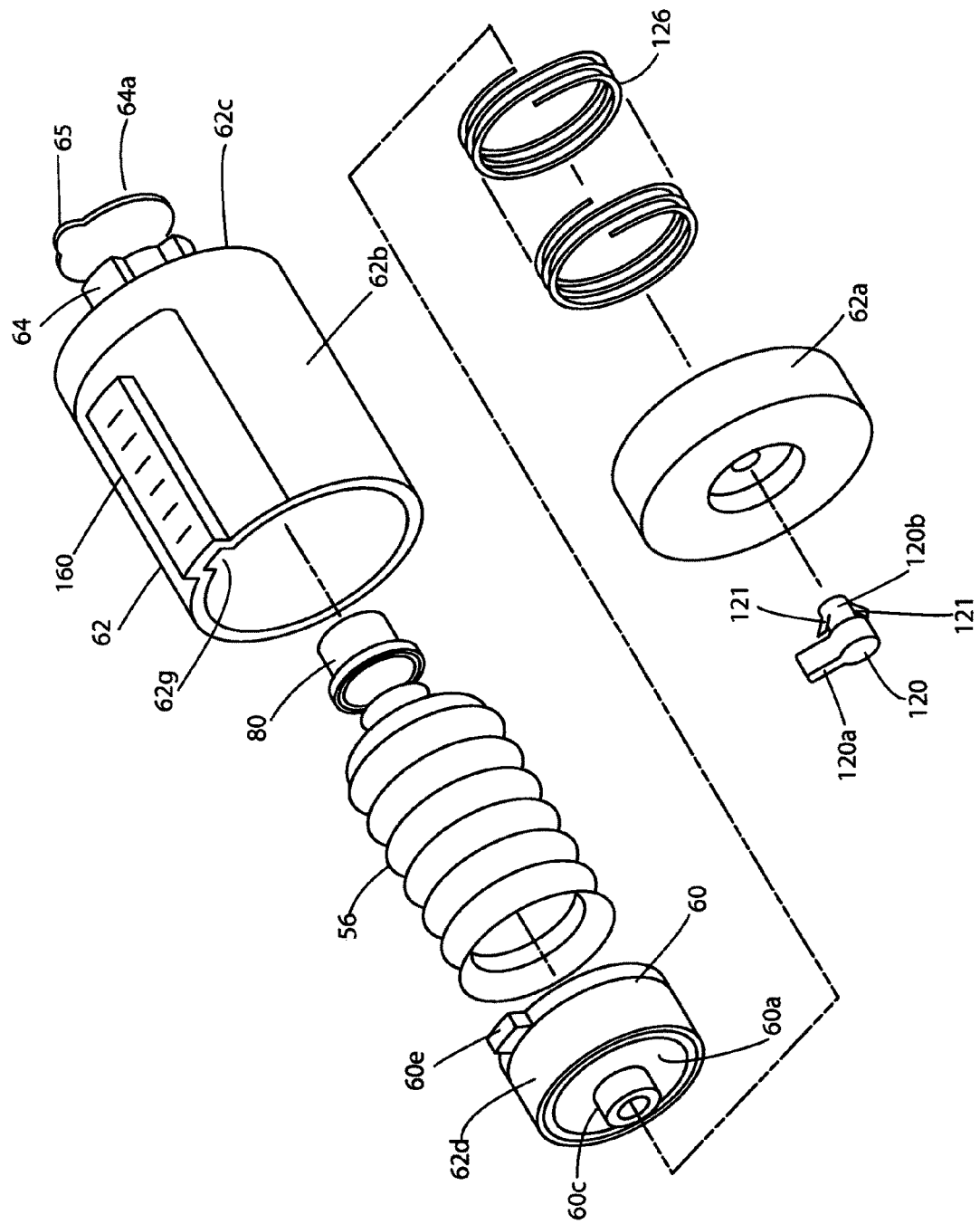
FIG. 9 is a generally perspective, exploded view of the first stand-alone component shown in FIGS. 2 and 3.
Figure 10:
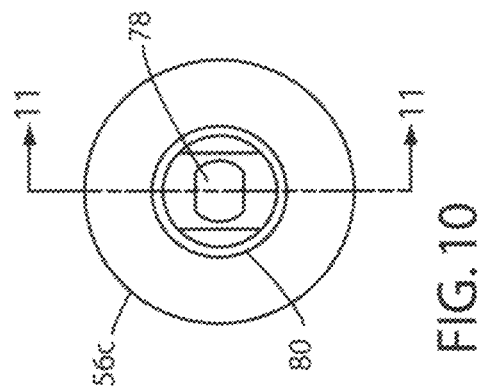
FIG. 10 is a front view of one form of the collapsible fluid reservoir of the first stand-alone component of the invention.
Figure 14:
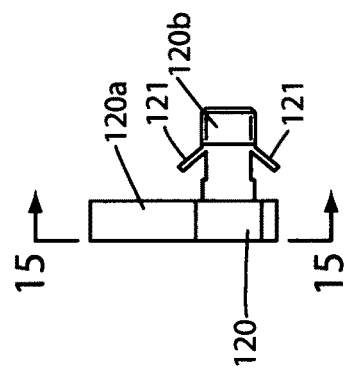
FIG. 14 is a cross-sectional view taken along lines 14-14 of FIG. 13.
Figure 15:
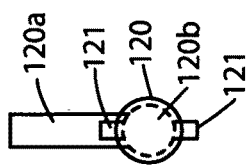
FIG. 15 is a view taken along lines 15-15 of FIG. 14.

With communication between the fluid reservoir 74 and the internal fluid passageway 58a of the penetrating member 58 having thusly been established, the fluid contained within the fluid reservoir can be expelled from the reservoir 74 by rotating the carriage release member 120 which comprises a part of the previously identified carriage locking means. This is accomplished by grasping the finger engaging arm 120A of the release member (FIG. 14) and rotating the member in the manner indicated in FIG. 2 until the threaded shank 120b of the knob threadably disengages from the locking member receiving protuberance 60c. Release member 120 is held in position within housing base 62a by means of circumferentially spaced locking tabs 121 provided on shank 120b. Once the carriage release member is free from the locking member receiving protuberance, the stored energy means, here shown as a coil spring 126 that is movable from the first compressed position shown in FIG. 7 to a second extended position shown in FIG. 16, will urge the carriage forwardly in the manner illustrated in FIG. 16 of the drawings. As the carriage moves forwardly, the circumferentially spaced guide tabs 60e formed on the carriage (FIG. 9) will slide within and be guided by guide channel 62g formed in housing 62 (FIG. 7). As the accordion side walls collapse, the fluid will be forced outwardly of the reservoir into internal passageway 58a of the penetrating member. In the manner previously described, the fluid will then flow toward the fluid flow control means of the invention, which functions to control the flow of fluid from the fluid reservoir of the fluid delivery portion of the device toward the patient.

To enable the fluid to flow from the reservoir 74 to the patient via the administration set 130 (FIG. 8A), the fluid control locking means must be operated in the manner presently to be described.

Figure 8A:
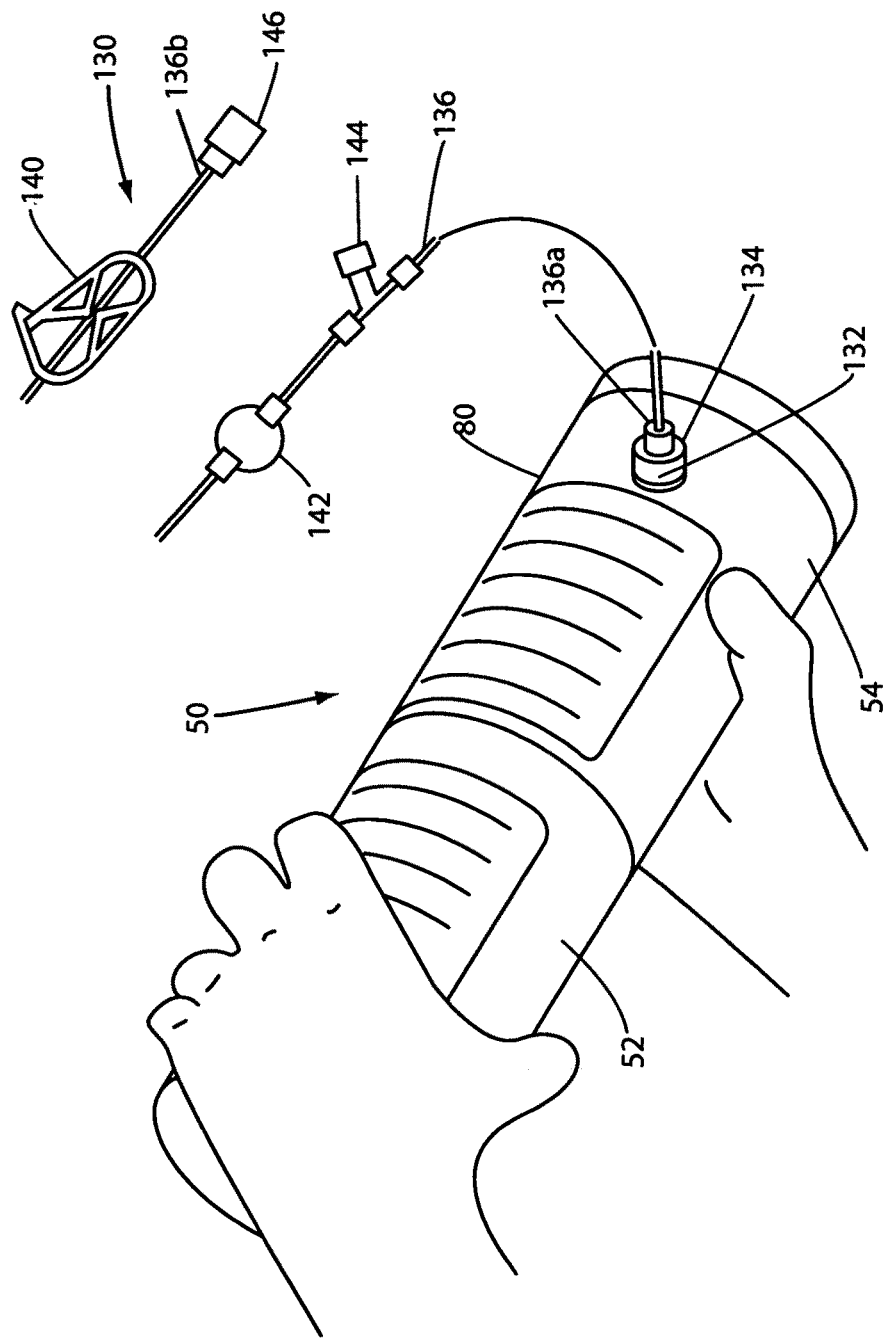
FIG. 8A is a generally perspective, diagrammatic view illustrating the assembly of the two parts of the two-part fluid delivery system of the invention.

As shown in FIG. 8A of the drawings, the administration set 130 is sealably interconnected with an outlet port 132 formed in housing 80. More particularly, the administration set 130 is connected to housing 80 by means of a connector 134 so that the proximal end 136a of the administration line 136 is in communication with an outlet fluid passageway 138 formed in housing 80 (see FIG. 8). Disposed between the proximal end 136a and the distal end 136b of the administration line are a conventional clamp 140, a conventional gas vent and filter 142, and a generally Y-shaped injector site, generally designated by the numeral 144. A luer connector 146 of conventional construction is provided at the distal end 136b of the administration line.

Figure 17:
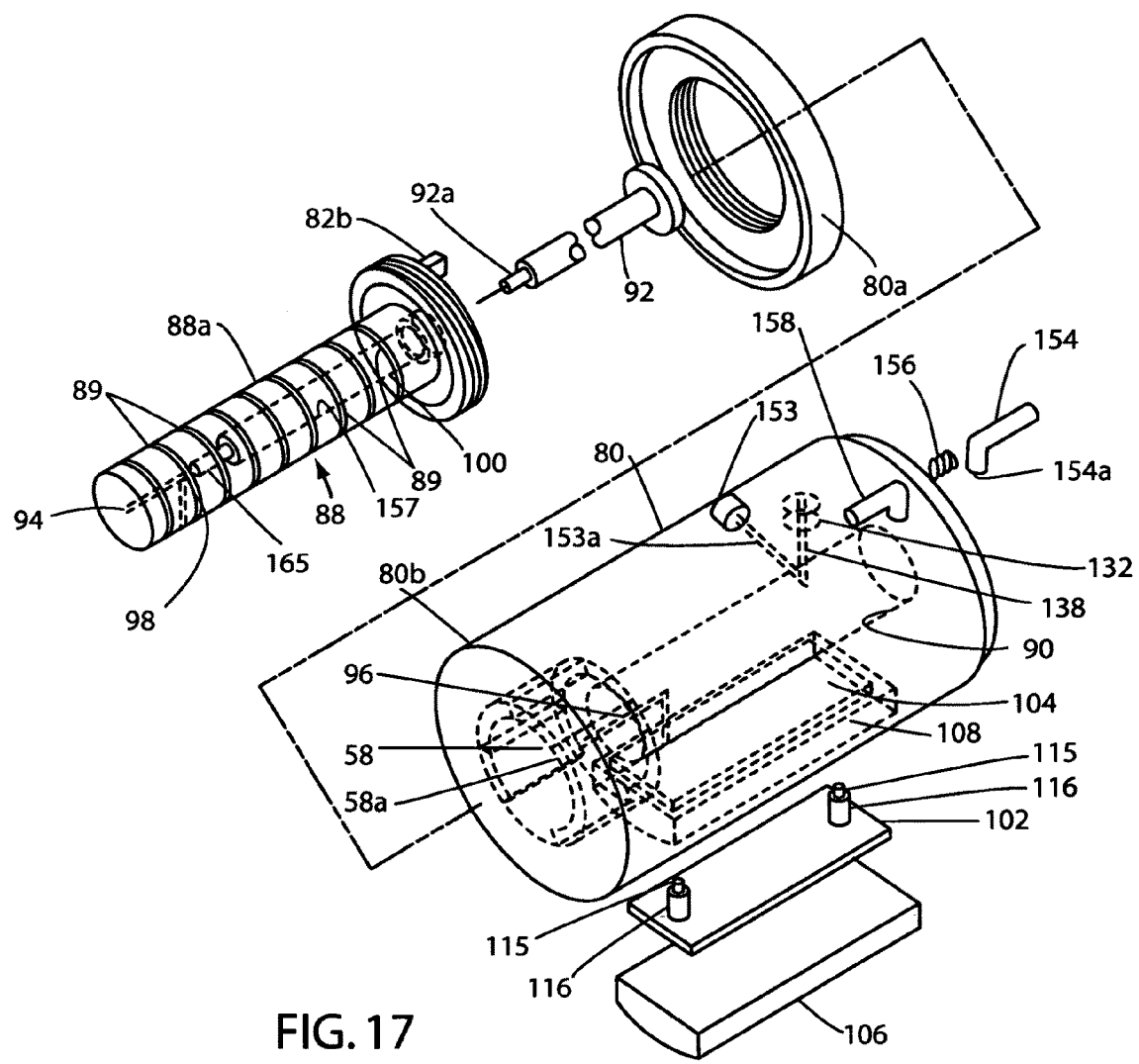
FIG. 17 is a generally perspective, exploded view of the second stand-alone component shown in FIGS. 4, 5 and 6.
Figure 29:
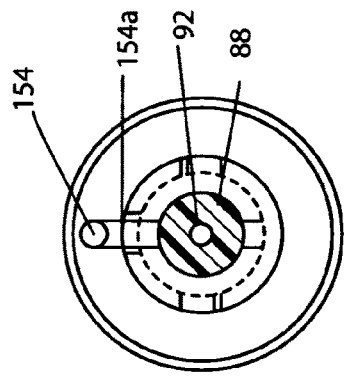
FIG. 29 is a rear view of the second stand-alone component of the invention.

To permit fluid flow from the outlet 112b of the rate control micro-channel 112 toward passageway 138, the rate control housing 88 must be rotated to a position wherein flow passageway 100 aligns with a flow passageway 150 formed in housing 80 (FIG. 8) and also with outlet passageway 138. Since passageway 150 is in communication with outlet 112b of the rate control channel, fluid can flow through the micro-channel at a controlled, fixed rate depending upon the configuration of the channel, into passageway 150, then into passageway 100, then through the rate control housing and finally into passageway 138. From passageway 138 the fluid will flow into the inlet of the administration set for delivery to the patient at a predetermined fixed rate. During the fluid delivery step any gases contained within the device reservoir and the various fluid passageways are vented to atmosphere via vent port 153 and passageway 153a (FIG. 17).

Figure 26:
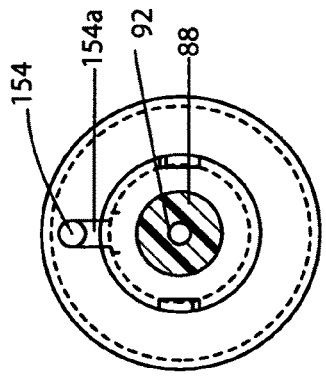
FIG. 26 is a rear view of the second stand-alone component of the invention.
Figure 27:
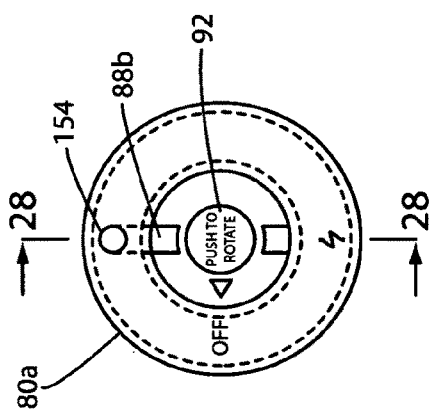
FIG. 27 is a front view of the second stand-alone component of the invention is illustrating the operation of the disabling mechanism.
Figure 24:
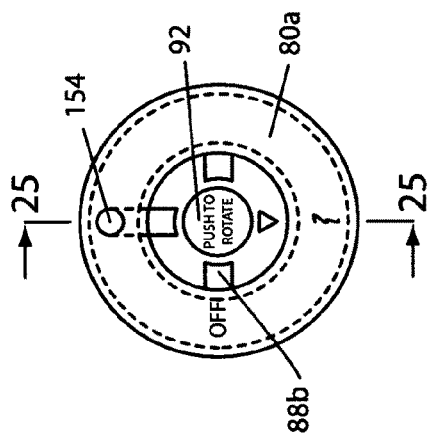
FIG. 24 is a front view of the second stand-alone component of the invention is illustrating the operation of the locking plunger of the device to accomplish the fluid dispensing step.
Figure 28:
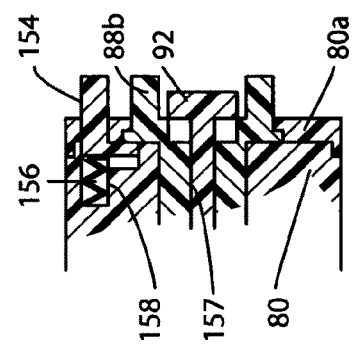
FIG. 28 is a fragmentary cross-sectional view taken along lines 28-28 of FIG. 27.
Figure 25:
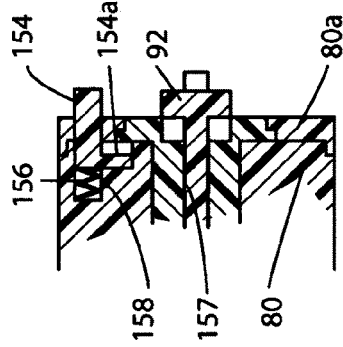
FIG. 25 is a fragmentary cross-sectional view taken along lines 25-25 of FIG. 24.

As previously mentioned, rotation of the rate control housing 88 cannot be accomplished until the rate control locking means is operated by the caregiver. In the present form of the invention this rate control locking means comprises a plunger 154 that includes a locking finger 154a (FIG. 17) that prevents rotation of the rate control housing, unless and until the plunger is moved inwardly of the housing against the urging of a biasing means shown here as coil spring 156 that is housed within a chamber 158 formed in housing 80. Once the plunger is appropriately urged inwardly, rate control housing 88 can be rotated into the correct fluid flow position by grasping rotation fingers 88b and imparting a rotational force to the rotating fingers (see also FIGS. 24, 25 and 26).

Referring to FIGS. 2 and 3, it is to be noted that a reservoir viewing window 160 is provided in housing 62 so that the remaining amount of fluid contained within reservoir 74 can be viewed. Additionally, fluid level indicating indicia 162 are provided on housing 62, proximate window 160 so that the fluid remaining within the reservoir can be accurately monitored by the caregiver.

Fluid flow from the reservoir 74 toward the rate control assembly via passageway 98 can be prevented through operation of the disabling means of the invention. This important disabling means, which is illustrated in FIGS. 8 and 27 through 29, comprises the previously identified disabling shaft 92. As indicated in the drawings, when the disabling shaft 92 is pushed inwardly from the position shown in FIG. 8 into an inward position, wherein it resides within a cavity 157 provided in housing 88, the forward portion 92a of the disabling shaft will move into a cavity 165 formed in rate control housing 88, thereby blocking fluid flow from the internal passageway 58a of the penetrating member into passageway 98. By stopping fluid flow in this manner, the apparatus is substantially safely disabled until the disabling shaft 92 is once again returned to the starting position shown in FIG. 8 of the drawings.

Figure 32:
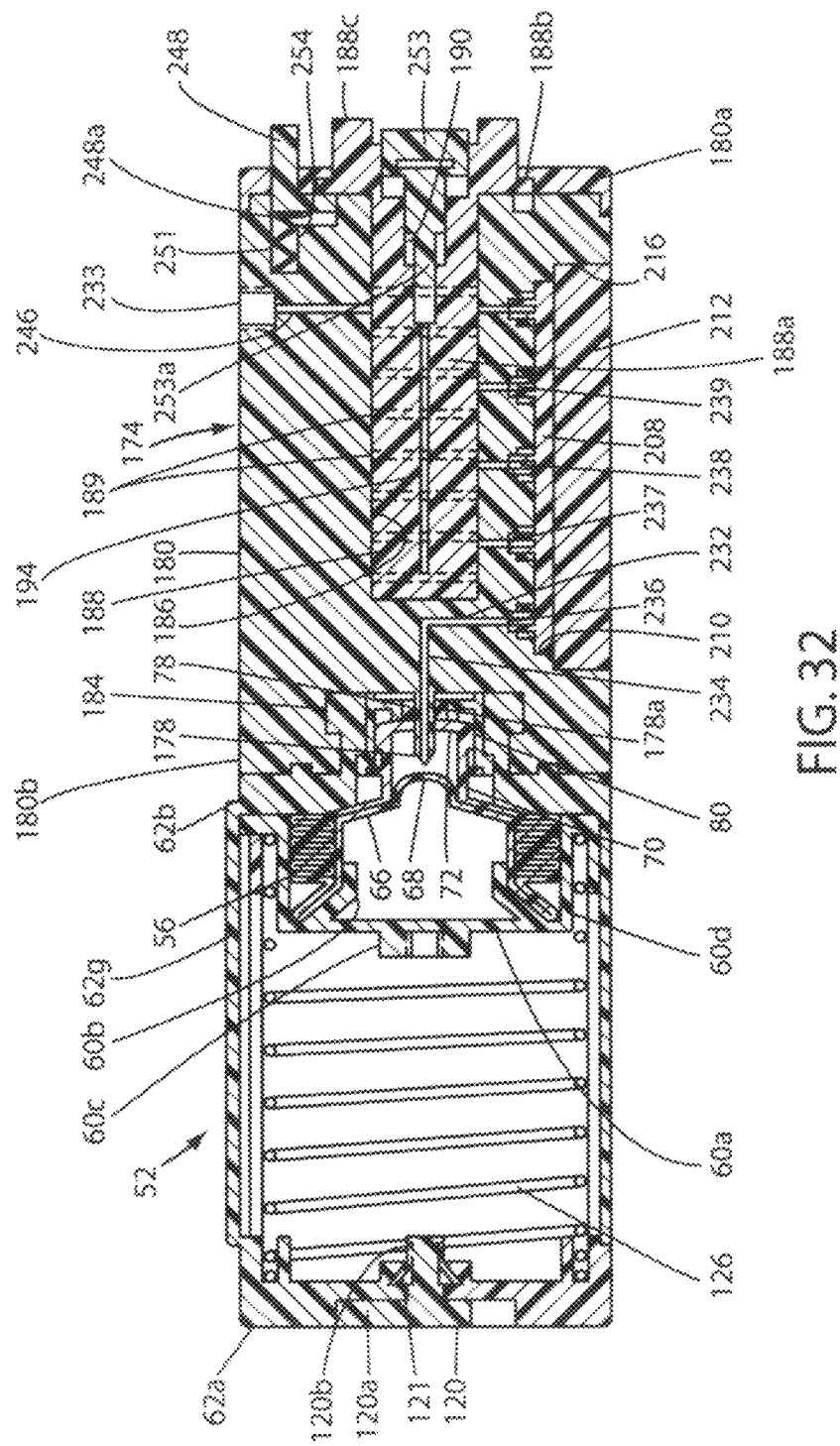
FIG. 32 is a longitudinal cross-sectional view of the fluid dispensing apparatus of the invention shown in FIG. 1 wherein the first and second stand-alone components of the invention have been operably interconnected.

Referring now to FIGS. 30, 31 and 32, an alternate form of the two part fluid dispensing apparatus of the present invention for dispensing medicaments is there shown. This alternate form of dispensing apparatus, which is generally designated in FIG. 32 by the numeral 174, is similar in many respects to the embodiment of the invention illustrated in FIGS. 1 through 29 and like numerals are used in FIGS. 30, 31 and 32 to identify like components. As before, the dispensing apparatus here comprises two stand-alone, interconnectable assemblies 52 and 174. As indicated in FIG. 30, first assembly 52 is substantially identical in construction and operation to the previously described first assembly and comprises a fluid reservoir assembly that houses a fluid reservoir defining component 56. Assembly 174 is also somewhat similar to the previously described assembly 54 and comprises a fluid delivery and control assembly that includes a penetrating member 178 and a novel fluid flow control means that functions to control the flow of medicinal fluid toward the patient. The primary difference between second assembly 174 and the previously described assembly 54 resides in the provision of a differently constructed rate control assembly that permits the delivery of fluid to the patient at a plurality of selected rates of flow.

As in the earlier described embodiment of the invention, reservoir defining component 56 is constructed in accordance with aseptic blow-fill seal manufacturing techniques. Following molding, filling in the sealing, the reservoir defining component is sterilized at a relatively high temperature.

In a manner presently to be described, fluid medicament reservoir 74 of the fluid reservoir assembly 52 is accessible via the previously identified penetrating member 178 which forms to inlet to the fluid delivery and control assembly 174. More particularly, penetrating member 178 is adapted to pierce closure wall 72 as well as a pierceable membrane 78 (FIG. 32) which is positioned over closure wall 72 of by means of a closure cap 80 that is affixed to the neck portion 70 of reservoir defining assembly 56 (FIG. 11).

Figure 33:
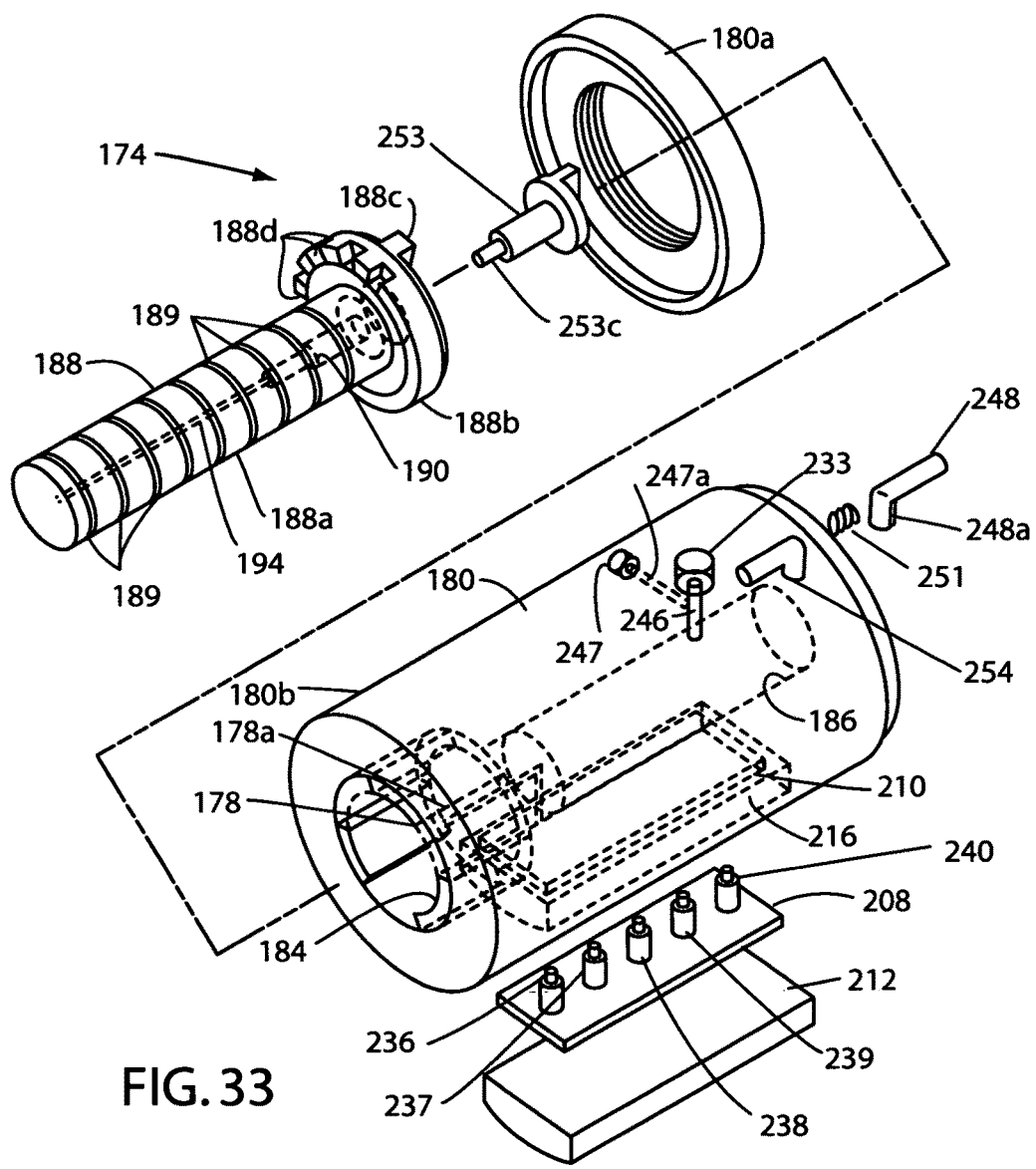
FIG. 33 is a generally perspective, exploded view of the alternate second stand alone component shown in FIGS. 4, 5 and 6.

Considering now the second assembly 174 of this latest form of the fluid dispensing apparatus which is illustrated in FIGS. 31, 33 and 37, this assembly comprises a generally cylindrically shaped housing 180 having a forward portion 180a and a rearward portion 180b. Rearward portion 180b, which is sealed by a second hermetically affixed sterile barrier 182 having a pull tab 183, includes an internally threaded cavity 184. Second sterile barrier 182, which is removably connected to rearward portion 180b in the manner shown in FIGS. 31 and 37 of the drawings, here comprises a thin membrane constructed from any suitable polymer.

As illustrated in FIGS. 31, 33 and 37 of the drawings, housing 180 includes a longitudinally extending bore 186 that rotatably receives the rate control housing 188 of the second assembly 174. Rate control housing 188, which forms a part of the flow control means of this latest embodiment of the invention, includes an elongated body portion 188a, forward flange 188b and a forwardly extending finger engaging portion 188c that is connected to and extends forwardly of flange 188b. For a purpose presently to be described, a plurality of circumferentially spaced apart channels, or cavities, 188d are formed on the rear face of flange 188b. Additionally, a plurality of longitudinally spaced apart O-rings 189, which circumscribe body portion 188a, function to prevent fluid leakage between housing 180 and the body portion 188a of the rate control housing as the rate control housing is rotated. Elongated body portion 188a is also provided with a longitudinally extending bore 190 that slidably receives the rearward portion of a disabling shaft 253, the construction and operation of which will presently be described.

As illustrated in FIGS. 31, 37 and 38, body portion 188a is also provided with a longitudinally extending fluid passageway 194 that communicates with the flow passageway 178a of the previously identified piercing member 178 via the flow rate control means. For a purpose presently to be described, body portion 188a is also provided with a plurality of forwardly positioned, circumferentially spaced apart, radially extending outlet fluid flow passageways 198, 200, 202 and 204 that communicate with longitudinally extending, central passageway 194 (FIGS. 41, 42 and 43).

In a manner presently to be described, a plurality of longitudinally spaced apart, radially extending inlet fluid flow passageways 199, 201, 203 and 205 (FIG. 42) also communicate with fluid passageway 194 and as the rate control housing 188 is rotated, selectively communicate with a rate control assembly 208 (FIG. 34) that is mounted within a cavity 210 provided in a housing 180 (FIG. 37). Rate control assembly 208, which also forms a part of the flow control means of this latest form of the invention, is maintained within cavity 210 by a rate control cover 212, which also forms a part of the flow control means of the invention. As best seen in FIG. 33 of the drawings rate control cover 212 is disposed within a cavity 216 formed in housing 180.

Turning to FIGS. 34 through 36, it can be seen that rate control assembly 208 comprises a rate control plate 220, which as shown in FIG. 36 is provided with a plurality of spaced apart, serpentine micro-channels 222, 224, 226 and 228. Each of the micro-channels is of a different width, depth and length and each has an inlet in communication with an elongated passageway 230, which, in turn is in communication with the internal passageway 178a of the penetrating member 178 via a pressure regulator 231, and via passageways 232 and 234 formed in housing 180 (see FIG. 37). A thin cover 235 covers the channels in the manner shown in FIG. 34.

When assemblies 52 and 174 are interconnected in the manner shown in FIG. 32, elongated passageway 234 is in communication with penetrating member 178 via a connector collar 236 provided on rate control plate 220, via passageway 232 and via passageway 234 (FIG. 37).

In using the apparatus of the invention, the first step is to remove the sterile covers 64a and 182 from assemblies 52 and 174. This done, the assemblies can be interconnected by inserting the externally threaded neck 64 of assembly 52 into internally threaded cavity 184 of assembly 174 and rotating assembly 52 relative to assembly 174. As the assemblies are mated, penetrating member 178 will penetrate elastomeric member 78 and closure wall 72 of the container.

With communication between the fluid reservoir 74 and the internal passageway 178a of the penetrating member 178 having thusly been established, the fluid contained within the fluid reservoir can be expelled from the reservoir 74 by rotating the carriage release member 120 in the manner previously described. Once the carriage release member is free from the locking member receiving protuberance, the stored energy means, here shown as a coil spring 126 that is movable from the first compressed position to the second extended position, will urge the carriage forwardly. As the carriage moves forwardly, the accordion side walls of the container collapse causing the fluid to be forced outwardly of the reservoir into internal passageway 178a of the penetrating member. The fluid will then flow toward passageway 230 of the rate control plate 220 via the pressure regulator 231. From the pressure regulator, which controllably adjusts the pressure of the fluid flowing therefrom, the fluid will flow into and fill each of the micro-channels 222, 224, 226 and 228 that are interconnected with passageway 230 in the manner shown in FIG. 36.

To enable the fluid to flow from the reservoir 74 to the patient via the administration set 130 (FIG. 8A) that can be connected to the outlet port 233 of housing 180 (FIG. 33), the fluid control locking means of this latest form of the invention must be operated. More particularly to permit fluid flow selectively from the outlets 222a, 224a, 226a, and 228a, respectively, of the differently configured micro-channels (FIG. 36), the rate control housing 188 must be controllably rotated in a manner to selectively align the radially extending passageways 199, 201, 203 and 205 (FIG. 39) with the longitudinally spaced apart flow passageways 237, 238, 239 and 240 formed in housing 180 (FIG. 37). Since passageways 237, 238, 239 and 240 are in communication with microchannel outlets 222a, 224a, 226a, and 228a, respectively, of the differently configured micro-channels, fluid can flow from the selected micro-channel toward the selected flow passageway 237, 238, 239 or 240 at a controlled rate that depends upon the configuration of the particular channel selected. From the selected flow passageways 237, 238, 239 and 240, fluid will flow through one of the selected longitudinally spaced apart radially extending passageways formed in the rate control housing. From this selected passageway (shown in FIG. 39 as passageway 199) the fluid will flow into passageway 194 and then into passageway 246 formed in housing 180. From passageway 237 the fluid flows at the selected flow rate into the inlet of the administration set for delivery to the patient at the selected rate. As in the earlier described embodiment, any gases trapped in the device reservoir and in the various fluid passageways will be vented to atmosphere via a vent port 247 and passageway 247a (FIG. 33).

As in the earlier described embodiment of the invention, rotation of the rate control housing 188 cannot be accomplished until the rate control locking means is operated by the caregiver. In this latest form of the invention the rate control locking means comprises a plunger 248 that includes a locking finger 248a (FIG. 37) that prevents rotation of the rate control housing, unless and until the plunger is moved inwardly of the housing against the urging of a biasing means shown here as coil spring 251 that is housed within a chamber 254 formed in housing 180. Once the plunger is appropriately urged inwardly and removed from the channels 188d formed in flange 188b, rate control housing 188 can be rotated into the desired fluid flow position by grasping rotation fingers 188c and imparting a rotational force thereto. Referring particularly to FIGS. 37 and 42, it is to be noted that as the rate control housing is rotated, spring 251 continuously urges locking finger 248a into a selected locking channel 188d formed in flange 188b. When the locking finger is seated within a particular locking channel, one of the radially extending passageways formed in the rate control housing (here shown as passageway 194) will be locked in communication with one of the outlets of one of the plurality of micro channels formed in the rate control plate in the fluid will flow through the selected micro channel toward the patient at a selected fixed-rate. When it is desired to once again create a fluid flow toward the patient, the plunger 248 must once again be depressed and the rate control housing rotated into another position.

As in the earlier described embodiment of the invention, a reservoir viewing window 160 is provided in housing 62 so that the amount of fluid contained within reservoir 74 can be viewed. Additionally, fluid level indicia 162 are provided on housing 62, proximate window 160, so that the fluid remaining within the reservoir can be accurately monitored by the caregiver.

Fluid flow from the reservoir 74 toward the rate control assembly of the second assembly 174 via passageway 236 can be prevented through operation of the disabling means of the invention. This important disabling means, which is of a similar construction and operation to that earlier described, comprises a disabling shaft 253. As indicated in FIG. 37 of the drawings, when the disabling shaft 253 is pushed inwardly from the position shown in FIG. 37 into an inward position, wherein it resides within a cavity 255 provided in housing 188, the forward portion 253a of the disabling shaft will move into a position where it blocks fluid flow from passageway 194 toward passageway 246 so as to stop fluid flow toward the administration set. By stopping fluid flow in this manner, the apparatus is substantially disabled until the disabling shaft 253 is once again returned to the starting position shown in FIG. 37 of the drawings.

Turning next to FIGS. 41 through 43, still another form of the two part fluid dispensing apparatus of the present invention for dispensing medicaments is there shown. This second, alternate, form of dispensing apparatus is similar in many respects to the earlier described embodiments of the invention and like numerals are used in FIGS. 44 through 47 to identify like components. As before, dispensing apparatus 174 comprises two stand-alone, interconnectable assemblies of the character shown in FIGS. 44 and 47. As indicated in FIG. 44, first assembly 252 is of a somewhat different construction, while second assembly 54 is substantially identical in construction and operation to the previously described second assembly 54. The primary difference between first assembly 252 and the previously described assembly 52 resides in the provision of a totally different stored energy means for moving a somewhat differently configured carriage 264 from a first retracted position to a second advanced position. Second assembly 54 includes a rate control assembly that permits the delivery of fluid to the patient at substantially a fixed rate The reservoir defining component 56 of this latest form of the invention is quite similar in construction and operation to the previously described and is constructed in accordance with aseptic blow-fill seal manufacturing techniques the character previously described. Following molding, filling and sealing the reservoir defining component is sterilized at a relatively high temperature.

In a manner presently to be described, fluid medicament reservoir 74 of the fluid reservoir assembly 252 is accessible via the penetrating member 58 of the fluid delivery and control assembly 54. More particularly, penetrating member 58 is adapted to pierce closure wall 72 as well as a pierceable membrane 78 (FIG. 44) which is positioned over closure wall 72 of by means of a closure cap 80 which is affixed to the neck portion 70 of reservoir defining assembly 56 (see FIG. 11).

Considering now in greater detail the first assembly 252 of this latest form of the fluid dispensing apparatus, this assembly comprises a generally cylindrically shaped housing 256 having a forward portion 256a and a rearward portion 256b. Forward portion 256a, which is sealed by a sterile barrier 258 having a pull tab 258a, includes an externally threaded neck 260 that is receivable within threaded cavity 84 of the second assembly 54.

In addition to the reservoir defining component 56, assembly 252 includes a carriage assembly 264 and a stored energy means that is operably associated with the carriage assembly for moving the carriage assembly between the first retracted position and the second advanced position. Carriage assembly 264 includes a base assembly 266 that includes a forward portion having, a base 266, a reservoir receiving flange 266b and a fluid level indicator boss 266c. Base assembly 266 also includes a rear portion having housing 266d that is provided with a threaded carriage locking member receiving cavity 266e (see also FIG. 47). mounted within the housing 273 is the important stored energy means of this latest form of the invention which here comprises a pair of constant force springs 270. Carriage assembly 264 is releasably locked in its first position by a novel carriage locking means, the character of which will be described in the paragraphs which follow.

As in the earlier described embodiments of the invention and as illustrated in FIG. 11 of the drawings, reservoir defining component 56 here comprises an integrally formed, hermetically sealed container that includes a front portion 56a, a rear portion 56b and a collapsible accordion-like, continuous, uninterrupted side wall 56c that interconnects the front and rear portion of the container. As illustrated in the drawings, the accordion like side wall 56c comprises a multiplicity of adjacent generally "V" shaped interconnected folds, 56d. Rear portion 56b of the container includes an inwardly extending ullage segment 66 having a side wall 66a and an end wall 66b. As illustrated in FIGS. 7 and 11, end wall 66b includes a generally hemispherical shaped protuberance 68. Front portion 56a of the container includes an integrally formed neck 70 having a closure wall 72. Front portion 56a, rear portion 56b and side wall 56c cooperate to define the fluid reservoir 74 of the fluid reservoir assembly 56.

Constant force springs, such as springs 270 are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. As best seen in FIGS. 44 and 47, springs 270 are mounted with one end 270a tightly wrapped on a drum 272 that is housed with a carriage block 273 and the other end 270b attached forward portion 256a of housing 256 in the manner shown in FIG. 47.

In using the apparatus of this latest form of the invention, the first step is to remove the sterile covers 258 and 82 from assemblies 252 and 54. This done, the assemblies can be interconnected by inserting the externally threaded neck 260 of assembly 252 into internally threaded cavity 84 of assembly 54 and rotating assembly 252 relative to assembly 54. As the assemblies mate, penetrating member 58 will penetrate elastomeric member 78 and closure wall 72 of the container.

With communication between the fluid reservoir 74 and the internal passageway 58a of the penetrating member 58 having thusly been established, the fluid contained within the fluid reservoir can be expelled from the reservoir 74 by rotating the carriage release member 280 which comprises a part of the previously identified carriage locking means. This is accomplished by grasping the finger engaging arm 280a of the release member (FIG. 47) and rotating the member until the threaded shank 280b of the knob threadably disengages from the locking member receiving cavity 266e. Release member 280 is held in position within base 256d by means of circumferentially spaced locking tabs 281 provided on shank 280b. Once the carriage release member is free from the locking member receiving cavity, the stored energy means, here shown as constant force springs 270, will urge the carriage assembly 266 forwardly. As the carriage moves the accordion side walls 56c of the collapsible container well collapse and the fluid will be forced outwardly of the reservoir into internal passageway 58a of the penetrating member. In the manner previously described, the fluid will then flow toward the fluid flow control means of assembly 54, which functions to control the flow of fluid from the fluid reservoir of the fluid delivery portion of the device toward the patient.

To enable the fluid to flow from the reservoir 74 to the patient via the administration set 130 (FIG. 8A), the fluid control locking means must be operated in the manner previously described in connection with the first embodiment of the invention.

Referring to FIGS. 44 and 47, it is to be noted that a reservoir viewing window 284 is provided in housing 256 so that the amount of fluid contained within reservoir 74 can be determined by viewing the advance of the fluid indicator boss 266c. Additionally, fluid level indicia 284a are provided on window 284 so that the fluid remaining within the reservoir can be accurately monitored by the caregiver.

As in the earlier described embodiments of the invention, fluid flow from the reservoir 74 toward the rate control assembly of the second assembly 54 can be prevented through operation of the disabling means of the invention in a manner previously described, which disabling means comprises the previously identified disabling shaft 92.

Figure 48:
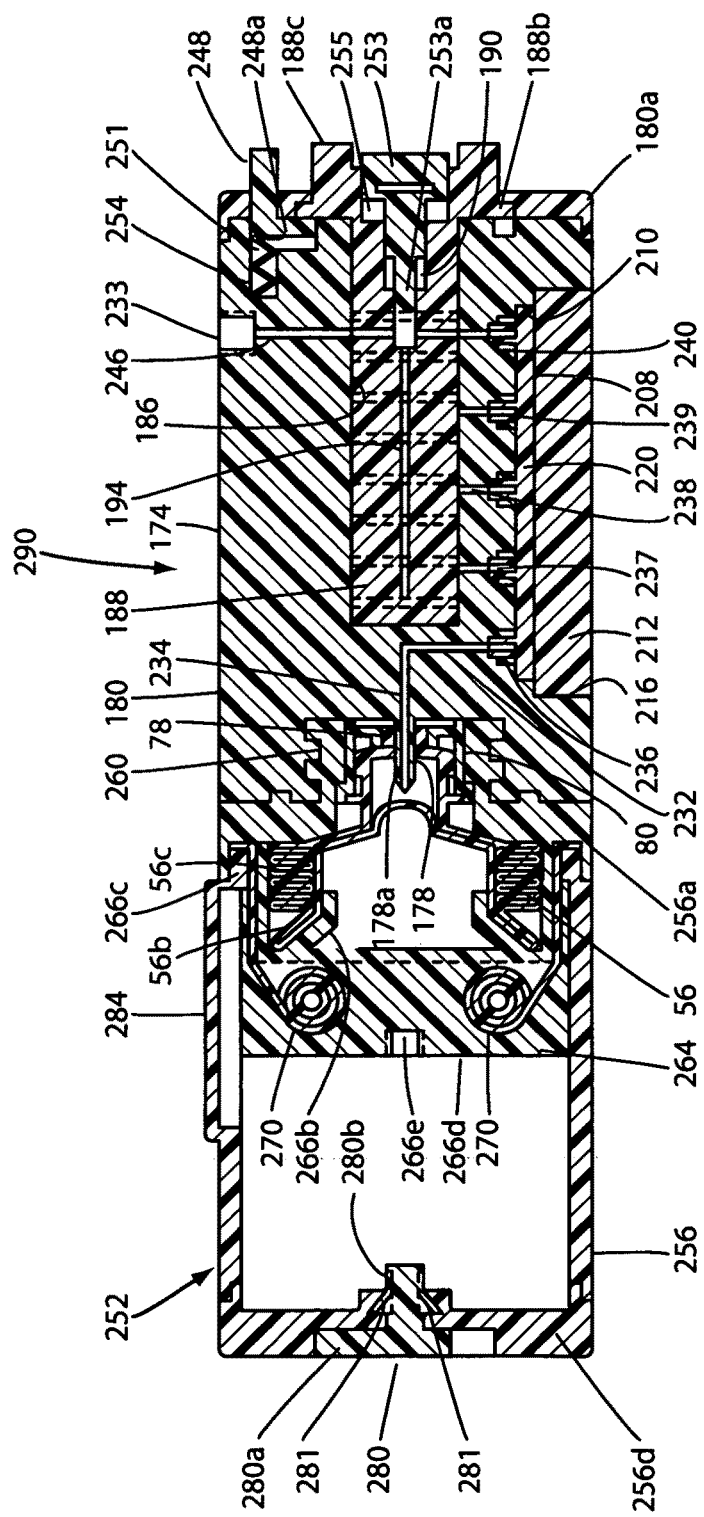
FIG. 48 is a longitudinal cross-sectional view of the fluid dispensing apparatus of the invention shown in FIGS. 37 and 44 wherein the first and second stand-alone components of the invention have been irreversibly operably interconnected.

Turning to FIG. 48 yet another form of the two part fluid dispensing apparatus of the present invention for dispensing medicaments is there shown and generally identified by the numeral 290. This alternate form of dispensing apparatus is similar in many respects to the earlier described embodiments of the invention and like numerals are used to identify like components (FIG. 48). As before, dispensing apparatus 290 comprises two stand-alone, interconnectable assemblies 252 and 174. As indicated in FIG. 48, first assembly 252 is substantially identical in construction and operation to the previously described first assembly that is illustrated in FIG. 44 of the drawings and comprises a fluid reservoir assembly that houses a fluid reservoir defining component 56 that is acted upon by a pair of constant for springs 270. Assembly 174 is substantially identical in construction and operation to the previously described second assembly that is illustrated in FIGS. 31, 33 and 37 of the drawings.

Assembly 174 comprises a penetrating member 178 and a novel fluid flow control means that includes a rate control assembly that permits the delivery of fluid to the patient at a plurality of selected rates of flow.

As in the earlier described embodiments of the invention, reservoir defining component 56 is constructed in accordance with aseptic blow-fill seal manufacturing techniques. As before, following molding, filling and sealing the reservoir defining component is sterilized at a relatively high temperature.

As before, second assembly 174 of this latest form of the fluid dispensing apparatus comprises a housing 180 that includes a longitudinally extending bore 186 that rotatably receives the rate control housing 188 of the second assembly, which rate control housing forms a part of the flow control means of the invention. The flow control means includes a rate control assembly 208 that is mounted within a cavity 210 provided in housing 180. Rate control assembly 208 comprises a rate control plate 220 that is provided with a plurality of spaced apart, serpentine micro-channels, each of which is of a different width, depth and length. When assemblies 252 and 174 are interconnected in the manner shown in FIG. 48, elongated passageway 230 of the rate control plate 220 is in communication with penetrating member 178 via a connector collar 236 provided on rate control plate 220, via passageway 232 and passageway 234.

With communication between the fluid reservoir 74 and the internal passageway 178a of the penetrating member 178 established, the fluid contained within the fluid reservoir can be expelled from the reservoir 74 by rotating the carriage release member 280 in the manner previously described. Once the carriage release member is free from the locking member receiving cavity 266e, the stored energy means, here shown as the pair of constant force springs 270 will urge the carriage forwardly. As the carriage moves forwardly, the accordion side walls of the container collapse causing the fluid to be forced outwardly from the reservoir into internal passageway 178a of the penetrating member. The fluid will then flow toward passageway 230 of the rate control plate 220 via the pressure regulator 231 and then into each of the microchannels to 222, 224, 226 and 228 that are interconnected with passageway 230. To enable the fluid to flow from the reservoir 74 to the patient at a selected rate via the administration set 130, the fluid control locking means of this latest form of the invention must be operated in the manner previously described.

As in the earlier described embodiments of the invention, a reservoir viewing window 284 is provided in housing 252 so that the amount of fluid contained within reservoir 74 can be monitored. Similarly, fluid flow from the reservoir 74 toward the rate control assembly of the second assembly can be prevented through operation of the disabling means that is of the character previously described.

Turning next to FIGS. 49 through 51, yet another form of fluid dispensing apparatus of the present invention for dispensing medicaments is there shown. This third, alternate, form of dispensing apparatus is similar in many respects to the earlier described embodiments of the invention and like numerals are used in FIGS. 49 through 51 to identify like components. As before, the dispensing apparatus comprises two stand-alone, inter-connectable assemblies of the character shown in FIGS. 50 and 51. As indicated in FIG. 50, first assembly 62 is substantially identical in construction and operation to the previously described first assembly. However, second assembly 304 is of a somewhat different construction.

The primary difference between second assembly 304 and the previously described second assembly resides in the provision of adding means for dispensing, in addition to the first fluid dispensed from the collapsible fluid container 56, a pre-selected second fluid from a medicament containing vial assembly. The details of construction and operation of the medicament containing vial assembly will presently be described. The collapsible fluid container 56 of this latest form of the invention is substantially identical in construction and operation to that previously discussed.

In a manner presently to be described, fluid medicament reservoir 74 of the fluid reservoir assembly 62 is accessible via the penetrating member 305 of the fluid delivery and control assembly 304. More particularly, penetrating member 305 is adapted to pierce closure wall 72 as well as a pierceable membrane 78 (FIG. 50) which is positioned over closure wall 72 by means of a closure cap 80 which is affixed to the neck portion 70 of reservoir defining assembly 56 (see also FIG. 11).

Considering now the second assembly 304 of this latest form of the fluid dispensing apparatus which is illustrated in FIGS. 49, 49A, 51, and 52 through 59, this assembly comprises a control housing 308 having a forward portion 308a and a rearward portion 308b. Rearward portion 308b, which is sealed by a hermetically affixed sterile barrier 310 having a pull tab 310a, includes an internally threaded cavity 383. Second sterile barrier 310, which is removably connected to rearward portion 308b in the manner shown in FIG. 51 of the drawings, here comprises a thin membrane constructed from any suitable polymer.

Figure 53:
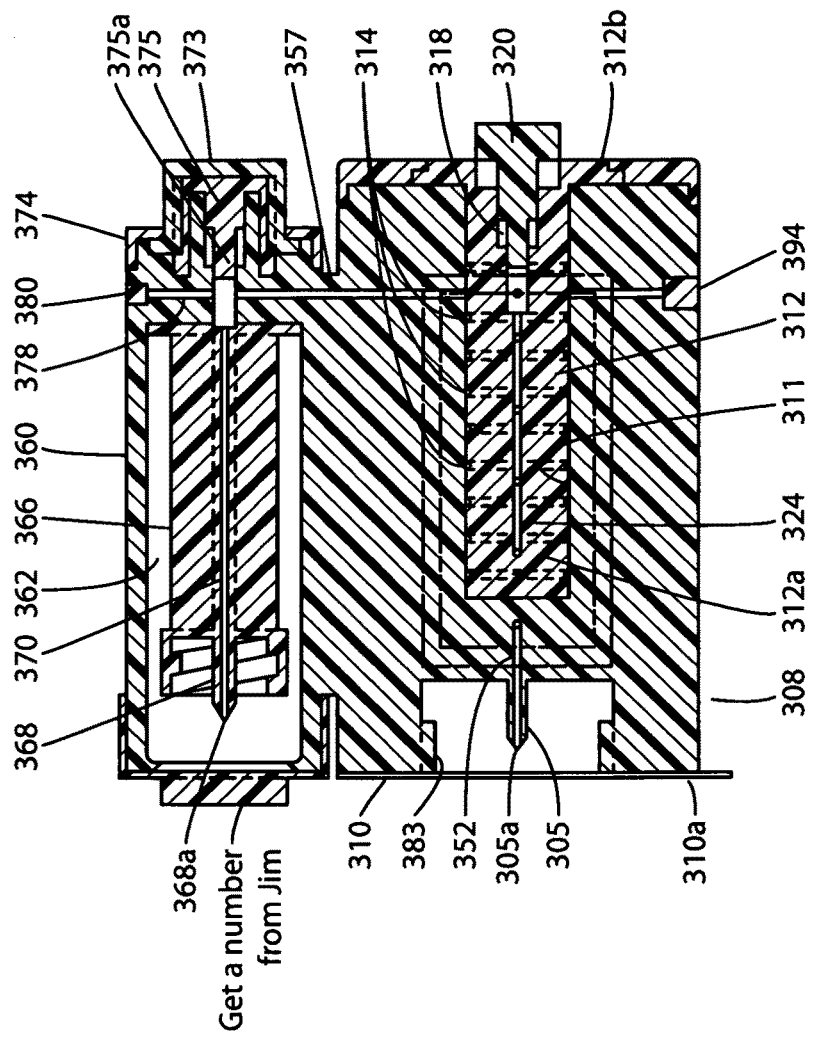
FIG. 53 is a cross-sectional view taken along lines 53-53 of FIG. 52.
Figure 52:
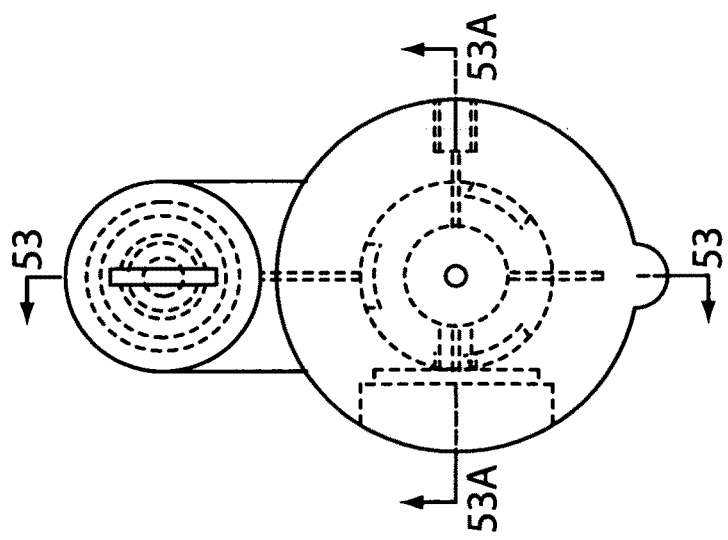
FIG. 52 is a rear view of the alternate form of second stand-alone component of the invention.
Figure 53A:
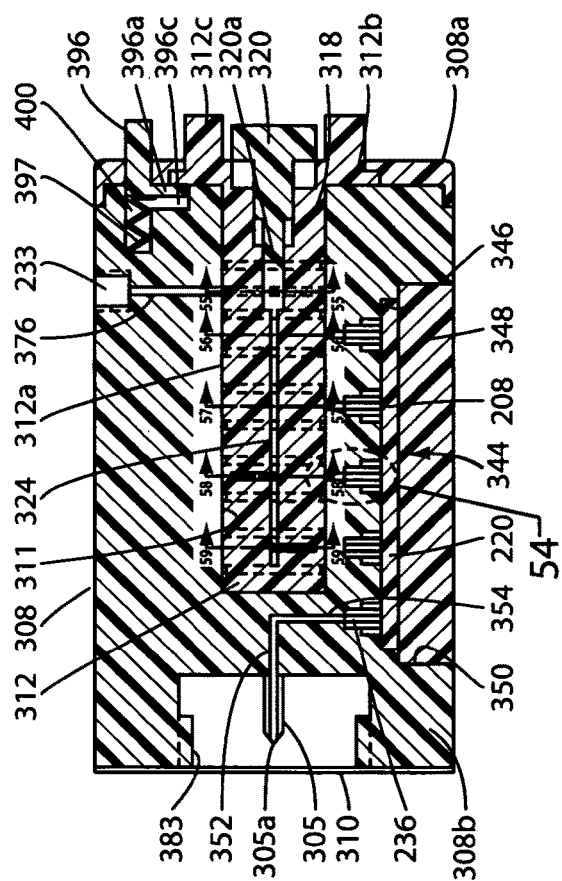
FIG. 53A is a cross-sectional view taken along lines 53A-53A of FIG. 52.
Figure 55:
FIG. 55 is a cross-sectional view taken along lines 55-55 of FIG. 53A.
Figure 54:
FIG. 54 is a cross-sectional view of the area designated as "54" in FIG. 53A.
Figure 56:
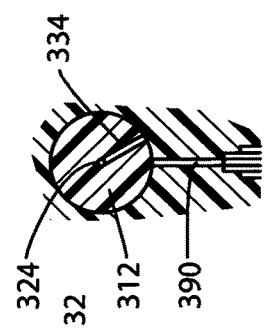
FIG. 56 is a cross-sectional view taken along lines 56-56 of FIG. 53A.
Figure 57:
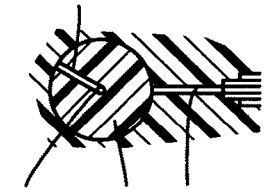
FIG. 57 is a cross-sectional view taken along lines 57-57 of FIG. 53A.
Figure 58:
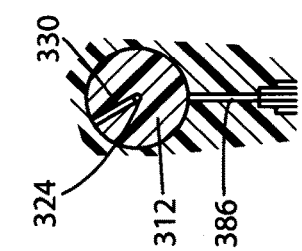
FIG. 58 is a cross-sectional view taken along lines 58-58 of FIG. 53A.
Figure 59:
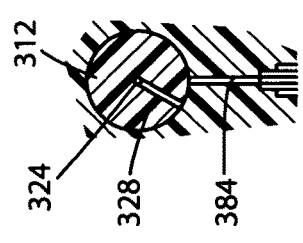
FIG. 59 is a cross-sectional view taken along lines 59-59 of FIG. 53A.
Figure 60:
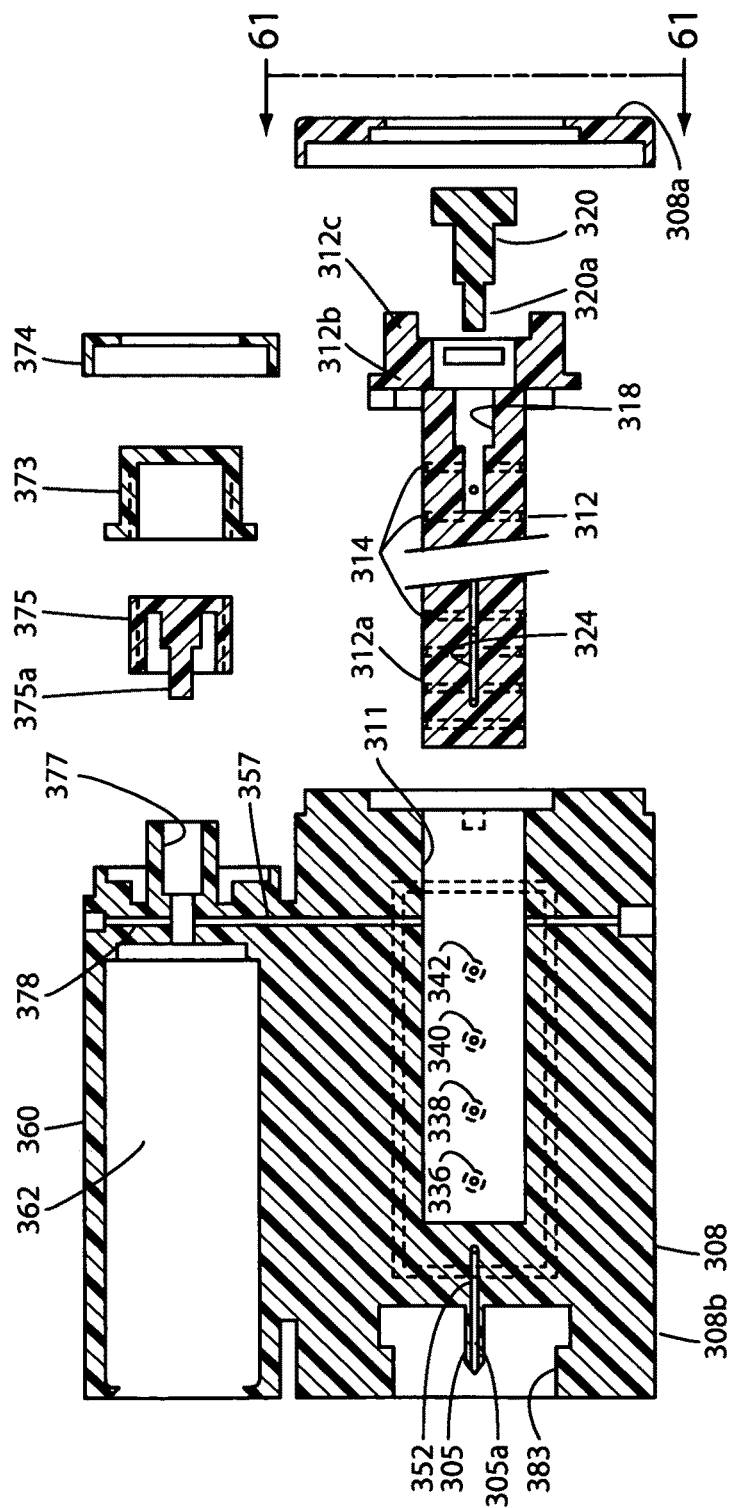
FIG. 60 is a longitudinal cross-sectional exploded view of the alternate form of second stand-alone component shown in FIGS. 49 and 49A of the drawings.

As illustrated in FIGS. 53, 53A and 60 of the drawings, housing 308 includes a longitudinally extending bore 311 that rotatably receives the rate control shaft 312 of the second assembly 304. Rate control shaft 312, which forms a part of the flow control means of this latest embodiment of the invention, includes an elongated body portion 312a, a forward flange 312b and a forwardly extending finger engaging portion 312c that is connected to and extends forwardly of flange 312b (FIG. 53A). For a purpose presently to be described, a plurality of circumferentially spaced apart channels, or cavities, are formed on the rear face of flange 312b. Additionally, a plurality of longitudinally spaced apart O-rings 314, which circumscribe body portion 312a, function to prevent fluid leakage between housing 308 and the body portion 312a of the rate control shaft as the shaft is rotated. Elongated body portion 312a is also provided with a longitudinally extending bore 318 that slidably receives the rearward portion of a disabling shaft 320, the construction and operation of which will presently be described.

As illustrated in FIGS. 51 and 60, body portion 312a is also provided with a longitudinally extending fluid passageway 324 that communicates with the flow passageway 305a of the previously identified piercing member 305 via the flow rate control means (see FIG. 53A). For a purpose presently to be described, body portion 312a is also provided with a plurality of spaced apart, radially extending outlet fluid flow passageways 328, 330, 332 and 334 that communicate with longitudinally extending, central passageway 324 (FIGS. 56, 57, 58 and 59).

In a manner presently to be described, housing 308 is provided with a plurality of longitudinally spaced apart, radially extending inlet fluid flow passageways 336, 338, 340 and 342 (FIG. 60) that also communicate with fluid passageway 324 as the rate control shaft is rotated. Inlet fluid flow passageways 336, 338, 340 and 342 selectively communicate with a rate control assembly 208 that is mounted within a cavity 346 provided in a housing 308 (FIG. 53A). Rate control assembly 208, which also forms a part of the flow control means of this latest form of the invention, is substantially identical in construction and operation to the previously described rate control assembly 208 and is maintained within cavity 346 by a rate control cover 348. As best seen in FIG. 53A of the drawings, rate control cover 348 is disposed within a cavity 350 formed in housing 308.

As previously discussed and as shown in FIGS. 34 through 36, rate control assembly 208 comprises a rate control plate 220, which is provided with a plurality of spaced apart, serpentine micro-channels 222, 224, 226 and 228. Each of the micro-channels is of a different width, depth and length and each has an inlet in communication with an elongated passageway 230, which in turn is in communication with the internal passageway 305a of the penetrating member 305 via passageways 352 and 354 formed in housing 308 (see FIG. 53A). A thin cover 235 covers the channels in the manner shown in FIG. 34.

Figure 65:
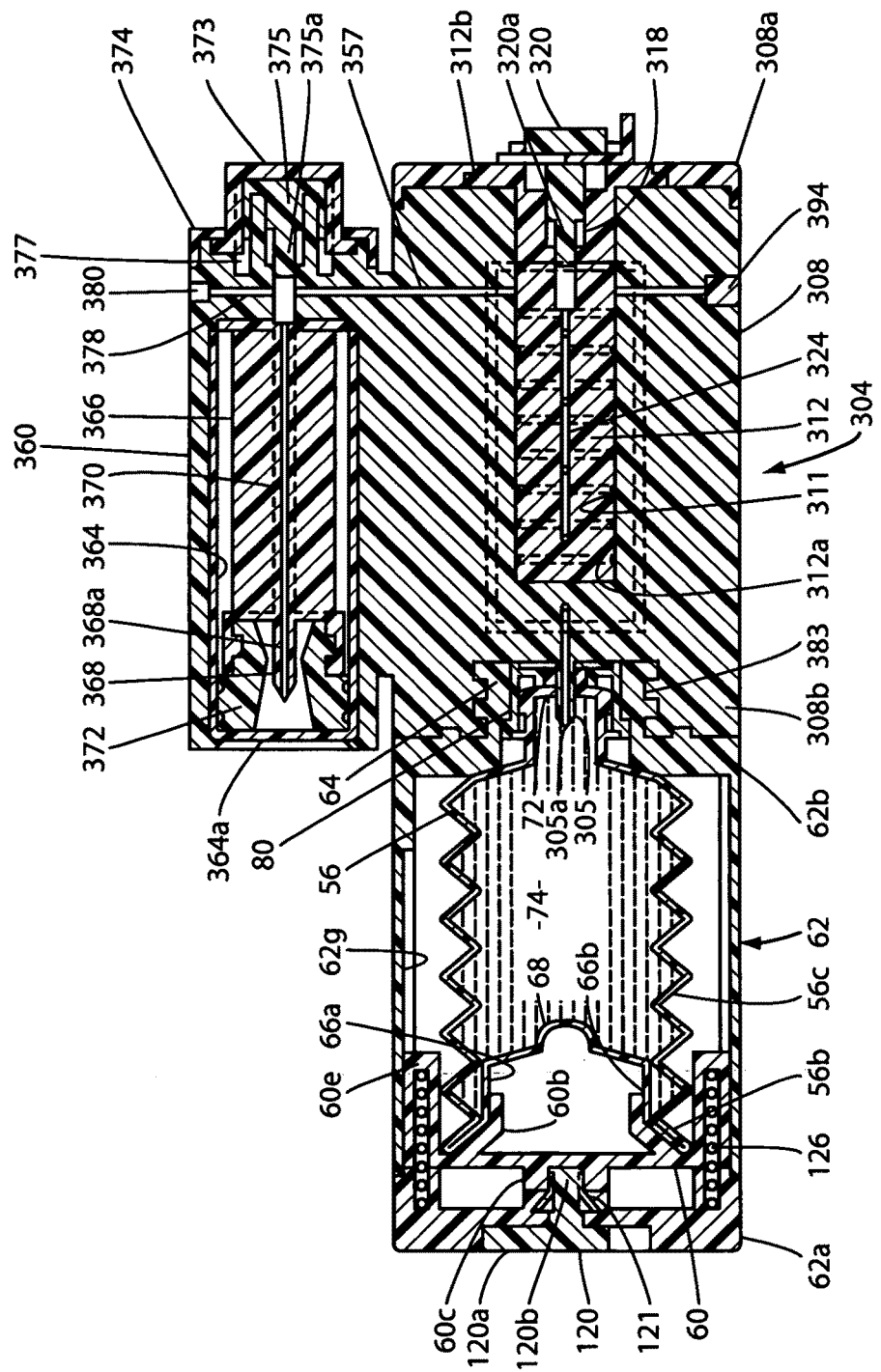
FIG. 65 is a longitudinal cross-sectional view illustrating the assembly of the two parts of the two-part fluid delivery system of this alternate form of the invention.

When assemblies 62 and 304 are interconnected in the manner shown in FIG. 65, elongated passageway 324 is in communication with penetrating member 305 via a connector collar 236 provided on rate control plate 220, via passageways 352 and 354 formed in housing 308 (see FIG. 53A). The previously identified additive means of this latest form of the invention is in communication with the administration set of the invention via passageway 357 formed in housing 308 (see FIGS. 53 and 60).

The novel additive means, or medicament vial assembly, of this latest form of the invention comprises an additive housing 360 that is integrally formed with housing 308 in the manner depicted in FIGS. 49, 49A and 53. Housing 360 is provided with a chamber 362 for telescopically receiving a medicament containing fill-vial 364 containing the second medicament. An elongated needle holding component 366, which is disposed within chamber 362, functions to hold the fill-vial 364 in a proper position within chamber 362 and in a manner presently to be described also functions as a fill-vial pusher member.

As shown in FIG. 51, needle holding component 366 carries a longitudinally extending, elongated hollow needle 368 having a flow passageway 368a that communicates with an elongate fluid passageway 370 that is provided within needle holding component 366. Fill-vial 364, needle holding component 366 and hollow needle 370 all form a part of the adding means of the apparatus of the present invention. The method of operation of this important adding means will presently be described.

Referring particularly to FIG. 50, the medicament containing fill-vial 364 can be seen to comprise a container that is sealed at one end by an end wall 364a and at the other end by slidable, elastomeric plunger 372 having a pierceable central wall 372a.

Figure 79B:
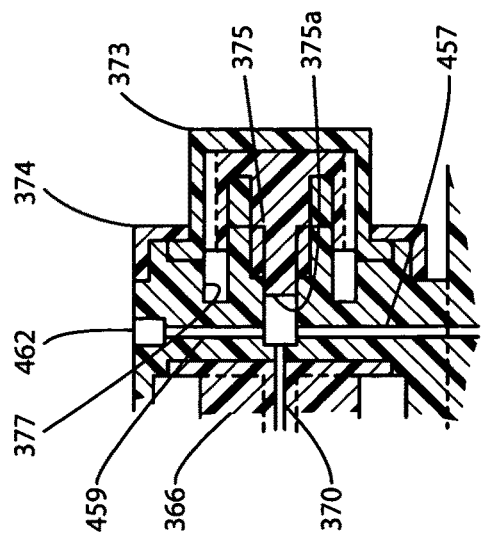
FIG. 79B is a fragmentary cross-sectional view of the operating mechanism of the medicament vial assembly of the second stand-alone component shown in FIG. 67 showing the mechanism in an "on" position.
Figure 79A:
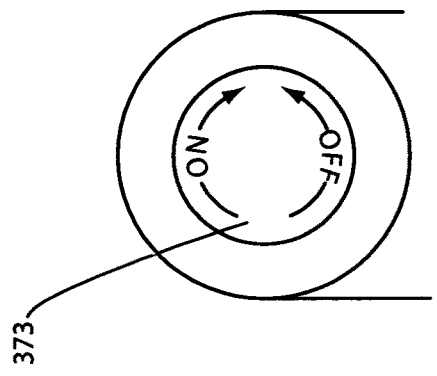
FIG. 79A is a fragmentary front view of the operating mechanism of the medicament vial assembly of the second stand-alone component shown in FIG. 67.
Figure 79:
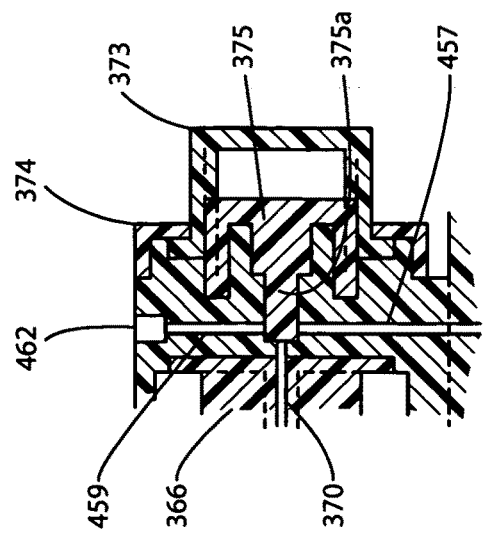
FIG. 79 is a fragmentary cross-sectional view of the operating mechanism of the medicament vial assembly of the second stand-alone component shown in FIG. 67 showing the mechanism in an "off" position.

In operating the adding means of the invention, with the on-off selector 373 rotated to an "on" position such as shown in FIGS. 79A and 79B, a pressure exerted on container 364 urging the container into chamber 362 of additive housing 360 will cause the needle 368 to pierce central wall 372a. A continued inward pressure exerted on container 364 will cause the slidable elastomeric plunger 372 to be moved inwardly of the fluid reservoir 364b by the needle holding component 366. The inward movement of plunger 372 will, in turn, cause the fluid "F" contained within the reservoir 364b of the container to flow into flow passageway 368a of needle 368, then into fluid passageway 370 and finally into the administration set via fluid passageway 357. As best seen in FIG. 51, fluid passageway 357 also communicates with a fluid passageway 378 that is in communication with a conventional gas vent 380 that is mounted in additive housing 360. Gas vent 380 functions in a conventional manner to vent to atmosphere any gases trapped within the fluid passages of the device.

Medicament containing fill vial 364 can be of various volumes and can contain various second beneficial agents. Similarly, fluid medicament reservoir 74 of the fluid reservoir assembly 62 can be of various volumes and can contain various first beneficial agents.

In using the apparatus of this latest form of the invention to deliver a first medicament from collapsible fluid container 56, the first step is to rotate the on-off selector 373 to an "off" position, wherein the reduced diameter portion 375a of the closure member 375 of the selector 373 is moved into a chamber 377 formed in housing 360 (see FIGS. 51 and 60). With portion 375a of the closure member 375 moved into a chamber 377, fluid flow from passageway 370 into passageways 357 is blocked. The next step is to remove the sterile covers 64a and 310a from assemblies 62 and 304. This done, the assemblies can be interconnected by inserting the externally threaded neck 64 of assembly 62 into internally threaded cavity 383 of assembly 304 and rotating assembly 62 relative to assembly 304. As the assemblies are mated, penetrating member 305 will penetrate elastomeric member 78 and closure wall 72 of the collapsible container 56.

With communication between the fluid reservoir 74 and the internal passageway 305a of the penetrating member 305 having thusly been established, the fluid contained within the fluid reservoir 74 can be expelled from the reservoir by rotating the carriage release member 120 in the manner previously described. Once the carriage release member is free from the locking member receiving protuberance, the stored energy means, here shown as a coil spring 126 that is movable from the first compressed position shown in FIG. 50 to the second extended position shown in FIG. 65A, will urge the carriage forwardly. As the carriage moves forwardly, the accordion side walls of the container collapse, causing the fluid to be forced outwardly of the reservoir 74 into internal passageway 305a of the penetrating member. The fluid will then flow toward passageway 230 of the rate control plate 220 via passageways 352 and 354 formed in housing 308 (see FIG. 53A). From passageway 230 the fluid will flow into and fill each of the micro-channels to 222, 224, 226 and 228 that are interconnected with passageway 230 in the manner shown in FIG. 36.

To enable the fluid to flow from the reservoir 74 to the patient via the administration set 130 (FIG. 8A) that can be connected to the outlet port 233 of housing 180 (FIG. 33), the fluid control locking means of this latest form of the invention must be operated. More particularly, to permit fluid flow selectively from the outlets 222a, 224a, 226a, and 228a, respectively, of the differently configured micro-channels (FIG. 36), the rate control shaft 312 must be controllably rotated in a manner to selectively align the radially extending passageways 328, 330, 332 and 334 with the longitudinally spaced apart flow passageways 384, 386, 388 and 390 formed in housing 308 (FIGS. 53 through 59). Since passageways 328, 330, 332 and 334 are in communication with micro-channel outlets 222a, 224a, 226a, and 228a, respectively, of the differently configured micro-channels, fluid can flow from the selected micro-channel toward the selected flow passageway 328, 330; 332 and 334 at a controlled rate that depends upon the configuration of the particular channel selected.

From the selected radially extending passageways 328, 330, 332 and 334, fluid will flow into passageway 324 formed in shaft 312, toward the inlet of the administration set. Any gases trapped in the device reservoir and in the various fluid passageways will be vented to atmosphere via a vent port 394 mounted in control housing 308 (FIG. 51).

As in the earlier described embodiment of the invention, rotation of the rate control shaft 312 cannot be accomplished until the rate control locking means is operated by the caregiver. In this latest form of the invention, the rate control locking means comprises a plunger 396 that includes a locking finger 396a (FIG. 53A) that prevents rotation of the rate control housing, unless and until the plunger is moved inwardly of the housing against the urging of a biasing means shown here as coil spring 397 that is housed within a chamber 400 formed in housing 308. Once the plunger is appropriately urged inwardly and the locking finger 396a is removed from the channels, or cavities, that are formed on the rear face of flange 312b, the rate control shaft 312 can be rotated into the desired fluid flow position by grasping rotation fingers 312c and imparting a rotational force thereto. As the rate control housing is rotated, spring 397 continuously urges locking finger 396a into a selected locking channel 312d formed in flange 312b. As before, when the locking finger is seated within a particular locking channel, one of the radially extending passageways formed in the rate control shaft will be locked in communication with one of the outlets of one of the plurality of micro channels formed in the rate control plate and the fluid will flow through the selected micro channel toward the patient at a selected fixed-rate.

When it is desired to dispense the second medicinal fluid to the patient from the adding means of the invention, the sealable barrier 403 is removed from the additive housing 364 (FIG. 50). This done, the on-off selector 373 is rotated to an "on" position, such as shown in FIG. 51. With the on-off selector 373 in the "on" position, a pressure exerted on container 364 urging the container into chamber 362 of additive housing 360 will cause the needle 368 to pierce central wall 372a. A continued inward pressure exerted on container 364 will cause the slidable elastomeric plunger 372 to be moved inwardly of the fluid reservoir 364b by the needle holding component 366. The inward movement of plunger 372 will, in turn, cause the fluid "F" contained within the reservoir 364b of the container to flow into flow passageway 368a of needle 368, then into fluid passageway 370, and finally into the administration set via fluid passageway 376.

Referring now to FIGS. 66 through 81, still another form of fluid dispensing apparatus of the present invention for dispensing medicaments is there shown. This fourth, alternate, form of dispensing apparatus is similar in many respects to the earlier described embodiments of the invention and like numerals are used in FIGS. 66 through 81 to identify like components. As before, dispensing apparatus comprises two stand-alone, inter-connectable assemblies, the first of which is substantially identical in construction and operation to the previously described first assembly 62. However, second assembly 404 is of a somewhat different construction.

The primary difference between second assembly 404 and the previously described second assembly 304 resides in the provision of a fixed rather than a variable fluid flow rate. The adding means, including the medicament containing vial assembly, is substantially identical in construction and operation to that previously described. Additionally, the collapsible fluid container 56 of this latest form of the invention is also substantially identical in construction and operation to that previously discussed. Further, fluid medicament reservoir 74 of the fluid reservoir assembly 62 is accessible in the manner previously described via the penetrating member 405 of the fluid delivery and control assembly 404 (FIG. 67). More particularly, penetrating member 405 is adapted to pierce closure wall 72 as well as a pierceable membrane 78 (FIG. 50) which is positioned over closure wall 72 by means of a closure cap 80 which is affixed to the neck portion 70 of reservoir defining assembly 56 (see also FIG. 11).

Figure 68:
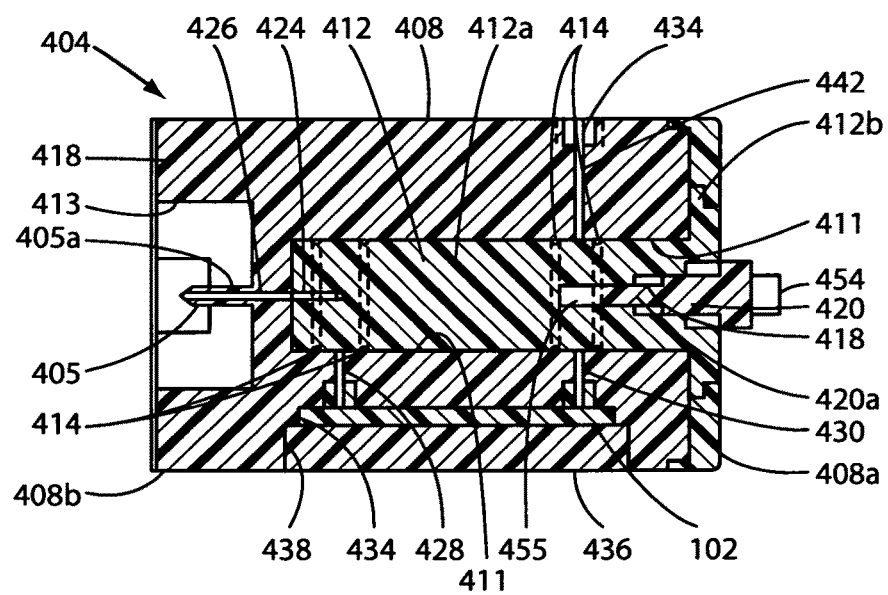
FIG. 68 is a cross-sectional view taken along lines 68-68 of FIG. 67.
Figure 69:
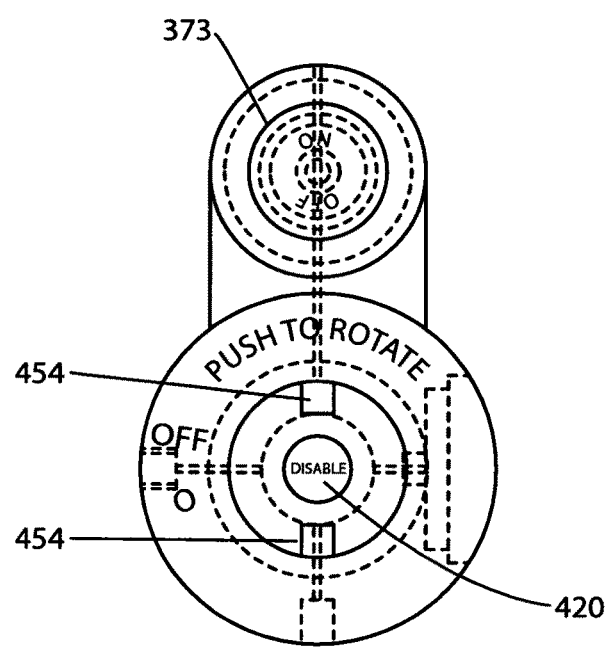
FIG. 69 is a view taken along lines 69-69 of FIG. 67.

Considering now in greater detail the second assembly 404 of this latest form of the fluid dispensing apparatus the construction which is illustrated in FIGS. 67 and 68. This assembly comprises a control housing 408 having a forward portion 408a and a rearward portion 408b. Rearward portion 408b, which is sealed by a hermetically affixed sterile barrier having a pull tab, includes an internally threaded cavity 413. This second sterile barrier, which is removably connected to rearward portion 408b, here comprises a thin membrane constructed from any suitable polymer.

As illustrated in FIGS. 67 and 68 of the drawings, housing 408 includes a longitudinally extending bore 411 that rotatably receives the rate control shaft 412 of the second assembly 404. Rate control shaft 412 which forms a part of the flow control means of this latest embodiment of the invention includes an elongated body portion 412a and a forward flange 412b. Additionally, a plurality of longitudinally spaced apart O-rings 414, which circumscribe body portion 412a, function to prevent fluid leakage between housing 408 and the body portion 412a of the rate control shaft as the shaft is rotated. Elongated body portion 412a is also provided with a longitudinally extending bore 418 that slidably receives the rearward portion of a disabling shaft 420, the construction and operation of which will presently be described.

As illustrated in FIGS. 67 through 79, body portion 412a is also provided with a longitudinally extending fluid passageway 424 that communicates with the flow passageway 405a of the previously identified piercing member 405 via a passageway 426 provided in control housing 408. For a purpose presently to be described, control housing 408 is also provided with a pair of longitudinally spaced fluid flow passageways 428 and 430.

Fluid flow passageway 428 comprises an inlet passageway that communicates with a rate control assembly 102 that is mounted within a cavity 434 provided in a housing 408. Rate control assembly 102, which also forms a part of the flow control means of this latest form of the invention, is maintained within cavity 434 by a rate control cover 436, which also forms a part of the flow control means of the invention. As best seen in FIG. 68 of the drawings, rate control cover 436 is disposed within a cavity 438 formed in housing 408. Rate control assembly 102 is substantially identical in construction and operation to that described in connection with the embodiment of FIGS. 1 through 29.

As best seen in FIGS. 18 through 22, rate control assembly 102 comprises a rate control plate 10, which as shown in FIG. 23 is provided with a serpentine micro-channel 112 having an inlet 112A and an outlet 112b which communicates with passageway 100 that comprises an outlet passageway. The length, width and depth of the micro-channel determine the rate at which the fluid will flow toward outlet 112b. A thin cover 114 covers the channel in the manner shown in FIG. 18. When assemblies 52 and 404 are interconnected, inlet 112A is in communication with penetrating member 405 via passageway 428, via passageway 432 (FIG. 76), and via passageway 426. Because the second assembly has been sterilized in the manner previously described, these passageways are completely sterile at the time assembly 404 is connected to assembly 52.

In using the apparatus of the invention, the first step is to remove the sterile covers from assemblies 52 and 404. This done, the assemblies can be irreversibly interconnected in the manner previously described by inserting the externally threaded neck 64 of assembly 62 into internally threaded cavity 413 of assembly 404 and rotating assembly 62 relative to assembly 404. As the assemblies mate, penetrating member 405 will penetrate elastomeric member 78 and closure wall 72 of the container.

With communication between the fluid reservoir 74 and the internal fluid passageway 405a of the penetrating member 405 having thusly been established, the fluid contained within the fluid reservoir can be expelled from the reservoir 74 by rotating the carriage release member 120 which comprises a part of the previously identified carriage locking means. This is accomplished by grasping the finger engaging arm 120A of the release member (FIG. 14) and rotating the member in the manner indicated in FIG. 2 until the threaded shank 120b of the knob threadably disengages from the locking member receiving protuberance 60c. Release member 120 is held in position within housing base 62a by means of circumferentially spaced locking tabs 121 provided on shank 120b. Once the carriage release member is free from the locking member receiving protuberance, the stored energy means, here shown as a coil spring 126 that is movable from the first compressed position shown in FIG. 7 to a second extended position shown in FIG. 16, will urge the carriage forwardly in the manner illustrated in FIG. 16 of the drawings. As the carriage moves forwardly, the circumferentially spaced guide tabs 60e formed on the carriage (FIG. 9) will slide within and be guided by guide channel 62g formed in housing 62 (FIG. 7). As the accordion side walls collapse, the fluid will be forced outwardly of the reservoir into internal passageway 405a of the penetrating member. In the manner previously described, the fluid will then flow toward the fluid flow control means of the invention which functions to control the flow of fluid from the fluid reservoir of the fluid delivery portion of the device toward the patient.

To enable the fluid to flow from the reservoir 74 to the patient via the administration set 130 which is substantially identical in construction and operation to that previously described (FIG. 8A), the fluid control locking means must be operated in the manner presently to be described. The administration set 130 is sealably interconnected with an outlet port 434 formed in housing 408 (FIG. 68).

To permit fluid flow toward the rate control micro-channel 112, the rate control shaft, or housing 412, must be rotated to a position wherein flow passageway 432 aligns with a flow passageway 428 formed in housing 412 (FIGS. 73 and 76). Since passageway 428 is in communication with the rate control channel, fluid can flow through the micro-channel at a controlled fixed rate, depending upon the configuration of the channel, into passageway 438, into passageway 440 and finally into passageway 442 (FIGS. 72 and 77). From passageway 442, the fluid will flow into the inlet of the administration set for delivery to the patient at a predetermined fixed rate. During the fluid delivery step any gases contained within the device reservoir and the various fluid passageways are vented to atmosphere via vent port 444 and passageway 444a (FIG. 67).

As previously mentioned, rotation of the rate control housing 412 cannot be accomplished until the rate control locking means is operated by the caregiver. In the present form of the invention, this rate control locking means comprises a plunger 448 that includes a locking finger 448a (FIG. 67) that prevents rotation of the rate control housing, unless and until the plunger is moved inwardly of the housing against the urging of a biasing means shown here as coil spring 450 that is housed within a chamber 452 formed in housing 408. Once the plunger is appropriately urged inwardly, rate control housing can be rotated from the "off" position into the fluid flow, or "on" position, by grasping rotation fingers 454 and imparting a rotational force to the rotating fingers (see also FIGS. 70 through 78).

Fluid flow from the reservoir 74 toward the patient can be prevented through operation of the disabling means of the invention. This important disabling means, which is illustrated in FIGS. 67 and 70, comprises the previously identified disabling shaft 420. As indicated in the drawings, when the disabling shaft 420 is pushed inwardly from the position shown in FIG. 67 into an inward position, the forward portion 420a of the disabling shaft will move into a cavity 455 formed in rate control housing 408, thereby blocking fluid toward the internal passageway 442. By stopping fluid flow in this manner, the apparatus is substantially safely disabled until the disabling shaft 420 is once again returned to the starting position shown in FIG. 67 of the drawings.

Figure 65A:
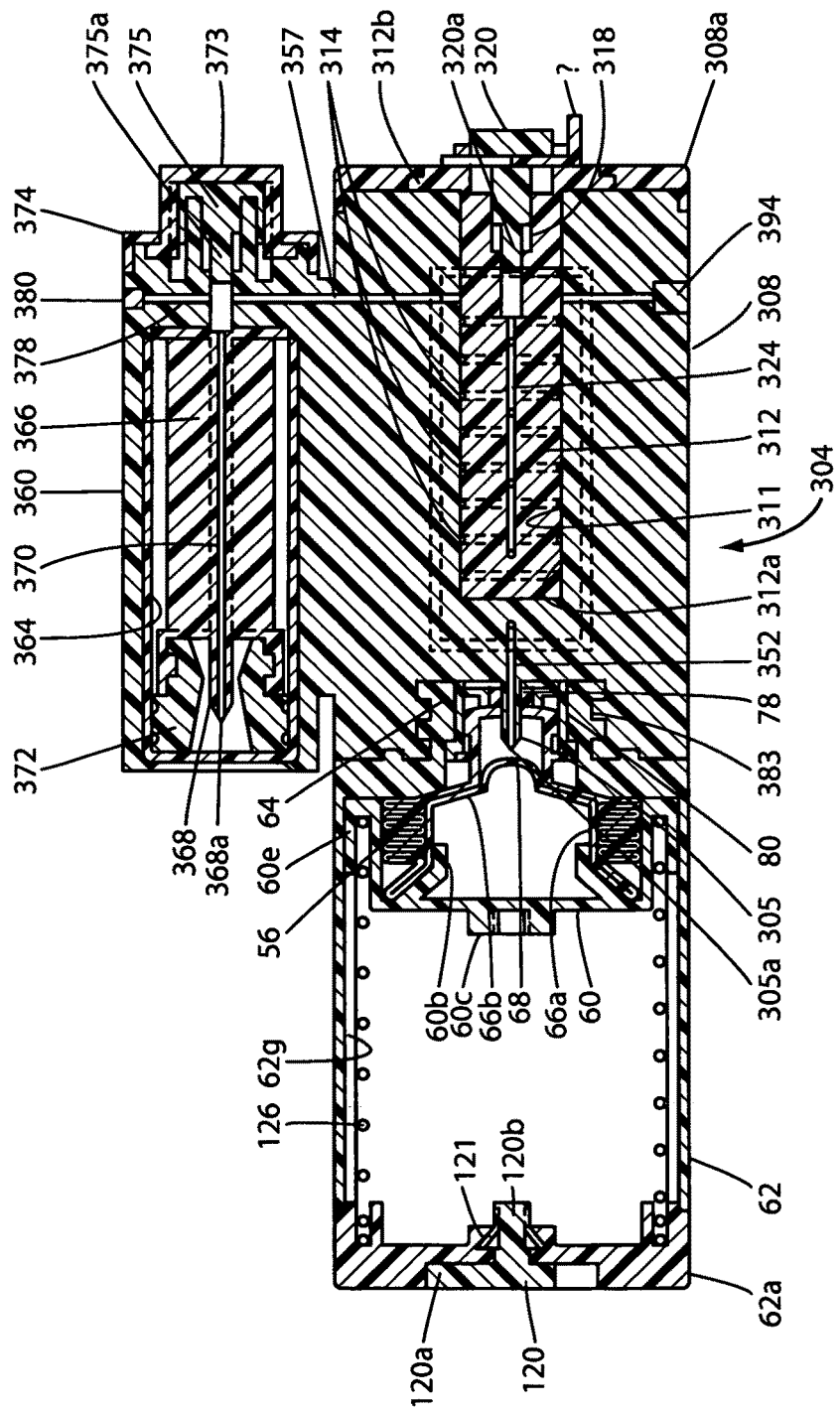
FIG. 65A is a longitudinal cross-sectional view similar to FIG. 65, but showing the appearance of the assembly after the collapse of the collapsible fluid container of the first stand-alone component shown in FIG. 50 of the drawings.

In operating the adding means of this latest form of the invention, which as previously mentioned is substantially identical in construction and operation to that previously described, with the on-off selector 373 rotated to an "on" position such as shown in FIG. 65A, the container 364 is mated with the additive housing in the manner previously described. As before, the inward movement of plunger 372 will cause the fluid "F" contained within the reservoir 364b of the container to flow into flow passageway 368a of needle 368, then into fluid passageway 370, and finally into the administration set via fluid passageway 457 (FIG. 67). As indicated in FIG. 67, fluid passageway 457 also communicates with a fluid passageway 459 that is in communication with a conventional gas vent 462 that is mounted in the additive housing. Gas vent 462 functions in a conventional manner to vent to atmosphere any gases trapped within the fluid passages of the device.

Referring next to FIGS. 80 through 98, still another form of fluid dispensing apparatus of the present invention for dispensing medicaments is there shown and generally identified by the numeral 464. This fifth, alternate, form of dispensing apparatus is also similar in many respects to the earlier described embodiments of the invention and like numerals are used in FIGS. 80 through 98 to identify like components. As before, dispensing apparatus comprises two stand-alone, inter-connectable assemblies, the first of which is substantially identical in construction and operation to the previously described first assembly 62. However, second assembly 464 is of a somewhat different construction (see FIGS. 81, 82 and 82A).

The primary difference between second assembly 464 and the previously described second assembly 404 resides in the provision of a novel adding means that is removably connected to the control housing 468 of second assembly 464. As will be discussed in greater detail hereinafter, control housing 468 is generally similar in construction and operation to the previously described control housing 408.

In this latest form of the invention, the fluid medicament reservoir 74 of the fluid reservoir assembly 62 is accessible in the manner previously described via the penetrating member 469 of the fluid delivery and control assembly 464 (FIG. 82). More particularly, penetrating member 469 is adapted to pierce closure wall 72 as well as a pierceable membrane 78 (FIG. 81) which is positioned over closure wall 72 by means of a closure cap 80 which is affixed to the neck portion 70 of reservoir defining assembly 56 (see also FIG. 11).

Considering now in greater detail the second assembly 464 of this latest form of the fluid dispensing apparatus the construction of which is illustrated in FIG. 82. This assembly comprises a control housing 468 having a forward portion 468a and a rearward portion 468b. Rearward portion 468b, which is sealed by a hermetically affixed sterile barrier having a pull tab, includes an internally threaded cavity 473. This second sterile barrier which is removably connected to rearward portion 468b, here comprises a thin membrane constructed from any suitable polymer.

As illustrated in FIG. 82 of the drawings, housing 468 includes a longitudinally extending bore 471 that rotatably receives the rate control shaft 472 of the second assembly 464. Rate control shaft 472 which forms a part of the flow control means of this latest embodiment of the invention, includes an elongated body portion 472a and a forward flange 472b. Additionally, a plurality of longitudinally spaced apart O-rings 474, which circumscribe body portion 472a, function to prevent fluid leakage between housing 468 and the body portion 472a of the rate control shaft as the shaft is rotated. Elongated body portion 472a is also provided with a longitudinally extending bore 478 that slidably receives the rearward portion of a disabling shaft 480, the construction and operation of which will presently be described.

As illustrated in FIGS. 82 and 84, body portion 472a is also provided with a longitudinally extending fluid passageway 484 that communicates with the flow passageway 469a of the previously identified piercing member 469 via a passageway 486 provided in control housing 464. For a purpose presently to be described, body portion 468 is provided with a pair of longitudinally spaced fluid flow passageways 488 and 490 (FIG. 82A).

Fluid flow passageway 488 comprises an inlet passageway that communicates with a rate control assembly 102 that is mounted within a cavity 494 provided in a housing 464. Rate control assembly 102 which also forms a part of the flow control means of this latest form of the invention is maintained within cavity 494 by a rate control cover 496, which also forms a part of the flow control means of the invention. As best seen in FIG. 82A of the drawings, rate control cover 496 is disposed within a cavity 498 formed in housing 464.

Rate control assembly 102 is substantially identical in construction and operation to that described in connection with the embodiment of FIGS. 1 through 29.

As best seen in FIGS. 18 through 22, rate control assembly 102 comprises a rate control plate 10, which as shown in FIG. 23 is provided with a serpentine micro-channel 112 having an inlet 112A and an outlet 112b which communicates with passageway 100 that comprises an outlet passageway. The length, width and depth of the micro-channel determine the rate at which the fluid will flow toward outlet 112b. A thin cover 114 covers the channel in the manner shown in FIG. 18. When assemblies 52 and 464 are interconnected, inlet 112A is in communication with penetrating member 469 via passageway 486, via passageway 488 and via passageway 492 (FIG. 82D). Because the second assembly has been sterilized in the manner previously described, these passageways are completely sterile at the time assembly 464 is connected to assembly 52.

In using the apparatus of the invention, the first step is to remove the sterile covers from assemblies 52 and 464. This done, the assemblies can be irreversibly interconnected in the manner previously described by inserting the externally threaded neck 64 of assembly 52 into internally threaded cavity 473 of assembly 464 and rotating assembly 52 relative to assembly 464. As the assemblies mate, penetrating member 469 will penetrate elastomeric member 78 and closure wall 72 of the container.

With communication between the fluid reservoir 74 and the internal fluid passageway 469a of the penetrating member 469 having thusly been established, the fluid contained within the fluid reservoir can be expelled from the reservoir 74 by rotating the carriage release member 120 which comprises a part of the previously identified carriage locking means. This is accomplished by grasping the finger engaging arm 120A of the release member (FIG. 14) and rotating the member in the manner indicated in FIG. 2 until the threaded shank 120b of the knob threadably disengages from the locking member receiving protuberance 60c. Release member 120 is held in position within housing base 62a by means of circumferentially spaced locking tabs 121 provided on shank 120b. Once the carriage release member is free from the locking member receiving protuberance, the stored energy means, here shown as a coil spring 126 that is movable from the first compressed position shown in FIG. 7 to a second extended position shown in FIG. 16, will urge the carriage forwardly in the manner illustrated in FIG. 16 of the drawings. As the carriage moves forwardly, the circumferentially spaced guide tabs 60e formed on the carriage (FIG. 9) will slide within and be guided by guide channel 62g formed in housing 62 (FIG. 7). As the accordion side walls collapse, the fluid will be forced outwardly of the reservoir into internal passageway 469a of the penetrating member. In the manner previously described, the fluid will then flow toward the fluid flow control means of the invention which functions to control the flow of fluid from the fluid reservoir of the fluid delivery portion of the device toward the patient.

Figure 80:
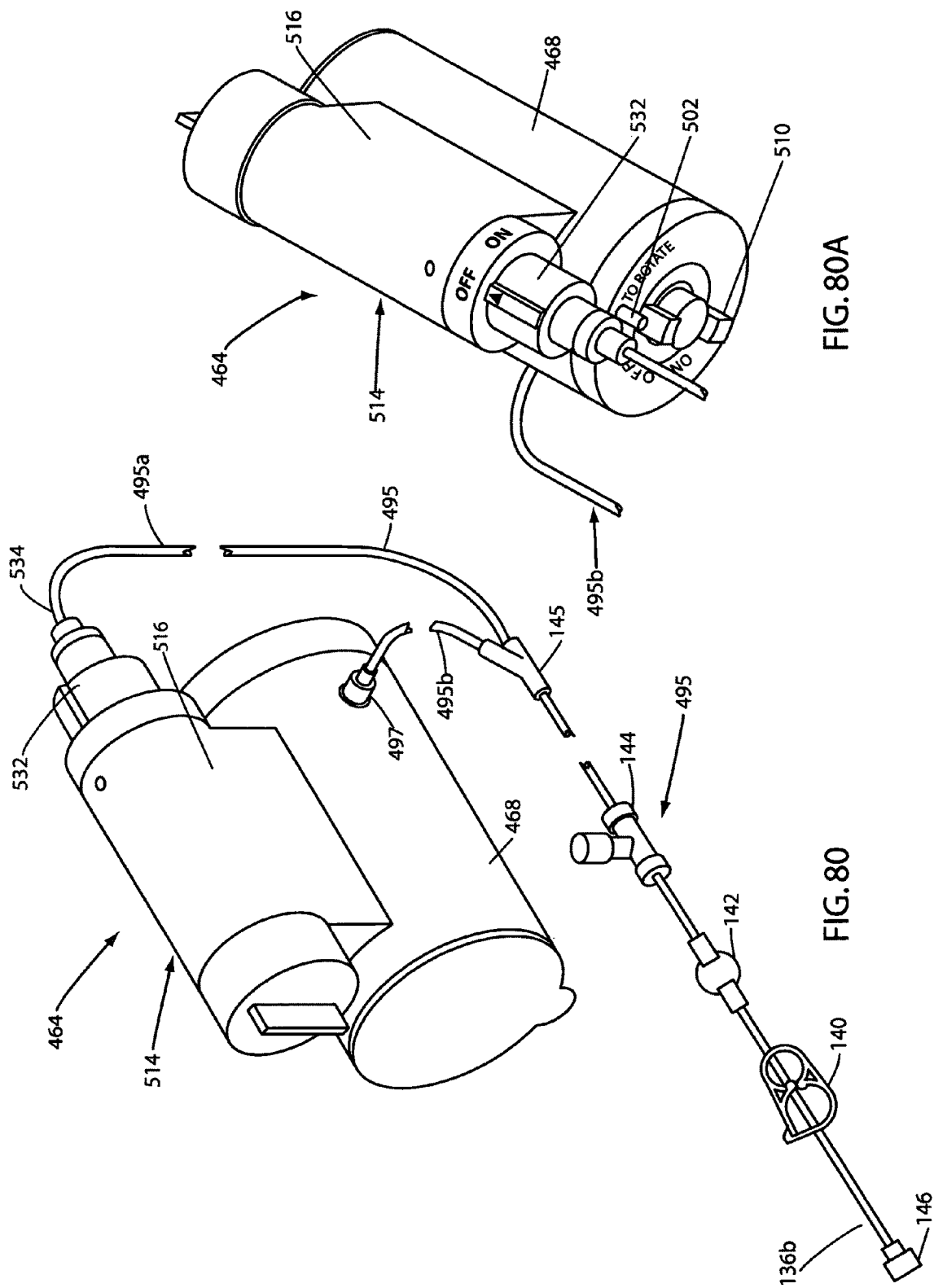
FIG. 80 is a generally perspective rear view of still another form of the apparatus of the invention.
Figure 81:
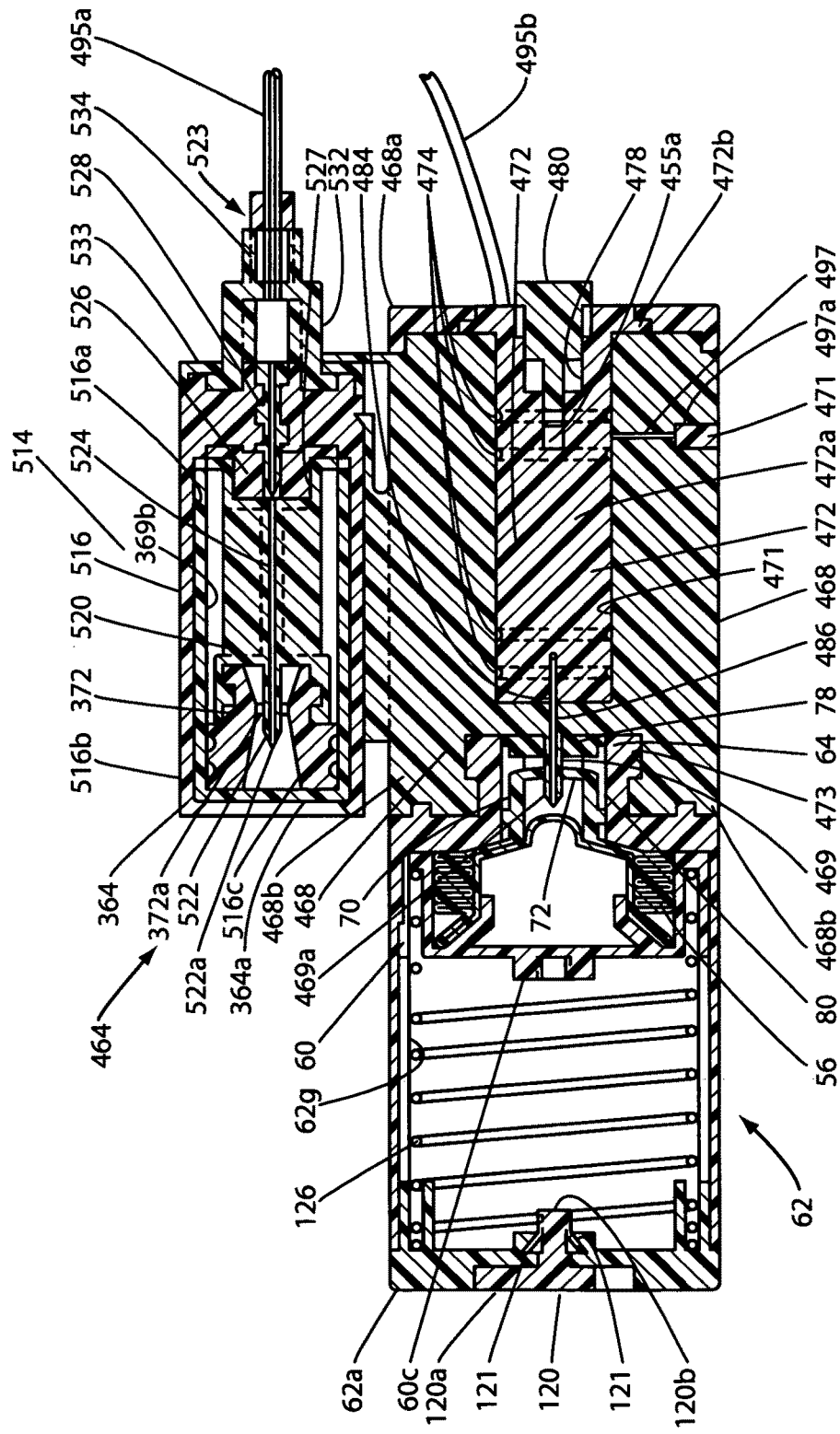
FIG. 81 is an enlarged longitudinal cross-sectional view of the alternate form of the apparatus shown in FIGS. 80 and 80A.
Figure 97:
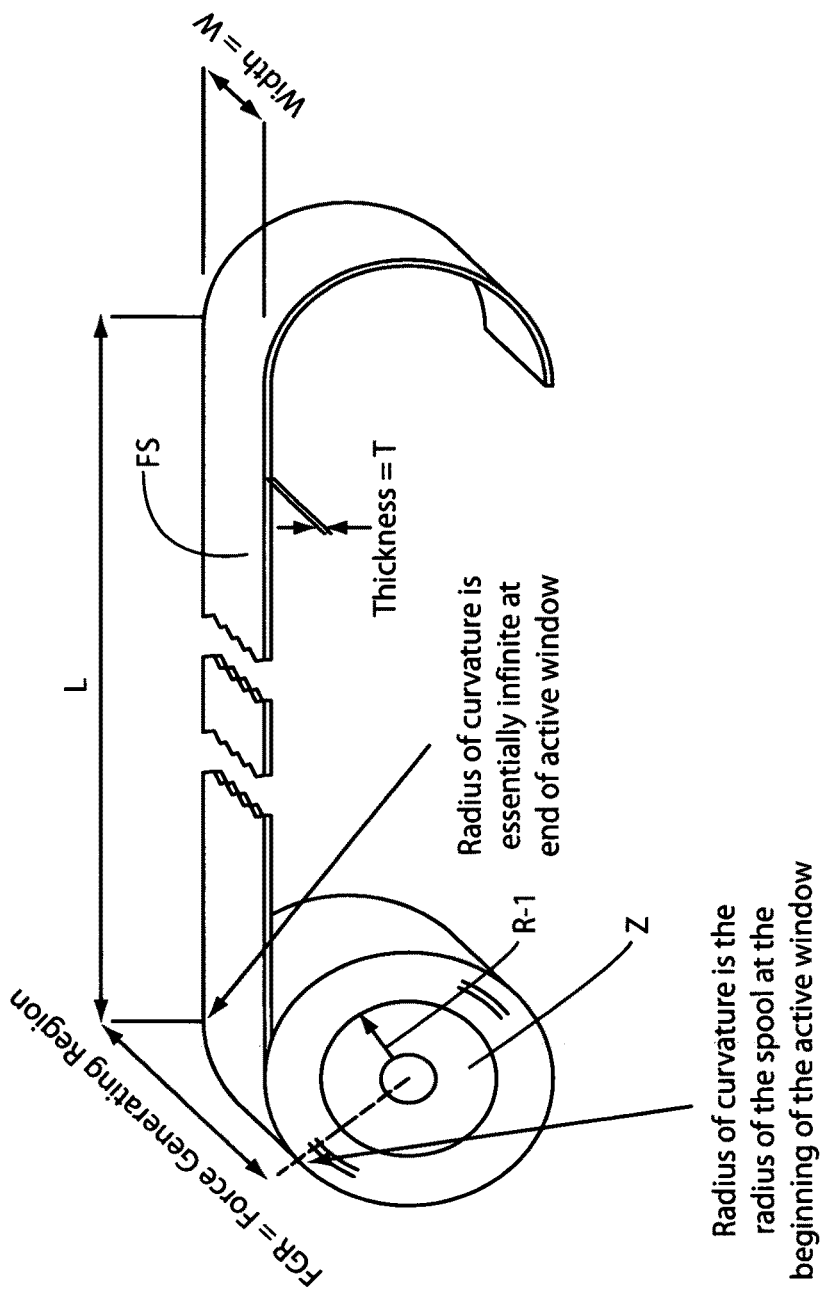
FIG. 97 is a generally perspective view of a prior art retractable constant force spring as it appears in a partially expanded configuration.
Figure 98:
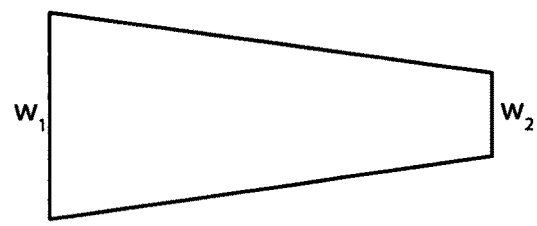
FIG. 98 is a generally illustrative view of the configuration of a modified retractable spring that would deliver a force that decreases by a factor of $w_1/w_2$ as a spring returned from its fully extended configuration to its fully coiled configuration.
Figure 98A:
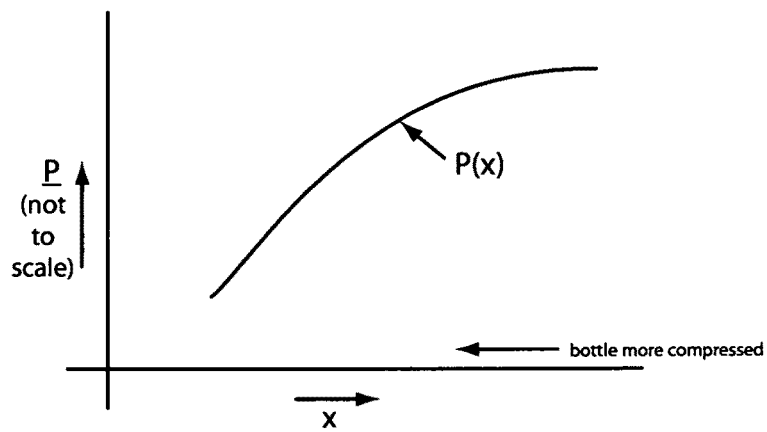
FIG. 98A is a generally graphical representation plotting pressure versus the length of the reservoir container when a constant force spring is used to compress a bellows-like reservoir container.
Figure 98B:
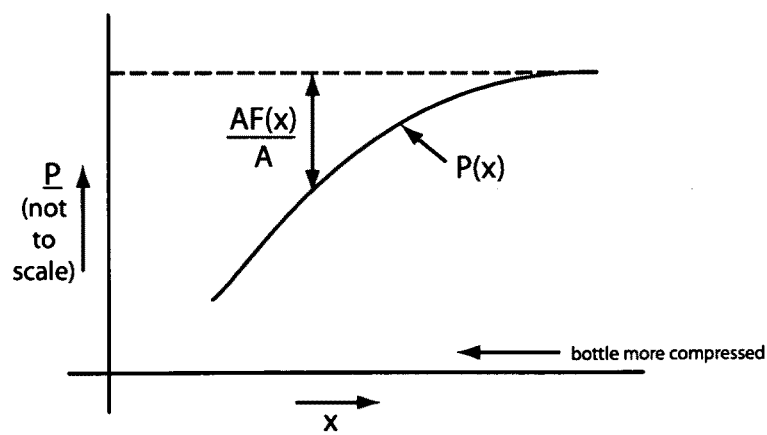
FIG. 98B is a generally graphical representation, similar to FIG. 94A, plotting pressure versus the degree of compression for the reservoir container when the container is compressed by a constant force spring.

To enable the fluid to flow from the reservoir 74 to the patient via the administration set 495 which is somewhat similar in construction and operation to the previously described administration set 130 illustrated in FIG. 8A, the fluid control locking means must be operated in the manner presently to be described. The administration set 495 here comprises a first leg 495a that is sealably interconnected with an outlet port formed in the on-off selector of the vial control assembly, the character of which will presently be described (FIG. 82), and a second leg 495b that is interconnected with outlet 497 of housing 468. As best seen in FIG. 80, interconnected within the second leg 495b is a conventional clamp 140, a conventional gas vent and filter 142, a generally Y-shaped injector site generally designated by the numeral 144, and a "Y" connector 145. A luer connector 146 of conventional construction is provided at the distal end 136b of the administration line.

To permit fluid flow toward the rate control micro-channel 112, the rate control shaft, or housing 472, must be rotated to a position wherein a radially extending flow passageway 492 aligns with a flow passageway 488 formed in housing 468 (FIGS. 82B and 82D). Since passageway 488 is in communication with the rate control channel, fluid can flow through the micro-channel at a controlled, fixed rate depending upon the configuration of the channel into passageway 490, into passageway 494 and finally into passageway 496 (FIG. 82C). From passageway 442 the fluid will flow into the inlet 442a of the administration set for delivery to the patient at a predetermined fixed rate. During the fluid delivery step, any gases contained within the device reservoir and the various fluid passageways are vented to atmosphere via vent port 497 and passageway 497a (FIG. 82).

As previously mentioned, rotation of the rate control housing 472 cannot be accomplished until the rate control locking means is operated by the caregiver. In the present form of the invention, this rate control locking means comprises a plunger 502 that includes a locking finger 502a (FIG. 82) that prevents rotation of the rate control housing, unless and until the plunger is moved inwardly of the housing against the urging of a biasing means shown here as coil spring 505 that is housed within a chamber 508 formed in housing 468. Once the plunger is appropriately urged inwardly, rate control housing can be rotated from the "off" position into the fluid flow, or "on" position by grasping rotation fingers 510 and imparting a rotational force to the rotating fingers.

Fluid flow from the reservoir 74 toward the patient can be prevented through operation of the disabling means of the invention. This important disabling means, which is illustrated in FIG. 82 and is similar in construction and operation to that previously described in connection with FIGS. 79, 80 and 81, comprises the previously identified disabling shaft 480. As indicated in the drawings, when the disabling shaft 480 is pushed inwardly the forward portion of the disabling shaft will move into cavity 455a, thereby blocking fluid toward the internal passageway 496. By stopping fluid flow in this manner, the apparatus is substantially safely disabled until the disabling shaft is once again returned to the starting position.

Additive sub-system 514, the details of construction and operation of which will presently be described, is also operably interconnected with the control portion 464 in the manner best seen in FIG. 31. As shown in FIGS. 2, 3 and 7, reservoir housing 52 which can be constructed from metal, plastic or any suitable material, includes a generally cylindrically shaped wall portion 62 and a base portion 62a.

Considering now the details of the construction of the previously mentioned adding means of this latest form of the invention, this important means for controllably delivering a second medicament to the patient here comprises an additive sub-system 514 of the construction illustrated in FIGS. 86 through 93 of the drawings. Additive sub-system 514, which is operably interconnected with housing 464 of the control portion of this latest form of the invention, here comprises a generally tubular-shaped vial housing 516 having a chamber 516a for telescopically receiving a medicament-containing, fill vial assembly 364 of the character previously described in connection with FIG. 50. Housing 516 can be constructed from metal, plastic or any suitable material, and includes a generally cylindrically shaped wall portion 516b and a base portion 516c. Formed on base portion 516c is a dovetail receiving groove 519 (FIG. 85), the purpose of which will presently be described.

An elongated needle holding component 520, which is disposed within chamber 516a, functions to hold the fill-vial assembly 364 in a proper position within chamber 516a and, in a manner presently to be described, also functions as a fill-vial pusher member.

As shown in FIG. 86, needle holding component 520 carries a longitudinally extending, elongated hollow needle 522 having a flow passageway 522a that communicates with an elongate fluid passageway 524 that is provided within needle holding component 520. Fill-vial 364, needle holding component 520, and hollow needle 522 all form a part of the adding means of the apparatus of this latest form of the invention. The method of operation of this latest adding means will presently be described.

As previously discussed and as shown in FIG. 50, the medicament containing fill-vial 364 comprises a container that is sealed at one end by an end wall 364a and at the other end by slidable, elastomeric plunger 372 having a pierceable, central wall 372a.

As best seen in FIGS. 86 through 92 of the drawings, this latest form of the apparatus of the invention includes a novel selector means that is of a somewhat different construction from that previously described selector means that included an on-off selector 523. This novel selector means includes a vial plug 526 that is closely received within a cavity 527 formed in needle holding component 520 (FIGS. 86 and 93). The vial plug 526 includes a pierceable membrane 526a that is pierceable by the piercing end 528a of an externally threaded piercing shaft 528 that is carried within a threaded bore 529 formed in the forward part of housing 516 (FIG. 93). Piercing shaft 528 is operably interconnected with an on-off selector 532 that is rotatably connected to housing 516 in the manner shown in FIG. 86 of the drawings. Selector 532 is held in position within housing 516 by a retaining ring 533 that is of the construction shown in FIG. 93 of the drawings. Rotation of selector 532 by gripping the finger engaging arms 532a will cause movement of the piercing shaft 528 from a first retracted position shown in FIG. 86 to a second piercing position, wherein piercing end 528a will pierce pierceable membrane 526a of plug 526, thereby opening communication between passageway 524 and the outlet 534 of selector 532 to which the administration set 495 is interconnected in the manner shown in FIGS. 80 and 81.

As best seen in FIG. 84 of the drawings, housing 464 of the control portion of the dispenser unit is provided with a dovetail connector segment 464c that is slidably receivable within the groove 519 formed in the base 516c of the additive housing. The additive sub-system of this latest form of the apparatus of the invention can readily be interconnected with housing 464 of the control portion of the dispenser unit by mating the dovetail connector segment 464c with the groove 519 formed in the base 516c and sliding the additive sub-system inwardly of the dovetail connector segment.

With the additive subsystem interconnected with the housing 464 of the control portion of the dispenser unit and with communication having been established between passageway 522a of needle 522 in the manner described in the preceding paragraphs, a pressure exerted on container 364 urging the container into chamber 516a of additive housing 516 will cause the needle end 522a to pierce wall 372a of plug 372. A continued inward pressure exerted on container 364 will cause the slidable elastomeric plunger 372 to be moved inwardly of the fluid reservoir 364b by the needle holding component 520. The inward movement of plunger 372 will, in turn, cause the fluid "F" contained within the reservoir 364b of the container to flow into flow passageway 522a of needle 522, then into fluid passageway 524, then into fluid passageway 528b of piercing shaft 528, and finally into the administration set 495 via outlet 534.

Turning now to FIGS. 94 through 96A, still another form of the apparatus of the invention is there illustrated. This form of the apparatus, which is generally identified by the numeral 550 is similar in many respects to the embodiment illustrated in FIGS. 44 and 45 of the drawings and like numerals are used in 94 through 96A to identify like components. The primary difference between this latest embodiment of the invention and the earlier described embodiments resides in the differently configured stored energy means. More particularly, in this form of the invention, the stored energy means comprise a plurality of circumferentially spaced variable force springs 552 that are somewhat similar in construction to prior art constant force springs, but have been modified to produce highly specific and desirable linear and non-linear force-distention curves to meet the fluid delivery requirements of the invention. For example, as will be discussed in greater detail in the paragraphs that follow, in this latest form of the invention the elongated band or strip portion 552a of the spring has been modified to exhibit a cross-sectional mass that varies along the length of the band.

Referring particularly to FIGS. 94 and 95, like the earlier described embodiments of the invention, this latest form of the dispensing apparatus comprises two stand-alone, interconnectable assemblies of the character shown in FIGS. 94 and 95. First assembly 554 is of a somewhat different construction, while second assembly 54 is substantially identical in construction and operation to the previously described second assembly 54. The primary difference between first assembly 554 and the previously described assembly 252 resides in the provision of the different stored energy means for moving the carriage 264 from a first retracted position to a second advanced position. Second assembly 54 includes a rate control assembly that permits the delivery of fluid to the patient at substantially a fixed rate.

The reservoir defining component 555 of this latest form of the invention is somewhat similar in construction and operation to the previously described and is constructed in accordance with aseptic blow-fill seal manufacturing techniques of the character previously described. Following molding, filling and sealing, the reservoir defining component is sterilized at a relatively high temperature.

In a manner presently to be described, fluid medicament reservoir 74 of the fluid reservoir assembly 252 is accessible via the penetrating member 58 of the fluid delivery and control assembly 54. More particularly, penetrating member 58 is adapted to pierce closure wall 72 as well as a pierceable membrane 78 (FIG. 44) which is positioned over closure wall 72 of by means of a closure cap 80 which is affixed to the neck portion 70 of reservoir defining assembly 56 (see FIG. 11).

Considering now in greater detail the first assembly 554 of this latest form of the fluid dispensing apparatus, this assembly comprises a generally cylindrically shaped housing 256 having a forward portion 256a and a rearward portion 256b. Forward portion 256a, which is sealed by a sterile barrier 258 having a pull tab 258a, includes an externally threaded neck 260 that is receivable within threaded cavity 84 of the second assembly 54.

In addition to the reservoir defining component 555, assembly 554 includes a carriage assembly 264 and the differently configured stored energy means that is operably associated with the carriage assembly for moving the carriage assembly between the first retracted position and the second advanced position. Carriage assembly 264 includes a base assembly 266 that includes a forward portion having, a base 266, a reservoir receiving flange 266b and a fluid level indicator boss 266c. Base assembly 266 also includes a rear portion having housing 266d that is provided with a threaded carriage locking member receiving cavity 266e (see also FIG. 47). Mounted within the housing 273 is the important stored energy means of this latest form of the invention which here comprises a pair of variable force springs 556. Carriage assembly 264 is releasably locked in its first position by a novel carriage locking means, the character of which was previously described.

As in the earlier described embodiments of the invention and as illustrated in FIG. 94 of the drawings, reservoir defining component 555 is formed using a co-extrusion process. Component 555 here comprises an integrally formed, hermetically sealed container that includes a front portion 555a, a rear portion 555b and a collapsible accordion-like, continuous, uninterrupted side wall 555c that interconnects the front and rear portion of the container. As illustrated in the drawings, the accordion like side wall 555c comprises a multiplicity of adjacent generally "V" shaped interconnected folds, 555d. Rear portion 555b of the container includes an inwardly extending ullage segment 562 having a side wall 562a and an end wall 562b. As illustrated in FIG. 94, end wall 562b includes a generally hemispherical shaped protuberance 564. Front portion 555a of the container includes an integrally formed neck 566 having a closure wall 568. Front portion 555a, rear portion 555b and side wall 555c cooperate to define the fluid reservoir 570 of the fluid reservoir assembly. As shown in FIG. 96A, side wall 555c is a laminate construction comprising individual laminates L-1, L-2, L-3, L-4 and L-5. As previously mentioned, this novel laminate construction comprises a co-extrusion formed by a blow-fill-seal process.

Co-extrusion in the blow-fill-seal process is typically used in the prior art to package liquids that are either oxygen or moisture sensitive. Further, oxygen sensitive products, as well as compounds that need a longer shelf life, are frequently packaged using co-extruded plastic. Blow-Fill-Seal is a preferred drug packaging modality because polypropylene (PP) and polyethylene are typically used. Compared to a traditional flexible solution bag made from PVC, a PP or PE, the blow-fill-seal container is much less permeable.

With suitable resins, co-extruded plastic blow-fill-seal containers can readily be constructed to prevent water vapor loss out of container, and ingress of oxygen into the container contents. The typical co-extruded material is a five layer system that exhibits substantially the same thickness as a comparable container constructed from a single layer resin material. That is, each layer is ⅕ of the equivalent container that is homogeneous (non-laminate). However, it should be recognized that, at a minimum a three layer system is required to suit the purposes of the present invention, while a system having up to about 10 layers would be feasible for certain applications.

In a typical five layer co-extruded blow-fill-seal container, the laminate material may comprise an inert internal polyolefin, such as PP. The barrier material in the center of the five layer laminate may be selected to exhibit gas or water barrier properties, or both. The barrier material is affixed to the inert hydrophobic plastic layer (e.g. PP) via a binder layer.

Although a variety of plastic resins may be used for the co-extrusion of blow-fill-seal containers, polyolefins (e.g. PP of LDPE) are desirable to be in contact with the parenteral solution, as this material is inert and hydrophobic.

It is well know in the food packaging industry that Ethylene-Vinyl Alcohol Copolymer (EVOH) is an excellent gas barrier. Additionally, a variety of nylon based materials (also referred to as polyamides (PA)) can act as strong vapor barriers. Those skilled in the art will also recognize cyclic polyolefin copolymers (COP) for their effectives as water barriers, and therefore there use in co-extruded blow-fill-seal containers.

Other suitable barrier materials may included, but are not limited to, polyvinyl chloride, oriented polyvinyl chloride (OPVC), biaxially oriented PET, silica-deposited resins, sequentially biaxially oriented polyvinyl alcohol, biaxially oriented polyester, vinylidene chloride (or copolymers of vinylidene chloride and methyl methacrylate), polyacrylonitrile (PAN), oriented polyethylene terephthalate (OPET), polystyrene (PS), ethylene methyl acrylate copolymer (EMA), and other polymer resins known to those skilled in the art which are generally termed "high gas barrier polymers" HBP. Additionally, those skilled in the art will recognize multi-lamellar barrier materials, such as those based on the blends of high-density polyethylene (HDPE) and co-polyester (PETG) prepared via melt extrusion, and poly(ethylene-co-acrylic acid) (EAA) as a compatibilizer incorporated into the blends, as possible barrier materials as well.

A variety of binder materials may be used to "tie" the dissimilar polyolefin and the barrier materials together. These include, but are not limited to agents of the formula AMXP in which AM is a backbone copolymer prepared by copolymerizing propylene with α-olefins and where X is selected from among citraconic anhydride, fumaric acid, mesaconic acid, the anhydride of 3-allylsuccinic acid and maleic anhydride, and P is a polyamide oligomer prepared from caprolactam, 11-aminoundecanoic acid or dodecalactam; ethylene vinyl acetate copolymer (EVA); a coextrusion binder comprising a metallocene polyethylene (A1), a cografting monomer said cografting monomer being an unsaturated carboxylic acid grafting monomer or functional acid derivative thereof, and an ethylene homopolymer; an ethylene copolymer wherein the comonomer is (a) an alpha-olefin, (b) an ester of an unsaturated carboxylic acid or (c) a vinyl ester of a saturated carboxylic acid; and a hydrocarbon elastomeric copolymer; and Celanex (polybutylene terephthalate (PBT) copolymer binder).

Although the most common coextrusion systems seem to be a 5 layer laminate, a variety of different "size" laminate materials would be workable in BioQ dispensers and fit the spirit of the expanded invention. At a minimum, a three layer sandwich would be required (i.e. inert polyolefin, binder and barrier) would be required. At a maximum, many repeated layers that comprise both oxygen and moisture barriers would be feasible.

A more detailed consideration of the stored energy sources, or variable force springs of this latest form of the invention will now be undertaken. At the outset it is to be understood that the objective of many prior art fluid and drug delivery systems is to deliver fluid at a constant flow rate. One method for achieving a constant flow rate over time involves ensuring that the pressure driving the fluid through the device is constant, i.e., the pressure inside the fluid reservoir of the apparatus is constant. In this latest form of the invention, achieving constant pressure in the bellows-like fluid reservoir 94 of the device is accomplished in a unique manner by modifying a typical constant force spring, such as a Negator spring "NS" of the character shown in FIG. 97. Negator springs are readily commercially available from a number of sources including Stock Drive Products/Sterling Instruments of New Hyde Park, N.Y.

The prior art Negator extension spring comprises a prestressed flat strip "FS" of spring material that is formed into virtually constant radius coils around itself or on a drum "Z" having a radius R-1 (FIG. 93). The area identified in FIG. 93 of the drawings as "FGR" designates the "active region" or "the force generating region" of the constant force spring. It should be understood that in this "active region" the radius of curvature of the spring changes and it is this change in radius of curvature of the spring that is responsible for the generation of the force. In fact, the radius of curvature changes from essentially infinity to a value equal to the radius R-1 of the spool on which the spring is wound. As will be discussed in greater detail hereinafter, increasing the mass of material in this "force generating region" will increase the force provided by the spring. Conversely, decreasing the mass of material in the "force generating region" will result in a reduction of the force generated by the spring. The mass in the active region can be changed by changing the thickness of the spring, the width of the spring, the density of material of the spring, or any combination of these. It should be further noted that because the force generating region takes up some portion of the length of the spring it will tend to average any point-by-point changes in physical or structural properties of the spring. The variable L shown in FIG. 93 of the drawings is defined to be the distance from the force generating region to the end of the spring. When deflected, the spring material straightens as it leaves the drum (see FIG. 93). This straightened length of spring actually stores the spring's energy through its tendency to assume its natural radius.

The force delivered by a typical prior art constant force spring, such as the Negator extension spring, depends on several structural and geometric factors. Structural factors include material composition and heat treatment. Geometric factors include the thickness of the spring "T", the change in radius of curvature of the spring as the spring is extended, and the width "W" of the spring.

Turning now to a consideration of the novel variable force springs of the present invention, these springs can be constructed from various materials, such as metal, plastic, ceramic, composite and alloys, that is, intermetallic phases, intermetallic compounds, solid solution, metal-semi metal solutions including but not limited to Al/Cu, Al/Mn, Al/Si, Al/Mg, Al/Mg/Si, Al/Zn, Pb/Sn/Sb, Sn/Sb/Cu, Al/Sb, Zn/Sb, In/Sb, Sb/Pb, Au/Cu, Ti/Al/Sn, Nb/Zr, Cr/Fe, non-ferrous alloys, Cu/Mn/Ni, Al/Ni/Co, Ni/Cu/Zn, Ni/Cr, Ni/Cu/Mn, Cu/Zn, Ni/Cu/Sn. These springs comprise a novel modification of the prior art constant force springs to provide variable springs suitable for use in many diverse applications With the forgoing in mind, if one wanted to produce a spring that delivered a force that increased by a factor of two as the spring returned from its fully extended conformation to its equilibrium, or fully coiled conformation, one would require that, as illustrated in FIG. 94 of the drawings, the width of the spring change by a factor of two along its length. In the example illustrated in FIG. 94A, the force will decrease by a factor of $w_1/w_2$ as the spring changes from a fully extended configuration to a fully retracted configuration.

With the forgoing in mind, one form of the modified spring of the present invention can be described algebraically as follows:

If x denotes the position of a point along a line that is parallel to the longitudinal axis of the spring and w(x) denotes the width of the spring at that point then:

$$w(x)=(\text{constant})x$$

This describes the case wherein the width varies linearly with x as is shown in FIG. 94 of the drawings.

However, it is to be observed that the relationship between a position along the longitudinal axis of the spring and the width of the spring at that position need not be linear as shown in FIG. 94. Further, the width of the spring could be any arbitrary function of x. Thus:

$$w(x)=f(x)$$

where (x) denotes an arbitrary function of x.

Using this concept, a spring can be designed that can be used to controllably compress a bellows type reservoir, such as reservoir 94, which when compressed by the modified spring exhibits a pressure vs. degree of compression curve of the character shown in FIG. 94B. Stated another way, it is apparent that the concept can be employed to design a spring that generates a pressure that is independent of the degree of compression of the bellows-type reservoir.

By way of example, suppose that the pressure vs. degree of compression curve for a bellows-like container when compressed by a constant force spring is exemplified by the curve P(x) and the force of the constant force spring is identified as "FCFS". Further assume that the drop in pressure as the container is compressed is due to the force "BF(x)", which is the force required to compress the container. Then the net force producing the pressure in the container can then be written:

$$F(x)=FCFS-BF(x)$$

Assume for simplicity that the area on which the force F acts is constant and is represented by "A". Then the pressure in the bottle is:

$$P(x)=(FCFS-BF(x))/A$$

This equation describes, in functional form, the curve labeled P(x) in FIG. 94B, and includes explicitly the contributions of the two forces generating the pressure within the reservoir 94 of the bellows-like container, that is the force due to the spring and the force due to the bellows-like container.

The forgoing analysis allows one to design a spring, the force of which changes in such a way that the sum of all forces generating the pressure in the container is independent of the degree of the compression of the container, i.e., independent of the variable x. The force delivered by such a spring can be stated as:

$$F_{ms}(x)=FCFS+AF(x)$$

Where "FCFS" is the force delivered by the original constant force spring and AF(x) is an additional force whose functional form is to be determined. Thus, the modified spring can be thought of as being composed of two parts, one part delivers the force of the original constant force spring (a force independent of x) and the other delivers a force that depends on the variable x.

For this system the net force generating the pressure in the reservoir of the bellows-like container is stated as:

$$FS(x)=F_{ms}(x)-BF(x)=FCFS+AF(x)-BF(x)$$

Assuming that:

$$AF(x)=BF(x) \text{ for all } x.$$

Then the total force compressing the container is:

$$FS(x)=FCFS+AF(x)-AF(x)=FCFS$$

which force is independent of the degree of compression of the container, and wherein the pressure within the container is independent of the degree of compression of the container.

$$P_{ms}(x)=(FCFS+AF(x)-AF(x))/A=FCFS/A$$

Where $P_{ms}(x)$ denotes the pressure in the fluid reservoir when the modified spring of the invention is used.

In designing the modified spring of the present invention, the information contained in the pressure vs. displacement curve when the container is compressed by a constant force spring can be used to determine how the cross-sectional mass, in this case the width of the spring, must vary as a function of x in order that the pressure in the container when compressed with the modified spring remains constant.

The force delivered by the spring being linearly dependent on the width of the spring if all other things remain constant, thus:

$$AF(x)=(\text{constant})w(x)$$

Substituting this into equation:

$$P(x)=(FCFS-BF(x))/A, \text{ then:}$$

$$P(x)=(FCFS-AF(x))/A=(FCFS-\text{constant})w(x))/A$$

However, it is to be observed that $FCFS/A-P(x)$ is just the difference between the two curves shown in FIG. 94B, $FCFS/A$ being the horizontal line. Thus, the modification to the width, denoted $w(x)$, of the original constant force spring is proportional to the difference between the two curves shown in FIG. 94B. In other words, the shape of the change in the width of the spring as a function of x is similar to the difference between the two curves as a function of x. Furthermore, one can simply "read off" the shape of the curve $w(x)$ from the pressure vs. displacement curve.

The broader utility of a variable force spring whose width defines the specific force may be that the spring design can be appropriately constructed to deliver a non-linear and highly variable force to meet a specific requirement. In this way, a spring that has a width that simply decreases as it is unrolled could be used. Alternatively, the spring could have an increasing width, followed by a width that decreases again during its distention. The spring force provided is therefore highly tunable to meet a variety of applications and requirements, simply by constructing a spring of specific width at the desired distension.

Figure 99:
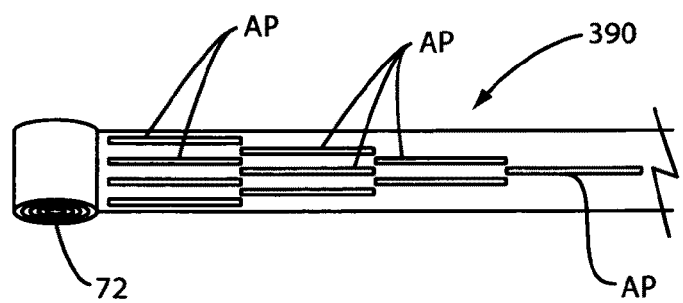
FIG. 99 is a generally perspective view illustrating an alternate form of variable force spring of the invention.
Figure 99A:
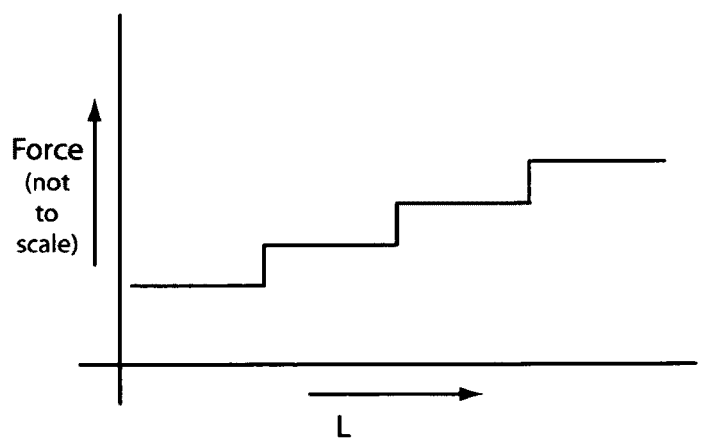
FIG. 99A is a generally graphical representation plotting force exerted by the alternate form of variable force spring illustrated in FIG. 94 as a function of the length of the spring.

Referring to FIGS. 99 and 99A of the drawings, still another form of variable force spring having varying cross-sectional mass along its length is there illustrated. In this instance, the varying cross-sectional mass is achieved by a constant force spring wherein the force generating region of the spring has been modified to include a plurality of spaced-apart apertres "AP" along its length. As shown in FIG. 99A, which is a schematic plot (not to scale) of force versus cross-sectional mass, the spring uniquely provides an increasing force in a stair step fashion as it is retracted. It is to be understood, that the apertures formed in the pre-stressed strip of spring material can be located in any desired configuration and can be both transversely and longitudinally spaced-apart to provide the desired force as the spring is retracted.

Figure 100:
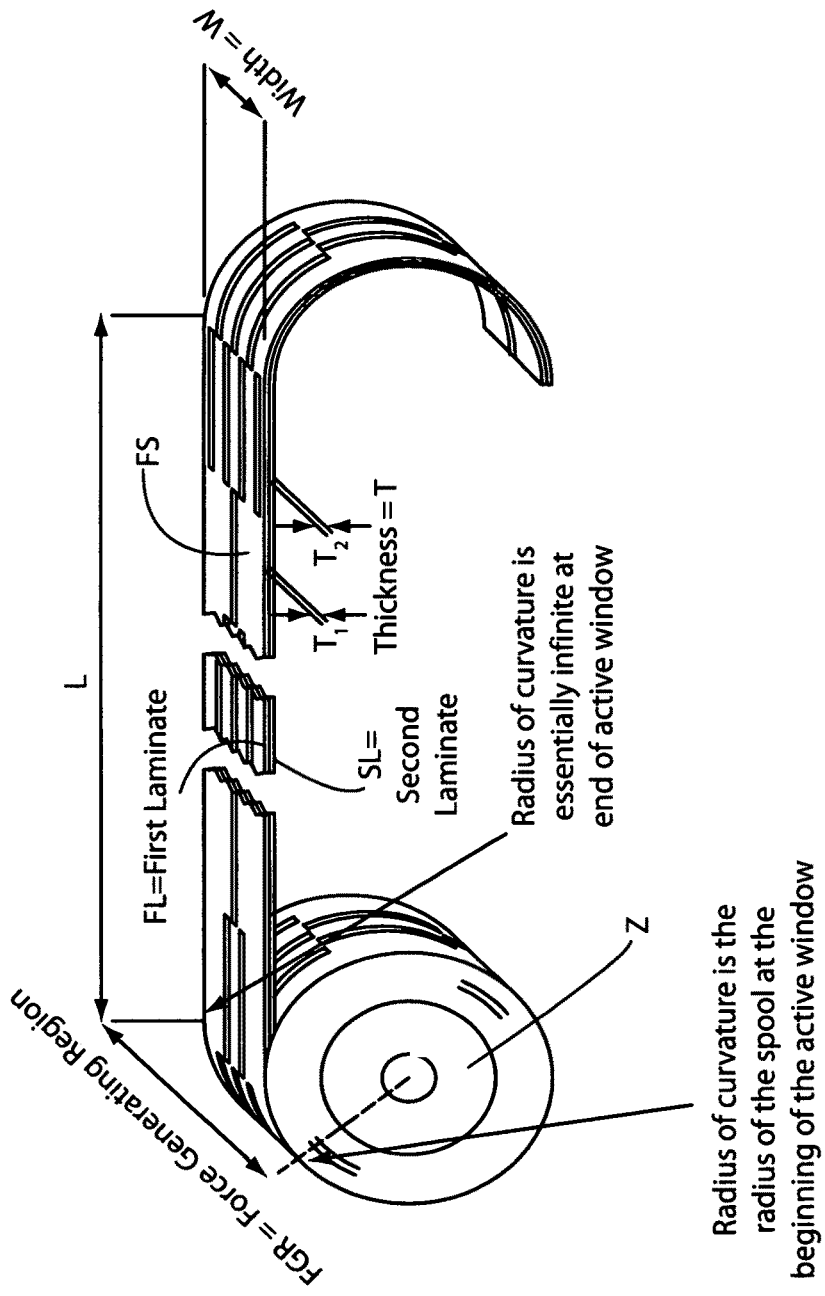
FIG. 100 is a generally perspective view illustrating still another form of variable force spring of the invention.

FIG. 100 is a generally perspective view of still another form of the retractable spring of a modified configuration that can be used in an apparatus of the character illustrated in FIGS. 94 and 95 of the drawings. This latter form of the retractable spring here comprises a novel laminate construction made up of a first laminate FL and a second interconnected laminate SL. The varying cross-sectional mass is once again achieved by providing a plurality of the elongated transversely and longitudinally spaced-apart apertures, or slits.

Figure 101:
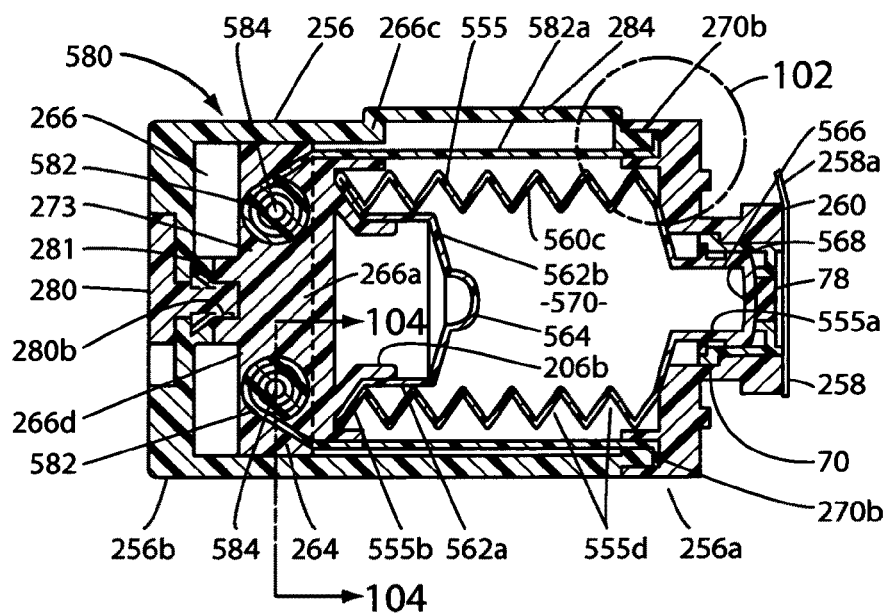
Figure 102:
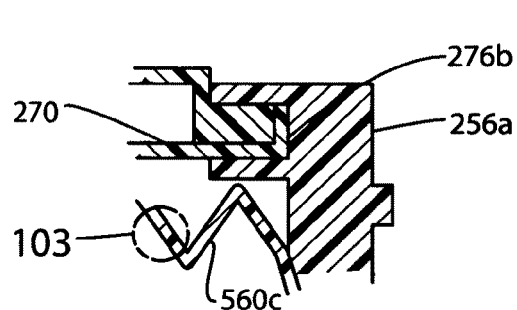
Figure 103:
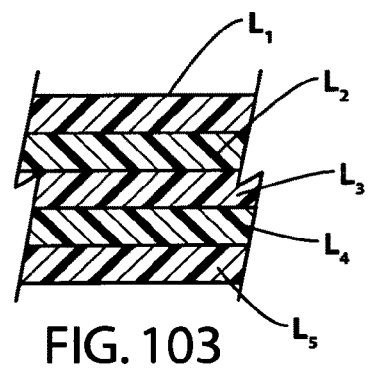

Turning now to FIG. 100, yet another form of the first assembly of the apparatus of the invention is there shown and generally identified by the numeral 580. First assembly 580 is similar in many respects to the embodiment illustrated in FIG. 94 and like numerals are used in FIGS. 101 and 102 to identify like components. The primary difference between first assembly 580 and the previously described assembly 554 resides in the provision of the different stored energy means for moving the carriage 264 from a first retracted position to a second advanced position. As before, second assembly 54 includes a rate control assembly that permits the delivery of fluid to the patient at substantially a fixed rate.

In this latest form of the invention, the stored energy means comprise a plurality of circumferentially spaced variable force spring assemblies 582 that are somewhat similar in construction to prior art constant force spring assemblies, but have been modified to produce highly specific and desirable linear and non-linear force-distention curves to meet the fluid delivery requirements of the invention. For example, as will be discussed in greater detail in the paragraphs that follow, in this latest form of the invention the elongated band or strip portion 582a of the spring is coiled about a spring drum 584 in predetermined varying degrees of tightness. Accordingly, like the earlier described variable force springs in which the elongated band or strip portion of the spring has been modified to exhibit a cross-sectional mass that varies along the length of the band, springs with a variation of coil tightness such as illustrated in FIGS. 104 and 105, can produce highly specific and desirable linear and non-linear force-distention curves to meet the fluid delivery requirements of the invention. This type of "inter-wound negative gradient" spring has no slot. In fact, it is that the winding process is done precisely to create a "negative gradient" so that as the spring retracts, it provides a higher force.

Turning to FIGS. 104 and 105 of the drawings, one example of the spring coiling method is there illustrated. As depicted in FIG. 104, the band portion 582 of the spring is initially wound tightly about the drum 584 to produce a first segment 587 having a diameter "D-1". This done, the band portion is then coiled, or wound more loosely about the drum 584 to produce a second segment 589 having a diameter "D-2". Finally, the band portion is coiled, or wound even more loosely about the drum 584 to produce a third segment 591 having a diameter "D-3".

By coiling the springs about their respective drums with a variation of coil tightness in the manner described in the preceding paragraph and as illustrated in FIGS. 104 and 105, springs having highly specific and desirable linear and non-linear force-distention curves can be produced which will meet the fluid delivery requirements of the invention.

Spring assemblies, such as those depicted in FIGS. 104 and 105 of the drawings, that exhibit a variation of coil tightness that produce highly specific and desirable linear and non-linear force-distention curves to meet the fluid delivery requirements of the invention, are available by custom order from various sources, including Vulcan Mfg. & Spring Company of Telford, Pa.

Figure 106:
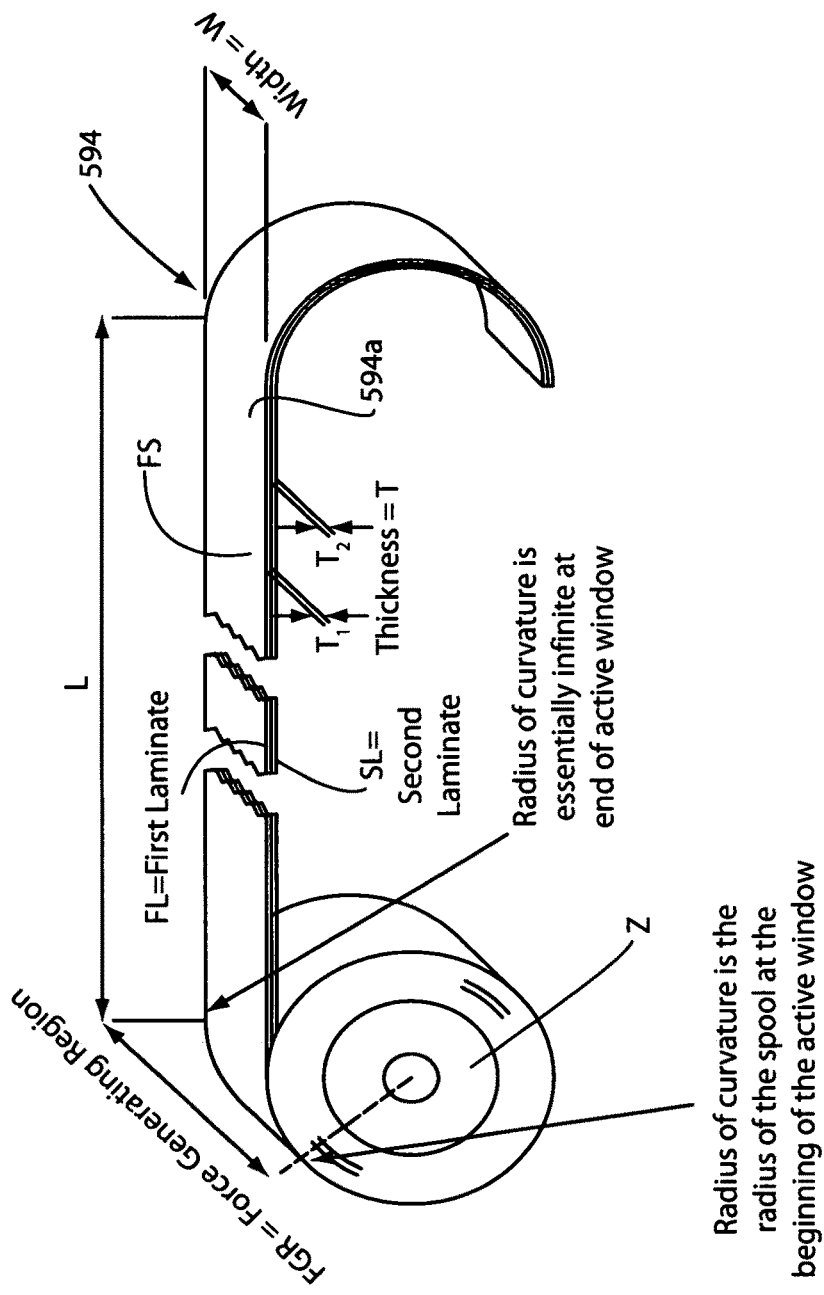

Turning now to FIG. 106 of the drawings, still another form of variable force spring that can be used with the apparatus illustrated in FIGS. 94 and 95 is there shown. This spring, which is generally identified by the numeral 594, is of a novel laminate construction. This latter form of the retractable spring here comprises a novel laminate construction made up of a first laminate FL and a second interconnected laminate SL. As in the spring of FIGS. 104 and 105, the elongated band or strip portion 594a of the spring is coiled about a spring drum Z in predetermined varying degrees of tightness. Accordingly, like the earlier described variable force springs in which the elongated band or strip portion of the spring has been modified to exhibit a cross-sectional mass that varies along the length of the band, springs with a variation of coil tightness such as illustrated in FIGS. 104 and 105, can produce highly specific and desirable linear and non-linear force-distention curves to meet the fluid delivery requirements of the invention. As before, this type of "inter-wound negative gradient" spring has no slot. In fact, it is that the winding process is done precisely to create a "negative gradient" so that as the spring retracts, it provides a higher force. Springs with a variation of coil tightness that produce highly specific and desirable linear and non-linear force-distention curves to meet the fluid delivery requirements of the invention, are available by custom order from various sources, including Vulcan Mfg. & Spring Company of Telford, Pa.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. A two part apparatus for dispensing medicaments to a patient comprising:
   (a) a first stand alone assembly comprising a housing having a threaded neck portion, an integrally formed, hermetically sealed collapsible container for containing a medicinal fluid disposed within said housing and stored energy means for controllably collapsing said sealed container;
   (b) a second stand alone assembly threadably interconnectable with said first assembly, said second assembly including:
      (i) a housing having a threaded neck receiving portion for receiving the threaded neck portion of said first assembly, said housing having a longitudinally extending bore and including a penetrating member for penetrating said collapsible container of said first stand alone assembly;
      (ii) fluid delivery and control means carried by said housing of said second assembly for controlling the flow of medicinal fluid from said container of said first assembly toward the patient, said fluid and delivery and control means comprising a rate control shaft rotatably mounted within said longitudinally extending bore, said rate control shaft comprising an elongated body portion, a forward flange and a forwardly extending finger engaging portion connected to said forward flange, said elongated body portion connected to said flange, said elongated body portion having a longitudinally extending fluid passageway that communicates with said penetrating member and a plurality of circumferentially spaced apart, radially extending outlet fluid passageways that communicate with said longitudinally extending fluid passageway; and
      (iii) a medicament vial receiving assembly connected to said housing of said second assembly;
   (c) a medicament containing vial inter-connectable with said medicament vial receiving assembly.

2. The apparatus as defined in claim 1 in which said collapsible container includes a front portion, a rear portion and a collapsible accordion-like, continuous, uninterrupted side wall that interconnects said front and rear portions, said front portion of said collapsible container including a closure wall and said rear portion of said collapsible container including an inwardly extending ullage segment.

3. The apparatus as defined in claim 1 in which said first assembly further includes a carriage housed within said housing of said first assembly, said carriage being operably associated with said container and with said stored energy means and being movable by said stored energy source from a first retracted position to a second advanced position.

4. The apparatus as defined in claim 1 in which said storage energy means comprises a spring.

5. The apparatus as defined in claim 1 in which said stored energy means comprises a constant force spring.

6. An apparatus for dispensing medicaments to a patient comprising first and second stand alone threadably interconnectable assemblies, said first assembly comprising a housing having a threaded neck portion, a first removable cover covering said threaded neck portion, an integrally formed, hermetically sealed collapsible container having a reservoir for containing a first medicinal fluid disposed within said housing, said collapsible container having an outlet, and stored energy means for controllably collapsing said sealed container and said second assembly including:
   (a) a housing having an outlet, a cavity, a longitudinally extending bore and a neck portion, a second removable cover covering said neck portion of said second assembly and fluid delivery and control means carried within said housing of said second assembly for controlling the flow of medicinal fluid from said container of said first stand alone assembly toward said outlet of said housing of said second stand alone assembly, said second stand alone assembly including a penetrating member for penetrating said container of said first stand alone assembly, said fluid delivery and control means comprising:
      (i) a rate control assembly, including a rate control plate disposed within said cavity of said housing; and
      (ii) a rate control shaft rotatably mounted within said longitudinally extending bore, said rate control shaft having a longitudinally extending fluid passageway that communicates with said penetrating member and a plurality of circumferentially spaced apart, radially extending outlet fluid passageways that communicate with said longitudinally extending fluid passageway; and
   (b) an adding assembly for controllably dispensing a second medicinal fluid to the patient.

7. The apparatus as defined in claim 6 in which said first assembly further includes a carriage carried within said housing of said first assembly, said carriage being operably associated with said container and with said stored energy means and being movable by said stored energy means from a first retracted position to a second advanced position.

8. The apparatus as defined in claim 6 in which said storage energy means comprises a constant force spring.

9. The apparatus as defined in claim 6 in which said collapsible container includes a front portion, a rear portion and a collapsible accordion-like, continuous, uninterrupted side wall that interconnects said front and rear portions, said front portion of said collapsible container including a closure wall and said rear portion of said collapsible container including an inwardly extending ullage segment.

10. The apparatus as defined in claim 6 in which said adding means comprises:
   (a) a fill-vial containing said second medicinal fluid;
   (b) an additive housing integrally formed with said housing of said second assembly, said additive housing having a chamber;
   (c) a needle holding component disposed within said chamber of said additive housing for holding said fill-vial; and (d) a hollow needle carried by said needle holding component.

11. An apparatus for dispensing medicaments to a patient comprising;
   (a) a first stand alone assembly including:
      (i) a housing having an outlet, a longitudinally extending bore and a threaded neck portion;
      (ii) a first removable sterile barrier connected to and sealing said threaded neck portion;
      (iii) an integrally formed, hermetically sealed collapsible container disposed within said housing, said collapsible container having a reservoir containing a first medicinal fluid, said reservoir having an outlet and including a front portion, a rear portion and a collapsible accordion-like, continuous, uninterrupted side wall that interconnects said front and rear portions, said front portion of said collapsible container including a closure wall and said rear portion of said collapsible container including an inwardly extending ullage segment; and
      (iv) stored energy means disposed within said housing for controllably collapsing said sealed collapsible container; and
   (b) a second stand alone assembly threadably interconnectable with said first assembly, said second assembly including:
      (i) adding means for controllably dispensing a second medicinal fluid to the patient;
      (ii) a housing having a threaded neck receiving portion for receiving said threaded neck portion of said first stand alone assembly, a longitudinally extending bore and an outlet;
      (iii) fluid delivery and control means carried within said housing of said second assembly for controlling the flow of medicinal fluid from said container of said first assembly toward said outlet of said housing of said second assembly, said fluid delivery and control means including a penetrating member for piercing said closure wall of said collapsible container and comprising:

a. a rate control assembly, including a rate control plate having at least one micro-channel formed therein, said micro-channel having an inlet in communication with said penetrating member and with outlet of said collapsible container of said first assembly and an outlet in communication with said outlet of said housing of said second assembly; and b. a rate control shaft rotatably mounted within said longitudinally extending bore of said housing of said second assembly, said rate control shaft having a flange and at least one radially extending inlet passageway in communication with said outlet of said micro-channel and at least one radially extending outlet passageway in communication with said outlet of said housing of said second assembly; and c. rate control locking means for preventing rotation of said rate control shaft, said rate control locking means comprising a plunger connected to said flange of said rate control shaft.

* * * * *